(12) United States Patent
Dávila et al.

(10) Patent No.: US 7,883,880 B1
(45) Date of Patent: Feb. 8, 2011

(54) DNA POLYMERASE LAMBDA AND USES THEREOF

(75) Inventors: Luis Blanco Dávila, Madrid (ES);
Antonio Bernad Miana, Madrid (ES);
Orlando Domínguez López, Asturias (ES); Miguel García Díaz, Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 488 days.

(21) Appl. No.: 10/089,653

(22) PCT Filed: Oct. 2, 2000

(86) PCT No.: PCT/GB00/03784

§ 371 (c)(1),
(2), (4) Date: Sep. 30, 2002

(87) PCT Pub. No.: WO01/25442

PCT Pub. Date: Apr. 12, 2001

(30) Foreign Application Priority Data

Oct. 1, 1999 (ES) .................................... 9902169

(51) Int. Cl.
*C12N 9/12* (2006.01)
(52) U.S. Cl. ........................................ 435/194; 435/183
(58) Field of Classification Search ................. 435/194, 435/183; 530/350
See application file for complete search history.

(56) References Cited

U.S. PATENT DOCUMENTS 5,449,605 A  9/1995 Smulson et al.

FOREIGN PATENT DOCUMENTS

| WO | WO 90/02203 A2 | 3/1990 |
| WO | WO 99/06552 A2 | 2/1999 |
| WO | WO 99/38972 A2 | 8/1999 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
Ulaener and Giudice, Molecular Human Reproduction, vol. 3, No. 9, pp. 769-733, 1997.*
Aoufouchi, Said et al., "Two novel human and mouse DNA polymerases of the poIX family," *Nucleic Acids Research*, 28(18): 3684-3693 (2000).
Garcia-Diaz, Miguel, et al., "DNA polymerase lambda (pol lambda), a novel eukaryotic DNA polymerase with a potential role in meiosis." *Journal of Molecular Biology*, 301(4):851-867, (2000).
Database EMBL [Online] Hinxton UK; Jan. 7, 2000. Blanco L: "Mus musculus mRNA for DNA polymerase lambda (poll gene)" Accession No. AJ131889; abstract.
Database EMBL [Online] Hinxton, UK; Jan. 7, 2000. Blanco L: "*Homo sapiens* mRNA for DNA polymerase lambda (POLL gene)" Acession No. AJ131890; abstract.
Matsutani, Chikahide et al., "The XPV (xeroderma pigmentosum variant) gene encodes human DNA polymeraseeta." *Nature*, 399(6737):700-704 (1999).
Sharief, Farida S. et al., "Cloning and chromosomal mapping of the human DNA polymerase theta (POLQ), the eighth human DNA polymerase." *Genomics*, 59(1):90-96 (1999).
Sobol, R.W. et al., "Requirement of Mammalian DNA Polyerase-Beta in Base-Excicion Repair" *Nature*, 379(11): 183-186 (1996).

* cited by examiner

*Primary Examiner*—Richard G Hutson
(74) *Attorney, Agent, or Firm*—Quine Intellectual Property Law Group, P.C.; Paul Littlepage

(57) ABSTRACT

The present invention relates to the identification and isolation of a DNA polymerase and uses of this polymerase. In particular, the present invention describes the nucleotide sequence of the human gene for DNA polymerase lambda (Pol λ), the amino acid sequence of Pol λ, and the amino acid sequence of several isoforms derived from alternative splicing of its mRNA. The association of some of these isoforms with tumour samples makes Pol λ a marker for the diagnosis, prognosis and evolution of tumoral processes.

1 Claim, 8 Drawing Sheets

| Fragment | Name | Position/Relative size |
|---|---|---|
| 14 | AA742404 | <——+ |
| 13 | AA922738 | <———+ |
| 12 | AI091150 | <——+ |
| 11 | AA989195 | <———+ |
| 10 | W69567 | <——+ |
| 9 | AI123218 | <———+ |
| 8 | AI99486 | <——+ |
| 7 | AA576526 | <——+ |
| 6 | W69888 | +———> |
| 5 | T81701 | +——> |
| 4 | H11886 | +——>......+–> |
| 3 | a136-20 | +————————> |
| 2 | a60-a | +—————> |
| 1 | a91 | +———> |
| | POLL | +———*————————————*———> |

Length (bp): 0  300  600  900  1200  1500  1800  2100  2400  2700

*Fig. 1* human POLL mRNA

RT-PCR amplification

Identified splicing variants

*(ORF not disrupted)*

POLL Δ5*   altern. splicing

POLL Δ6    exon skipping

POLL Δ6/7  exon skipping

*(ORF disrupted)*

POLL Δ3-6  exon skipping

POLL Δ3-7  exon skipping

DNA POLYMERASE LAMBDA AND USES THEREOF

CROSS-REFERENCE TO RELATED APPLICATIONS

This application is a national phase entry in the United States under 35 U.S.C. §371 from International Application Number PCT/GB00/03784, filed on Oct. 2, 2000, which claims priority to and benefit of Spanish Application Number P 9902169, filed Oct. 1, 1999.

FIELD OF THE INVENTION

The present invention relates to the identification and isolation of a DNA polymerase and uses of this polymerase. In particular, the present invention describes the nucleotide sequence of the human gene for DNA polymerase lambda (Pol λ), the amino acid sequence of Pol λ, and the amino acid sequence of several isoforms derived from alternative splicing of its mRNA. The association of some of these isoforms with tumour samples makes Pol λ a marker for the diagnosis, prognosis and evolution of tumoral processes.

BACKGROUND OF THE INVENTION

One of the first hypotheses on the existence of DNA repair mechanisms proposed that the DNA present in the germinal cells of multicellular organisms would be protected against damage, and consequently against aging, by virtue of an efficient DNA repair associated to meiosis. On the other hand, somatic cells would be much more vulnerable to DNA damage as they possess a lesser DNA repair capacity. However, it is now known that there are several DNA repair machineries which also act at a somatic level that eliminate most of the damage and alterations occurring at the genome, and that excessive damage or dysfunction of these protective mechanisms could lead to premature aging and cell death, or else favour the proliferation that characterizes tumoral processes.

In mammals there is a clear correlation between the longevity of different species and their capacity to carry out DNA repair. Furthermore, aging can be accelerated by treatments that damage DNA or due to genetic defects at genes involved in DNA repair. In humans, one of the keys in aging is the degeneration of the central nervous system (CNS) and this is related to its extreme sensitivity to genotoxic agents. It is widely accepted that most degenerative diseases, that sometimes show symptoms of premature aging of the CNS, are due to accumulation of DNA damage.

Moreover, fixation of mutations due to DNA repair defects (somatic mutations) can cause cellular transformation. Carcinogenesis is a complex process initiated by a damage in the DNA, followed by the mutation or translocation of a DNA segment, and ending with a phenotypic transformation of the cell. It is widely documented that some normal genes (proto-oncogenes) can become tumoral (oncogenes) by the action of several agents that produce DNA strand breaks. Frequently, these changes directly affect the sequence of the proto-oncogene, that is translocated to another breaking point in a different chromosome. As known in the art, most cells are endowed with DNA repair mechanisms that recognize and eliminate this genomic damage. The absence or dysfunction of these systems would increase the probability of cell transformation. Poly ADP-ribose polymerase (PARP) was one of the first enzymes to be involved in DNA repair of DNA strand breaks. Its activity was shown to be higher in the nuclei of fibroblast transformed by SV40 than in the controls. Similarly, the enzymatic activity of PARP was shown to be higher in leukemic than in normal cells, and the same increase was observed in the mucosa from colorectal cancer patients than in that derived from healthy individuals [Miwa et al., Arch. Biochem. Biophys. 181:313-321 (1977); Burzio et al., Proc. Soc. Exp. Biol. Med. 149:933-938 (1975); Hirai et al., Cancer Res. 43:3441-3446 (1983)]. This work allows one to conclude that the DNA polymerase activity of PARP is increased after DNA damage. Moreover, inhibition of the polymerization activity of PARP by addition of specific drugs produced an increase in genomic DNA damage and in the risk of oncogenic transformation [Harris, Int. J. Radiat. Biol. 48:675-690 (1985)]. These data led to the suggestion to use PARP as a tumoral marker and also as an indicator of the predisposition to develop cancer, see U.S. Pat. No. 5,449,605.

On the other hand, it has been recently demonstrated that the non-hereditary colorectal carcinomas, and about 15% of sporadic gastric tumors, are characterized by the instability of repetitive sequences in the DNA (microsatellites). This phenotype, named mutator phenotype, is accompanied by a several hundred fold increase in spontaneous mutations [Eshleman et al, (1995), Oncogene 10, 33-37; Eshleman et al, (1996), Oncogene 12, 1425-1432], that appears to be due to dysfunction of genes involved in the process of DNA mismatch repair [Hoffman & Cazaux, (1998), Int. J. Oncol. 12, 377-382; Umar & Kunkel, (1996), Eur. J. Biochem. 238, 297-307]. Thus, the basis for a predisposition to colon cancer can based on the existence of a germ line mutation (inherited) in some of those genes (hMSH2, hMLH1, PMS1, PMS2, hMSH3 and hMSH6) required for postreplicative mismatch repair [Prolla et al, (1998), Nature Genetics 18, 276-279]; a second sporadic mutation, that could appear as a consequence of a defective DNA repair, could increase the mutator phenotype if targets the other allele of the same gene, or targets another gene involved in DNA repair (second mutator), allowing the further selection of proliferative variants, and leading to tumour formation. Several mutations have been described in two human genes involved in mismatch repair (hMSH3 and hMSH6), in patients affected by hereditary colon carcinoma, that frequently consist in frameshifts occurring at series of consecutive adenine and cytosine residues [Yamamoto et al, (1998), Cancer Res. 58, 997-1003].

To date, there is no evidence that Pol β participates in the process of "mismatch repair". However, a specific deletion (amino acids 208 to 236), close to the active site, in one of the alleles of Pol β has been found associated to some breast and colorectal carcinomas [Battacharyya & Banerjee, (1997), P.N.A.S. USA 94, 10324-10329]. Furthermore, 83% of the human colon carcinomas show the presence of mutations in the Pol β gene [Wang et al, (1992), Cancer Res. 52, 4824-4827; Dobashi et al, (1995), Hum. Genet. 95, 389-390]. There is also reported evidence on the existence of Pol β mutations associated to bladder carcinoma, but in this case there are also additional mutations associated to tumour suppressor genes as p16 and RB [Matsuzaki et al, (1996), Mol. Carcinog. 15, 38-43]. The attempts to demonstrate the importance of Pol β in tumourogenesis were not successful, since germline deletion of Pol β resulted in a letal phenotype [Gu et al, (1994), Science 265, 103-106].

To date, 10 eukaryotic cellular DNA polymerases have been described (DNA polymerases α, β, γ, δ, ε, ζ, η, θ, ι, and κ). Of these DNA polymerases α, β and ε are involved in DNA replication [Wood & Shivji, (1997), Carcinogenesis 18, 605-610]. Most DNA repair mechanisms have associated DNA synthesis steps to replace the damaged nucleotides, or to bridge the ends of broken DNA. One of the mechanisms frequently used in the cell is "base excision repair" which eliminates slightly modified bases or abasic nucleotides. The DNA synthesizing enzyme involved in this process appears to be Pol β, acting in concert with XRCC1 and DNA ligase III [Dianov & Lindahl, (1994), Nature 362, 709-715; Sobol et al, (1996), Nature 379, 183-186; Nicholl et al, (1997), Biochemistry 36, 7557-7566]. There has been speculation about the existence of an alternative, larger scale process, involving the processivity factor PCNA, and DNA polymerases δ and ε. The elimination of thymidine dimers and bulk adducts in the DNA, carried out in a process named "nucleotide excision repair", appears to involve also DNA polymerases δ or ε. In the same sense, DNA polymerases δ or ε are invoked in catalysing the post-replicative repair of insertion errors (mismatch repair), since this process is normal in Pol β-deficient cells. The expression of Pol β, a house keeping gene, is constant, and is neither stimulated by cell growth nor cell cycle controlled [Zmudzka et al, (1988), Nucleic Acids Res. 16, 9587-9596]. Clearly, since the mismatch repair must be coupled to DNA replication, both processes should be co-regulated. DNA polymerases ζ, η and θ are not appropriate to correct replication errors. On the contrary, their biochemical properties support that these enzymes are involved in the bypass of DNA lessions, an alternative to DNA repair [Lawrence & Hinkle, (1996), Cancer Surv. 28, 21-31; Masutani et al, (1999), Nature 399, 700-704; Sharief et al, (1999), Genomics 1, 90-96].

It therefore remains a problem in the art to identify further DNA polymerases involved in the acquisition of a mutator phenotype. These polymerases may be clinically extremely important for providing the tools for identifying individuals with a predisposition of developing cancer, improve the efficiency of clinic surveillance for an early detection and intervention at early stages [de la Chapelle & Peltomaki, (1995), Annual Rev. Genet. 29, 329-348], and develop novel strategies of therapy based on these targets. It is also possible that some of these DNA polymerases could be involved in neurodegenerative diseases of the central nervous system, since these processes are probably related with a defective or error-prone DNA repair.

SUMMARY OF THE INVENTION

Broadly, the present invention discloses the nucleic acid sequence of the human and murine genes for DNA polymerase lambda (Pol λ), the amino acid sequence of Pol λ, and the amino acid sequence of several isoforms derived from alternative splicing of its mRNA. The association of some of these isoforms with tumoral samples makes Pol λ a potential marker for prognosis, diagnosis and evolution of some tumoral processes. An allelic variant corresponding to a single nucleotide polymorphism located close to the active site and a double mutation close to the polyA that could be related with tumorogenesis are also disclosed. Moreover, the fact that Pol λ is a DNA polymerase with a very low insertion fidelity opens up the possibility that dysregulation of this enzyme could increase the mutation frequency of the genome, both at germinal and somatic cells. Moreover, alteration of the expression of Pol λ could be relevant in pathological processes associated with DNA repair deficiencies, that lead to the appearance of a mutator phenotype.

Accordingly, in a first aspect, the present invention provides isolated DNA polymerase λ (Pol λ) polypeptide comprising the amino acid sequence as set out in SEQ ID No: 4. This is the wild type amino acid sequence of human Pol λ. In other related aspects, the present invention provides isolated polypeptides which are isoforms of human Pol λ, the polypeptides having the amino acid sequences as set out in SEQ ID Nos: 7, 9 and 11.

In a further aspect, the present invention provides isolated DNA polymerase λ (Pol λ) polypeptide comprising the amino acid sequence as set out in SEQ ID No: 1. This is the wild type amino acid sequence of murine Pol λ.

In a further aspect, the present invention provides an isolated polypeptide having greater than 40% amino acid sequence identity with any one of the above Pol λ amino acid sequences. In a further aspect, the present invention provides an isolated polypeptide encoded by nucleic acid capable of hybridising to one of the nucleic acid sequences encoding human or murine Pol λ, or an isoform thereof, under stringent conditions.

In a further aspect, the present invention provides a substance which is a polypeptide which is a sequence variant or allele of any one of the above polypeptides.

In a further aspect, the present invention provides a substance which is a fragment or active portion of one of the above polypeptides.

In a further aspect, the present invention provides isolated nucleic acid molecules encoding one of the above polypeptides. The cDNA sequence of full length human Pol λ is set out in SEQ ID No: 5. The full length murine Pol λ cDNA sequence is provided as SEQ ID No: 1 and the corresponding genomic sequence is set out in SEQ ID No: 3. The nucleic acid sequences of the human isoforms are provided as SEQ ID Nos: 6, 8 and 10.

The present invention also include nucleic molecules having greater than a 90% sequence identity with one of the above nucleic acid sequence. In other embodiments, the present invention relates to nucleic acid sequences which hybridise to the sequence set out in SEQ ID No: 1, 5, 6, 8 or 10, e.g. under stringent conditions as disclosed herein.

In further aspects, the present invention provides an expression vector comprising one of the above nucleic acid operably linked to control sequences to direct its expression, and host cells transformed with the vectors. The present invention also includes a method of producing Pol λ polypeptide, or an isoform, fragment or active portion thereof, comprising culturing the host cells and isolating the polypeptide thus produced.

In a further aspect, the present invention provides an expression vector comprising Pol λ nucleic acid for use in methods of gene therapy.

In a further aspect, the present invention provides a composition comprising a Pol λ nucleic acid molecule as defined herein.

In a further aspect, the present invention provides a composition comprising one or more Pol λ polypeptides as defined above.

In further aspects, the present invention provides the above Pol λ polypeptides or nucleic acid molecules for use in methods of medical treatment.

In a further aspect, the present invention provides the use of a Pol λ polypeptide for screening for candidate compounds which (a) share a Pol λ biological activity or (b) bind to the Pol λ polypeptide or (c) inhibit a biological activity of a Pol λ polypeptide, e.g. to find peptidyl or non-peptidyl mimetics of the Pol λ polypeptides to develop as lead compounds in pharmaceutical research.

In a further aspect, the present invention provides antibodies capable of specifically binding to the above Pol λ polypeptides. These antibodies can be used in assays to detect and quantify the presence of Pol λ polypeptide, in methods of purifying Pol λ polypeptides, and as inhibitors of Pol λ biological activity.

In a further aspect, the present invention method for determining the presence of Pol λ nucleic acid and/or mutations within a nucleic acid sequence in a test sample comprising detecting the hybridization of test sample nucleic acid to a nucleic acid probe based on the Pol λ nucleic acid sequences provided herein.

In a further aspect, the present invention provides a method of amplifying a nucleic acid test sample comprising priming a nucleic acid polymerase reaction with nucleic acid encoding a Pol λ polypeptide as defined above. The present invention also provides the use of the above nucleic acid in the search for mutations in the Pol λ genes, e.g. using techniques such as single stranded conformation polymorphism (SSCP).

These and other aspects of the present invention are described in more detail below. By way of example, embodiments of the present invention will now be described in more detail with reference to the accompanying figures.

BRIEF DESCRIPTION OF THE FIGURES

FIG. 1: Scheme of the procedure for cloning human POLL gene. The different cloning steps are represented by the alignment of the different cDNA fragments obtained. Fragments 1-3 were obtained from placenta. Fragments 4 to 14 represent sequences obtained from the dbEST/GenBank database, indicated with their accession numbers. The EST identified as H11886 presented an internal deletion. Asterisks indicate the relative position of the initiation and termination codons.

DETAILED DESCRIPTION

Figure 2:
FIG. 2: RT-PCR amplification of the mRNA corresponding to the human POLL gene. Specific primers were used to selectively amplify the portion of the mRNA that shows differences in splicing. M, size marker. a) Amplification of samples proceeding from fetal and adult brain. b) Amplification of samples obtained from cell lines and human tumours. c) Schematic representation of the splicing variants of the Pol λ mRNA identified by RT-PCR amplification.
Figure 2:
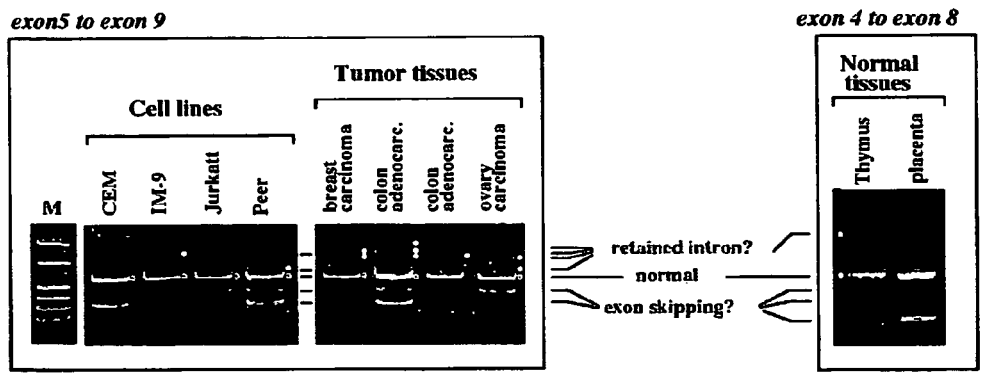
Figure 2:
Figure 2:
Figure 2:
Figure 2:
Figure 2:

Cloning, Expression and Characterisation of Pol λ

It should be noted that in the priority application, Pol λ was referred to as "Pol κ", and that for consistency with nomenclature adopted since the priority date, the polymerase of the present invention is referred to in the art and herein as "Pol λ" or "POLL" for the gene encoding it. In the present invention "Pol λ biological activity" refers to the activity of these polypeptides as DNA polymerases.

The novel DNA polymerase (Pol λ) of the present invention was identified by similarity searches using the amino acid sequence of African swine fever virus (ASFV) Pol X as a probe [Oliveros et al, (1997), J. Biol. Chem. 272, 30899-30911]. This viral DNA polymerase belongs to the family of Pol β-like DNA polymerases, named Pol X family. A first indication on the existence of this DNA polymerase was obtained from the finding of a genomic DNA fragment, whose translation showed a low, but significant similarity with Pol X family members, particularly in the most conserved regions of the catalytic core. This DNA fragment (clone CIT282B21: gb AC003694), which maps at chromosome 19 in mouse (*Mus musculus*) was obtained from the HTGS (High Throughput Genome Sequences) database, that contained a further 1849 DNA fragments when Pol λ was identified. After carrying out further similarity searches in the EST (dbEST/GenBank) database, the first evidence of expression of this potential DNA polymerase was obtained. Among the ESTs corresponding to murine Pol λ, one potentially encoding its complete cDNA was identified. This EST (clone 1162340; AA692052) was obtained from the IMAGE Consortium, at the LLNL (Lawrence Livermore National Laboratory), and was sequenced.

The resulting sequence corresponded to an open reading of 2277 nucleotides, coding for 573 amino acid protein. Additional sequence (59 nucleotides) corresponding to the 5'-end of the cDNA was obtained by RACE 5', starting from mRNA from murine testis.

Thus, the cDNA corresponding to the Pol λ gene (POLL) consists of a total of 2336 by (SEQ ID No: 1), with a 5'-untranslated region of 83 by (nucleotides 1 to 83), a coding region of 1722 by (nucleotides 84 to 1805), and a 3'-untranslated region of 531 by (nucleotides 1806-2336). The derived protein, murine Pol λ, has 573 amino acids (SEQ ID No: 1 or 2).

The comparison among the cDNA sequence and that of de genomic clone AC003694 allowed to define the exon-intron organization of the murine POLL gene (see SEQ ID No: 3). This gene spans about 8 kilobases and maps to mouse chromosome 19. This genomic sequence contains several microsatellites located in several introns: (A) 12 in positions 1079 ... 1156 y 3088.3138; (CA) 32 in positions 3779 ... 3823 y 4914 ... 4982; (GCCTCT) 40 in positions 4017 ... 4272; "AT-rich" in positions 1565.1589, and (TGG) n in positions 3874 ... 3901. The mRNA transcript is made of 9 exons. The C-terminal segment encompassing amino acid residues 247 to 573, shows a high similarity with members of the DNA polymerase X family [Ito & Braithwaite, (1991), Nucleic Acids Res. 19, 4045-4057]. Members of this family are: Pol β, the only eukaryotic DNA polymeras that has been selectively involved in DNA repair; AFSV PolX, involved in viral DNA repair; terminal deoxynucleotidyl transferase (TdT), involved in the generation of antigen receptor variability. Murine Pol λ has a 32% amino acid sequence identity with Pol β, in the portion that can be aligned (amino acid residues 240 to 573). In spite that this comparatively low value, it was possible to model the structure of this DNA polymerase using the structure of Pol β as a template, and preserving all the structured elements (α-helices, turns and beta-strands), and the tertiary folding in the four different subdomains described in Pol β: "8 kDa", "fingers", "palm" and "thumb". In summary, both the primary sequence and the structural predictions supported the hypothesis that the newly identified protein was a novel DNA polymerase, that was named Pol λ, and that forms part of the present invention.

On the other hand, the first 239 amino acids of Pol λ, which have no counterpart in Pol β, contain a BRCT domain (amino acid residues 34 to 125). The BRCT domain has been recently described to be present in single of multiple copies either in the N-terminus or in the C-terminus of proteins directly involved in DNA repair or involved in cell-cycle control checkpoints in response to DNA damage. It is worth noting that the BRCT domain, initially identified in the BRCA1 protein, is also present in other proteins involved in tumorogenesis as the ECT2 oncogene, protein p53BP, and human RB. Connecting the BRCT domain with the catalytic domain (Pol β-like), there is a region enriched in the amino acid residues Ser and Pro (residues 126 to 239), that has no similarity with known proteins, and that could serve a flexible hinge to couple the DNA polymerase activity to the various interactions, protein:protein and protein:DNA, that could be required during the process of DNA repair.

In a next step, we expressed Pol λ in transformed *E. coli* cells, using a vector that contains the complete sequence of the mouse cDNA, allowing us to obtain high amounts of purified recombinant Pol λ, and to obtain specific polyclonal antibodies, the expression of the protein and the generation of antibodies capable of specifically binding to Pol λ protein being part of the present invention (see further below). The present invention thus includes, inter alia, Pol λ gene sequence; Pol λ cDNA sequence; Pol λ amino acid sequence; vector comprising Pol λ nucleic acid, transformed cells expressing Pol λ; and monoclonal and polyclonal antibodies that are specific for Pol λ.

The intrinsic DNA polymerase activity associated to Pol λ can be demonstrated using an in situ DNA polymerase analysis in SDS-polyacrylamide gels [Blanco & Salas, (1984), P.N.A.S. USA 81, 5325-5329], and crude *E. coli* extracts in which the expression of Pol λ had been induced. The DNA polymerase activity of this novel enzyme, that is the basis for the application of this novel DNA polymerase as a tool in molecular biology, forms part of the present invention.

The availability of 8 kilobases of Pol λ genomic sequence allowed us to identify and determine of sequence of the human cDNA for Pol λ (SEQ ID No: 4), together with the amino acid sequence of the encoded protein (SEQ ID No: 5), both forming part of the present invention. The murine and human homologues of Pol λ share more than 80% of amino acid identity, that reaches the 90% in the most conserved regions, and 57% in the Ser/Pro-rich flexible hinge. The identification of the human homologue of Pol λ was initially based in similarity searches of the dbEST/GeneBank database. Among a total of 1,323,073 non-redundant sequences, 11 entries had significant similarity with mouse Pol λ. These 11 DNA fragments corresponded to fetal tissues (heart, liver and spleen; 5 cases), to infant brain (2 cases), to germinal center-B cells (1 case), and to some tumoral samples (colon, breast and germ cells) in the three remaining cases. Again, it seems to be significant that all the ESTs corresponding to Pol λ originated from tissues (either normal or pathological) with a high degree of proliferation, and therefore demanding correspondingly high amounts of enzymes involved in DNA repair.

Expression of Pol λ mRNA is highly abundant in testis (both in human and mouse), although there is a basal expression in most tissues. Therefore, the expression data suggest that the normal or predominant function of this DNA polymerase could be to repair the DNA breaks occurring at somatic cells, and to participate in meiosis, a process that is triggered by programmed double-strand breaks in the DNA of germinal cells. An interesting possibility, derived form the elevated error-proneness observed during in vitro DNA polymerization assays, is that the DNA synthesis catalysed by Pol λ could be mutagenic, introducing mutations in the DNA that could contribute the background of variability required for genome evolution.

The biochemical properties of this novel DNA polymerase are the basis for its potential use as a novel DNA modification enzyme in molecular biology, and constitute a further aspect of the present invention.

Unlike its mouse homologue, human Pol λ presents a significant number of splicing variants that can be detected in normal tissues, tumoral tissues and cell lines. One of the ESTs corresponding to human Pol λ (H11886), obtained from infant brain, seemed to be the consequence of an alternative splicing event occurring at the Pol λ pre-mRNA, resulting in the fusion of exons 5 and 8, and the consequent loss of exons 6 and 7 (exon skipping). RT-PCR amplification using primers corresponding to these exons showed the existence of two main splicing variants that were present in fetal cDNA, but not in adult cDNA, one of them corresponding to the omission of exon 6 (D6), and the other corresponding to the simultaneous omission of exons 6 and 7 (D6+7) (FIG. 2a). Moreover, the same splicing variants and others of larger size were observed by amplification of cDNA derived from tumoral cell lines and biological samples derived from human tumours, as ovary carcinoma, colon adenocarcinoma and breast cancer) (FIG. 2b). A total of five splice variants have been characterised. Three of them maintain the original reading frame and therefore the resulting protein is not truncated. According to the exon-intron organization of the murine gene for Pol λ, one of the non-truncated variants corresponds to the omission of exon 6, and other to the simultaneous omission of exons 6 and 7. The third non-truncated variant is produced by the use of a cryptic splicing site present inside exon 5 of the human sequence. These variants, that are the most abundantly expressed are named and detailed as follows:

hPOLλdelta5 (clone type a60b4) (SEQ ID NO: 39 for nucleic acids and SEQ ID NO: 40 for amino acids): has a deletion of nucleotides 987-1262 in the cDNA; it loses 87% of exon 5, deleting 277 bases; the sequence in SEQ ID NO: 6 shows the junction of such deletion at position 607; the junction where the deletion occurs is also shown in the amino acid sequence of SEQ ID No: 7.

hPOLλdelta6 (clone type a31m) (SEQ ID NO: 41 for nucleic acids and SEQ ID NO: 42 for amino acids): has a deletion of nucleotides 1263-1436 in the cDNA; it completely loses exon 6, 175 bases; the sequence in SEQ ID NO: 8 shows the junction of such deletion at position 26; the junction where the deletion occurs is also shown in the amino acid sequence of SEQ ID No: 9.

hPOLλdelta6+7 (clone type a31c) (SEQ ID NO: 43 for nucleic acids and SEQ ID NO: 44 for amino acids): has a deletion of nucleotides 1263-1565; it completely loses exons 6 and 7, 304 bases; the sequence in SEQ ID NO: 10 shows the junction of such deletion at position 26; the junction where the deletion occurs is also shown in the amino acid sequence of SEQ ID No: 11.

The other two splicing variants are less interesting "a priori", since they produce an early truncation of the open reading frame. To carry out a selective expression analysis of each splicing variant of Pol λ in normal versus tumoral tissues, splicing-specific pair of PCR-primers were designed. These primers, able to amplify selectively each splicing variant (see Example 2), serve to identify their presence and relative amount in different biological samples. Methods of assessing the relative amounts of the variants also forms part of the present invention.

Figure 3:
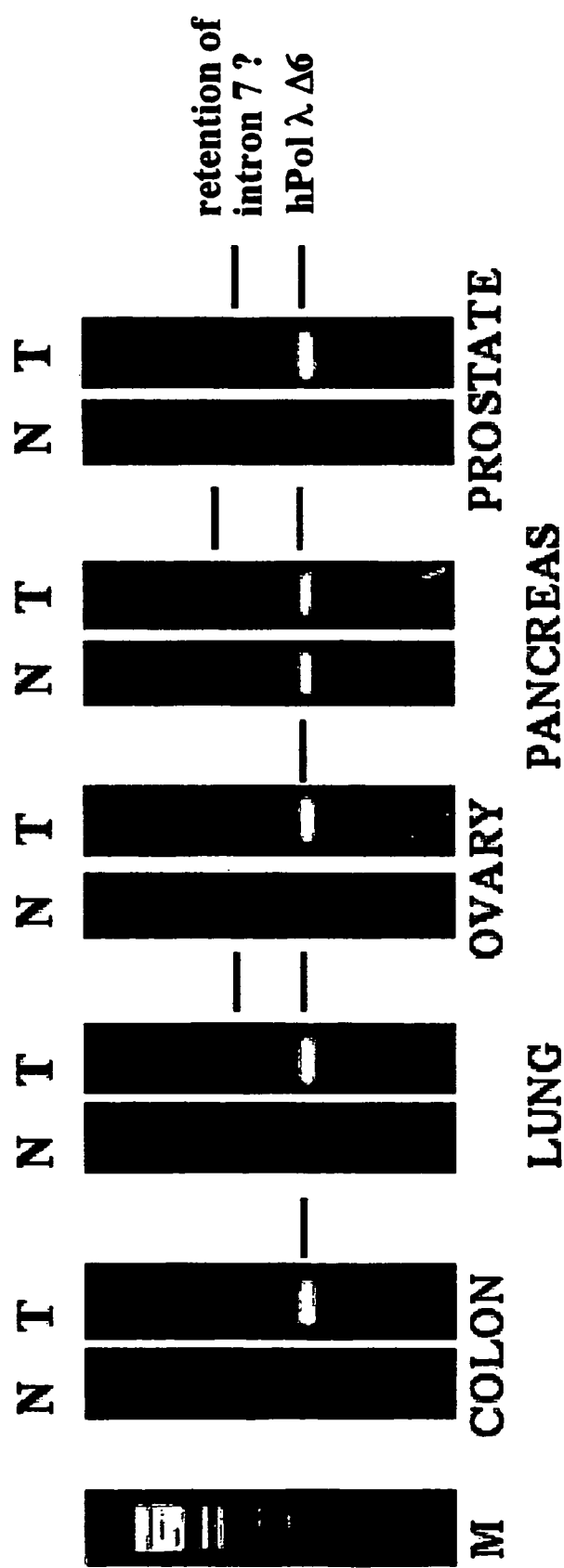
FIG. 3: RT-PCR amplification of the splicing variant D6 corresponding to Pol λ mRNA. The reaction was carried out using splicing specific primers (described in the text) in order to amplify selectively the splicing variant D6, both in normal and tumoral tissues. M, size markers; N, normal tissue T, tumoral tissue; ?, uncharacterized amplification product.

Thus, it was observed that variant D6, absent in adult brain but present in fetal brain, was also absent in most of the normal tissues analysed (with the exception of pancreas), but on the contrary it can be detected in primary tumours of the corresponding tissues (FIG. 3).

Figure 4:
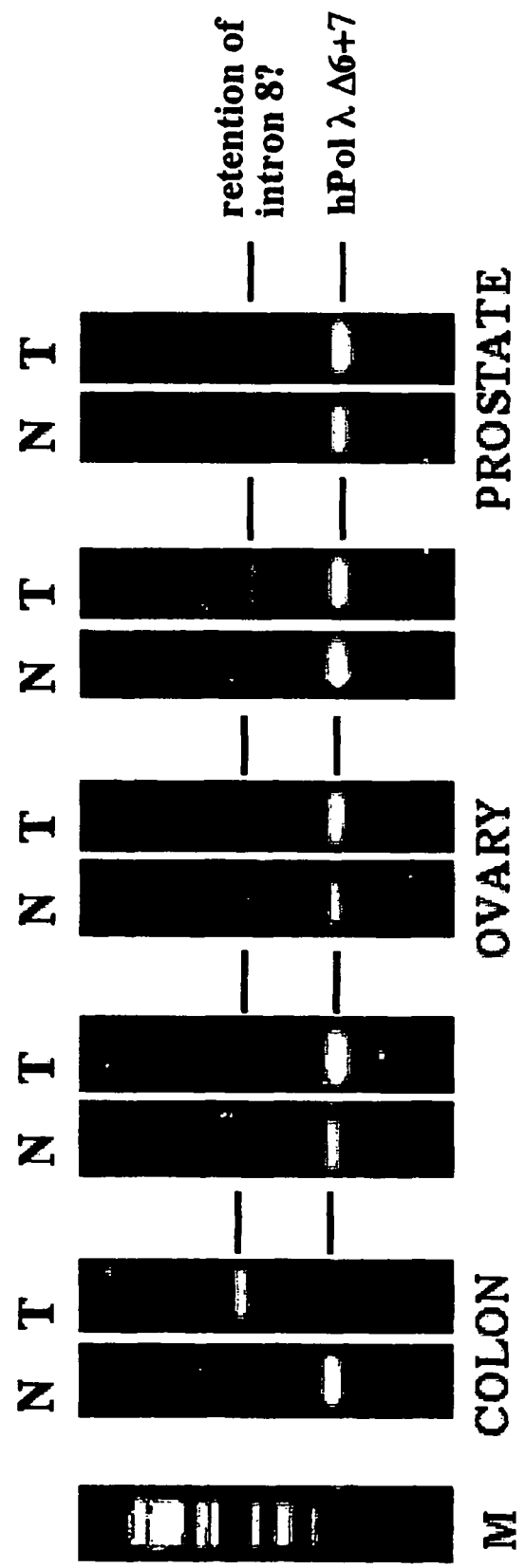
FIG. 4: RT-PCR amplification of the splicing variant D6+7 corresponding to Pol λ mRNA. The reaction was carried out using splicing specific primers (described in the text) in order to amplify selectively the splicing variant D6+7, both in normal and tumoral tissues. M, size markers; N, normal tissue T, tumoral tissue; ?, uncharacterized amplification product.

The selective amplification of variant D6+7 showed that, as it occurs in fetal brain, but not in adult brain, this variant is present in most of the normal tissues, and is present in similar or slightly increased amounts in the corresponding tumours (FIG. 4). Interestingly, a new variant was observed in adult brain, that corresponds to the additional retention of intron 8. This novel isoform is only detectable in normal pancreas and it appears in tumour samples corresponding to tissues in which is normally absent. The most significant example is colon, in which there is a complete substitution of isoforms when comparing a normal versus tumoral tissue.

At the amino acid level, deletion D6+7 produces the loss of part of the subdomain 8 kDa, and the complete loss of the "fingers" subdomain, with the consequent loss of two important DNA binding domains of the enzyme, the so called "helix-hairpin-helix motifs [Doherty et al, (1996), Nucleic Acids Res. 24, 2488-2497]. The three variants D5, D6 and D6+7 do not give rise to the truncation of the protein, and maintain the subdomains that form the catalytic site. Therefore, it is likely that they represent functional versions of the polymerase, since its polymerization domain, reduced to the minimal core, is very similar to that of ASFV Pol X, whose functionality in DNA repair has been recently demonstrated [Oliveros et al, (1997), J. Biol. Chem. 272, 30899-30911]. As described earlier, the acquisition of a mutator phenotype that leads to tumoral transformation can be primarily due to alterations in DNA repair mechanisms. In the present invention a novel human DNA polymerase is described, that can act either as a tumour suppressor, by preventing DNA damage accumulation, or directly contributing to tumorogenesis by introducing mutations in the DNA as a side effect of its participation in an error-prone DNA repair mechanism. The latter hypothesis is supported by the low insertion fidelity of Pol λ when assayed in vitro on undamaged DNA templates.

Moreover, specific isoforms of Pol λ could be functional, displaying a mutator phenotype that could contribute to tumorogenesis. This idea is supported by the specific presence, identified by selective PCR amplification, of some of these variants in tumoral samples. Therefore, Pol λ and its isoforms can be considered as potential tumoral markers in humans, with the consequent advantages both in prognosis and diagnosis of these malignancies. On the other hand, the expression of each of these isoforms will allow to obtain the purified polypeptides to generate specific antibodies that could serve to develop more specific methods of identification and diagnosis, and which form part of the present invention. Moreover, the knowledge of the cDNA sequence corresponding to each isoform allows the generation of specific probes for identification and diagnosis, that form part of the present invention.

An attractive hypothesis proposed herein is that the DNA polymerase variants produced by alternative splicing represent "mutator" DNA polymerases that could act as dominant error-prone versions, able to interfere and/or alter the normal levels of DNA repair, inducing cellular transformation of those cells in which these variants are expressed, or favouring other processes related to a deficient DNA repair capacity, as it occurs in neurodegenerative diseases and aging.

Our knowledge of the POLL gene (coding for Pol λ) and its expression variants allows to develop strategies to test the function of these enzymes either in the maintenance of the normal cellular physiology, or in the promotion of cellular transformation. These strategies are based on the transformation of normal cells with different combinations of plasmids overexpressing specific variants of Pol λ, to study the effect of the expressed isoforms on the cellular phenotype.

The identification of a particular Pol λ isoform (or a combination of isoforms) able to induce pathologic phenotype, will provide with a novel target to interfere those processes related to defects in DNA repair (neurodegenerative diseases, cancer), and form a further aspect of the present invention. On the other hand, the availability of Pol λ-transformed cells showing a tumoral phenotype will allow the development of specific inhibitors that could serve as therapeutic compounds.

Moreover, the disclosure provided by the present invention of Pol λ will serve to generate a model of Pol λ-deficiency in mouse (knock out), in which this gene can be selectively deleted [Schawartzberg et al, (1989), Science 246, 799-803], that will be very useful to study the induction of pathologies, and to identify novel therapeutic compounds.

In similarity searches carried out in the dbEST/GeneBank to look for those ESTs corresponding to the human Pol λ that contain information corresponding to the 3'-end of the mRNA, a number of ESTs were found. The existing ESTs had the identification numbers: AI970471; AA576526; AI199486; AI123218; AA989195; AI091150; AA922738; W69567; AI560660; AI612820; AA927738; AA742404; R16877; H11524; T81488; R71372; AI538103; AA807380; AA991853; AA468875. Among these 20 sequences, 9 correspond to normal tissues, whereas the remaining 11 sequences correspond to tumours from several origins.

The nucleotide sequence alignment of these 20 ESTs showed the existence of a double-mutation in 7 cases. This double mutation occurred in all cases in nucleotides T2576 and G2579, separated only by two nucleotides (SEQ ID No: 12). Also in all cases, these two nucleotides were identically substituted: T2576->C y G2579->T. None of the 7 mutated sequences correspond to the ESTs obtained from normal tissues (a total of 9 ESTs), whereas all of them correspond to ESTs obtained from tumours (7 sequences mutated out of 11 samples). The mutated ESTs had the identification number:

AI970471; AA576526; AA922738; AI612820; AA927738; AI538103; AA468875. Three of the latter derive from germ cell tumours, one from ovary tumour, one from uterus adenocarcinoma, and the two remaining from breast and colon carcinomas. In some nucleic acid embodiments of the invention, these ESTs are excluded from the present invention.

Therefore, and in the absence of a more exhaustive and significant statistic analysis, the incidence of this double mutation in tumoral samples from different nature reaches the surprisingly high value of 64%. The most reasonable interpretation is that this double-mutation corresponds to an allelic variant, with a high linkage or probability to develop tumours. This correlation could be the consequence of an altered stability of the Pol λ mRNA in those individuals harbouring the allelic variant, that could imply a deficiency in Pol λ function, and therefore, in the capacity of the cell to carry out specific processes of DNA repair. The identification of this double-mutation in human biological samples by different techniques of molecular biology, as in situ hybridization or PCR, will allow the early diagnosis of the individuals harbouring the mutation, helping to define appropriate control and surveillance of the population at a risk.

Using a panel of somatic cell hybrids (murine/human), the human Pol λ gene was initially mapped at chromosome 10. By using radiation hybrids, mapping was refined to position 10q24. This region presents a very high frequency of molecular alterations, mainly deletions and rearrangements.

The existence of more than 7 breaking points in a region of only 9 kilobases suggests the presence of a neighbouring gene whose activation would confer selective advantages. The same region, 10q24, is involved in translocations in T-cell acute lymphoblastic leukemia [Park et al, (1992), Genes Chromosomes Cancer 4, 32-40], and is frequently deleted in a high proportion of prostate tumours [Ford et al, (1998), Cancer Genet. Cytogenet. 102, 6-11], and human glyoma [Chemova et al, (1998), Cancer Genet. Cytogenet. 105, 60-68]. Finally, it is worth noting that Pol λ has a significant level of expression in human brain, particularly in neurons. Moreover, the pattern of isoforms differs when comparing different developmental stages (fetal versus adult) (FIG. 2a). Assuming a role of Pol λ in DNA repair, and the fact that a DNA repair deficiency could be the basis for neurodegenerative diseases, it can be speculated that sporadic or inherited alterations of the novel polymerase described in the present invention can be critical for the appearance and development of the disease. Therefore, a wide knowledge of the function and regulation of Pol λ will open new avenues for diagnosis and therapy of these pathologies.

Pol λ Nucleic Acid

"Pol λ nucleic acid" includes a nucleic acid molecule which has a nucleotide sequence encoding a polypeptide which includes the amino acid sequence shown in SEQ ID No: 1 or 4. The Pol λ coding sequence may be the full length sequence shown in SEQ ID No: 1 or 4, a complementary nucleic acid sequence, or it may be a mutant, derivative or allele of these sequences. The sequence may differ from that shown by a change which is one or more of addition, insertion, deletion and substitution of one or more nucleotides of the sequence shown. Changes to a nucleotide sequence may result in an amino acid change at the protein level, or not, as determined by the genetic code. Thus, nucleic acid according to the present invention may include a sequence different from the sequence shown in SEQ ID No: 1 or 4 yet encode a polypeptide with the same amino acid sequence.

On the other hand, the encoded polypeptide may comprise an amino acid sequence which differs by one or more amino acid residues from the amino acid sequence shown in SEQ ID No: 1 or 4. Nucleic acid encoding a polypeptide which is an amino acid sequence mutant, variant, derivative or allele of the sequence shown in SEQ ID No: 1 or 4 is further provided by the present invention. Such polypeptides are discussed below. Nucleic acid encoding such a polypeptide preferably have at least 40% sequence identity with the coding sequence shown in SEQ ID No: 1 or 4, more preferably at least 80% sequence identity, more preferably at least 90% sequence identity, more preferably at least 95% sequence identity, and most preferably at least 98% sequence identity.

The present invention also includes fragments of the Pol λ nucleic acid sequences described herein, the fragments preferably being at least 60, 120, 180, 240, or 480 nucleotides in length.

Generally, nucleic acid according to the present invention is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, cDNA or RNA. Where nucleic acid according to the invention includes RNA, reference to the sequence shown should be construed as reference to the RNA equivalent, with U substituted for T.

Nucleic acid sequences encoding all or part of the POLL gene and/or its regulatory elements can be readily prepared by the skilled person using the information and references contained herein and techniques known in the art (for example, see Sambrook, Fritsch and Maniatis, "Molecular Cloning, A Laboratory Manual, Cold Spring Harbor Laboratory Press, 1989, and Ausubel et al, Short Protocols in Molecular Biology, John Wiley and Sons, 1992). These techniques include (i) the use of the polymerase chain reaction (PCR) to amplify samples of such nucleic acid, e.g. from genomic sources, (ii) chemical synthesis, or (iii) amplification in E. coli. Modifications to the Pol λ sequences can be made, e.g. using site directed mutagenesis, to provide expression of modified Pol λ polypeptide or to take account of codon preference in the host cells used to express the nucleic acid.

In order to obtain expression of the Pol λ nucleic acid sequences, the sequences can be incorporated in a vector having control sequences operably linked to the Pol λ nucleic acid to control its expression. The vectors may include other sequences such as promoters or enhancers to drive the expression of the inserted nucleic acid, nucleic acid sequences so that the Pol λ polypeptide is produced as a fusion and/or nucleic acid encoding secretion signals so that the polypeptide produced in the host cell is secreted from the cell. Pol λ polypeptide can then be obtained by transforming the vectors into host cells in which the vector is functional, culturing the host cells so that the Pol λ polypeptide is produced and recovering the Pol λ polypeptide from the host cells or the surrounding medium. Prokaryotic and eukaryotic cells are used for this purpose in the art, including strains of E. coli, yeast, and eukaryotic cells such as COS or CHO cells. The choice of host cell can be used to control the properties of the Pol λ polypeptide expressed in those cells, e.g. controlling where the polypeptide is deposited in the host cells or affecting properties such as its glycosylation and phosphorylation.

PCR techniques for the amplification of nucleic acid are described in U.S. Pat. No. 4,683,195. In general, such techniques require that sequence information from the ends of the target sequence is known to allow suitable forward and reverse oligonucleotide primers to be designed to be identical or similar to the polynucleotide sequence that is the target for the amplification. PCR comprises steps of denaturation of template nucleic acid (if double-stranded), annealing of primer to target, and polymerisation. The nucleic acid probed or used as template in the amplification reaction may be genomic DNA, cDNA or RNA. PCR can be used to amplify specific sequences from genomic DNA, specific RNA sequences and cDNA transcribed from mRNA, bacteriophage or plasmid sequences. The Pol λ nucleic acid sequences provided herein readily allow the skilled person to design PCR primers. References for the general use of PCR techniques include Mullis et al, Cold Spring Harbor Symp. Quant. Biol., 51:263, (1987), Ehrlich (ed), PCR Technology, Stockton Press, NY, 1989, Ehrlich et al, Science, 252:1643-1650, (1991), "PCR protocols; A Guide to Methods and Applications", Eds. Innis et al, Academic Press, New York, (1990).

The nucleic acid sequences provided herein are useful for identifying nucleic acid of interest (and which may be according to the present invention) in a test sample. The present invention provides a method of obtaining nucleic acid of interest, the method including hybridising a probe sharing all or part of the sequence provided herein, or a complementary sequence, to the target nucleic acid.

Hybridization is generally followed by identification of successful hybridization and isolation of nucleic acid which has hybridized to the probe, which may involve one or more steps of PCR.

Nucleic acid according to the present invention is obtainable using one or more oligonucleotide probes or primers designed to hybridize with one or more fragments of the nucleic acid sequence shown herein, particularly fragments of relatively rare sequence, based on codon usage or statistical analysis. A primer designed to hybridize with a fragment of the nucleic acid sequence, shown in the above figures may be used in conjunction with one or more oligonucleotides designed to hybridize to a sequence in a cloning vector within which target nucleic acid has been cloned, or in so-called "RACE" (rapid amplification of cDNA ends) in which cDNA's in a library are ligated to an oligonucleotide linker and PCR is performed using a primer which hybridizes with the sequence shown herein and a primer which hybridizes to the oligonucleotide linker.

Such oligonucleotide probes or primers, as well as the full-length sequence (and mutants, alleles, variants and derivatives) are also useful in screening a test sample containing nucleic acid for the presence of alleles, mutants and variants, especially those that lead to the production of inactive or dysfunctional forms of Pol λ protein, the probes hybridizing with a target sequence from a sample obtained from the individual being tested. The conditions of the hybridization can be controlled to minimise non-specific binding, and preferably stringent to moderately stringent hybridization conditions are preferred. The skilled person is readily able to design such probes, label them and devise suitable conditions for the hybridization reactions, assisted by textbooks such as Sambrook et al (1989) and Ausubel et al (1992).

As well as determining the presence of polymorphisms or mutations in the Pol λ sequence, the probes may also be used to determine whether mRNA encoding Pol λ is present in a cell or tissue. An example of polymorphism is the single nucleotide polymorphism at position 1389, discussed in detail in Example 5.

Nucleic acid isolated and/or purified from one or more cells (e.g. human) or a nucleic acid library derived from nucleic acid isolated and/or purified from cells (e.g. a cDNA library derived from mRNA isolated from the cells), may be probed under conditions for selective hybridization and/or subjected to a specific nucleic acid amplification reaction such as the polymerase chain reaction (PCR).

In the context of cloning, it may be necessary for one or more gene fragments to be ligated to generate a full-length coding sequence. Also, where a full-length encoding nucleic acid molecule has not been obtained, a smaller molecule representing part of the full molecule, may be used to obtain full-length clones. Inserts may be prepared from partial cDNA clones and used to screen cDNA libraries. The full-length clones isolated may be subcloned into expression vectors and activity assayed by transfection into suitable host cells, e.g. with a reporter plasmid.

A method may include hybridization of one or more (e.g. two) probes or primers to target nucleic acid. Where the nucleic acid is double-stranded DNA, hybridization will generally be preceded by denaturation to produce single-stranded DNA. The hybridization may be as part of a PCR procedure, or as part of a probing procedure not involving PCR. An example procedure would be a combination of PCR and low stringency hybridization. A screening procedure, chosen from the many available to those skilled in the art, is used to identify successful hybridization events and isolated hybridized nucleic acid.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RNAse cleavage and allele specific oligonucleotide probing.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridized to the DNA fragments on the filter and binding determined. DNA for probing may be prepared from RNA preparations from cells.

Preliminary experiments may be performed by hybridizing under low stringency conditions various probes to Southern blots of DNA digested with restriction enzymes. Suitable conditions would be achieved when a large number of hybridizing fragments were obtained while the background hybridization was low. Using these conditions, nucleic acid libraries, e.g. cDNA libraries representative of expressed sequences, may be searched.

Those skilled in the art are well able to employ suitable conditions of the desired stringency for selective hybridization, taking into account factors such as oligonucleotide length and base composition, temperature and so on.

On the basis of amino acid sequence information, oligonucleotide probes or primers may be designed, taking into account the degeneracy of the genetic code, and where appropriate, codon usage of the organism from the candidate nucleic acid is derived. An oligonucleotide for use in nucleic acid amplification may have about 10 or fewer codons (e.g. 6, 7 or 8), i.e. be about 30 or fewer nucleotides in length (e.g. 18, 21 or 24). Generally specific primers are upwards of 14 nucleotides in length, but not more than 18-20. Those skilled in the art are well versed in the design of primers for use processes such as PCR.

A further aspect of the present invention provides an oligonucleotide or polynucleotide fragment of the one of the nucleotide sequence disclosed herein, or a complementary sequence, in particular for use in a method of obtaining and/or screening nucleic acid. The sequences referred to above may be modified by addition, substitution, insertion or deletion of one or more nucleotides, but preferably without abolition of ability to hybridize selectively with nucleic acid with the sequence shown herein, that is wherein the degree of sequence identity of the oligonucleotide or polynucleotide with one of the sequences given is sufficiently high.

In some preferred embodiments, oligonucleotides according to the present invention that are fragments of any of the nucleic acid sequences provided herein, or complementary sequences thereof, are at least about 10 nucleotides in length, more preferably at least about 15 nucleotides in length, more preferably at least about 20 nucleotides in length. Such fragments themselves individually represent aspects of the present invention. Fragments and other oligonucleotides may be used as primers or probes as discussed but may also be generated (e.g. by PCR) in methods concerned with determining the presence of Pol λ nucleic acid in a test sample.

Nucleic acid according to the present invention may be used in methods of gene therapy, for instance in treatment of individuals with the aim of preventing or curing (wholly or partially) the above mentioned conditions. This too is discussed below.

A convenient way of producing a polypeptide according to the present invention is to express nucleic acid encoding it, by use of the nucleic acid in an expression system. The use of expression systems has reached an advanced degree of sophistication.

Accordingly, the present invention also encompasses a method of making a polypeptide (as disclosed), the method including expression from nucleic acid encoding the polypeptide (generally nucleic acid according to the invention). This may conveniently be achieved by growing a host cell in culture, containing such a vector, under appropriate conditions which cause or allow expression of the polypeptide. Polypeptides may also be expressed in in vitro systems, such as reticulocyte lysate. Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Thus, a further aspect of the present invention provides a host cell containing nucleic acid as disclosed herein. The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell.

A still further aspect provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

A host cell containing nucleic acid according to the present invention, e.g. as a result of introduction of the nucleic acid into the cell or into an ancestor of the cell and/or genetic alteration of the sequence endogenous to the cell or ancestor (which introduction or alteration may take place in vivo or ex vivo), may be comprised (e.g. in the soma) within an organism which is an animal, particularly a mammal, which may be human or non-human, such as rabbit, guinea pig, rat, mouse or other rodent, cat, dog, pig, sheep, goat, cattle or horse, or which is a bird, such as a chicken. Genetically modified or transgenic animals or birds comprising such a cell are also provided as further aspects of the present invention.

This may have a therapeutic aim. (Gene therapy is discussed below.) The presence of a mutant, allele or variant sequence within cells of an organism, particularly when in place of a homologous endogenous sequence, may allow the organism to be used as a model in testing and/or studying the role of the Pol λ gene or substances which modulate activity of the encoded polypeptide in vitro.

Instead of or as well as being used for the production of a polypeptide encoded by a transgene, host cells may be used as a nucleic acid factory to replicate the nucleic acid of interest in order to generate large amounts of it. Multiple copies of nucleic acid of interest may be made within a cell when coupled to an amplifiable gene such as DHFR. Host cells transformed with nucleic acid of interest, or which are descended from host cells into which nucleic acid was introduced, may be cultured under suitable conditions, e.g. in a fermenter, taken from the culture and subjected to processing to purify the nucleic acid. Following purification, the nucleic acid or one or more fragments thereof may be used as desired, for instance in a diagnostic or prognostic assay as discussed elsewhere herein.

Pol λ Polpeptides

The skilled person can use the techniques described herein and others well known in the art to produce large amounts of the Pol λ polypeptides, or fragments or active portions thereof, for use as pharmaceuticals, in the developments of drugs and for further study into its properties and role in vivo.

Thus, a further aspect of the present invention provides a polypeptide which has the amino acid sequence shown in SEQ ID No: 1 or 4, which may be in isolated and/or purified form, free or substantially free of material with which it is naturally associated, such as other polypeptides or such as human polypeptides other than Pol λ polypeptide or (for example if produced by expression in a prokaryotic cell) lacking in native glycosylation, e.g. unglycosylated.

Polypeptides which are amino acid sequence variants, alleles, derivatives or isoforms are also provided by the present invention. A polypeptide which is a variant, allele, derivative or isoform may have an amino acid sequence which differs from that provided herein by one or more of addition, substitution, deletion and insertion of one or more amino acids. Preferred polypeptides have Pol λ polymerase function, as defined above.

Preferably, a polypeptide which is an amino acid sequence variant, allele, derivative or mutant of the amino acid sequence shown in SEQ ID No: 1 or 4 has at least 40% sequence identity to one of those sequences, more preferably at least 50% sequence identity, more preferably at least 60% sequence identity, more preferably at least 70% sequence identity, more preferably at least 80% sequence identity, more preferably at least 90% sequence identity, and most preferably at least 95% sequence identity to the sequences of SEQ ID Nos: 1 or 4.

The skilled person can readily make sequence comparisons and determine identity using techniques well known in the art, e.g. using the GCG program which is available from Genetics Computer Group, Oxford Molecular Group, Madison, Wis., USA, Version 9.1. Particular amino acid sequence variants may differ from those shown in SEQ ID Nos: 1 or 4 by insertion, addition, substitution or deletion of 1 amino acid, 2, 3, 4, 5-10, 10-20 20-30, 30-50, 50-100, 100-150, or more than 150 amino acids.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al, Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 760 mM sodium chloride, 75 mM sodium citrate at 42° C.; or (3) employ 50% formamide, 5×SSC (0.75 M NaCl, 0.075 M sodium citrate), 50 mM sodium phosphate (pH 6 8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Percent (%) amino acid sequence identity" with respect to the Pol λ polypeptide sequences identified herein is defined as the percentage of amino acid residues in a candidate sequence that are identical with the amino acid residues in the Pol λ sequence, after aligning the sequences and introducing gaps, if necessary, to achieve the maximum percent sequence identity, and not considering any conservative substitutions as part of the sequence identity. The % identity values used herein are generated by WU-BLAST-2 which was obtained from [Altschul et al, Methods in Enzymology, 266:460-480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSPS2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Similarly, "percent (%) nucleic acid sequence identity" with respect to the coding sequence of the Pol λ polypeptides identified herein is defined as the percentage of nucleotide residues in a candidate sequence that are identical with the nucleotide residues in the Pol λ coding sequence as provided in SEQ ID No: 1 and 4. The identity values used herein were generated by the BLASTN module of WU BL AST-2 set to the default parameters, with overlap span and overlap fraction set to 1 and 0.125, respectively.

The present invention also includes active portions, and fragments of the Pol λ polypeptides of the invention.

An "active portion" of Pol λ polypeptide means a peptide which is less than said full length Pol λ polypeptide, but which retains at least some of its essential biological activity, e.g. as a DNA polymerase. For instance, smaller fragments of Pol λ can act as sequestrators or competitive antagonists by interacting with other proteins.

A "fragment" of the Pol λ polypeptide means a stretch of amino acid residues of at least 5 contiguous amino acids from the sequences set out as SEQ ID No: 1, 4, 7, 9 or 11, or more preferably at least 7 contiguous amino acids, or more preferably at least 10 contiguous amino acids or more preferably at least 20 contiguous amino acids or more preferably at least 40 contiguous amino acids. Fragments of the Pol λ polypeptide sequences may be useful as antigenic determinants or epitopes for raising antibodies to a portion of the Pol λ amino acid sequence.

A "derivative" of the Pol λ polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one, two, three, five or more amino acids, without fundamentally altering the essential activity of the Pol λ polypeptide.

A polypeptide according to the present invention may be isolated and/or purified (e.g. using an antibody) for instance after production by expression from encoding nucleic acid (for which see below). Polypeptides according to the present invention may also be generated wholly or partly by chemical synthesis. The isolated and/or purified polypeptide may be used in formulation of a composition, which may include at least one additional component, for example a pharmaceutical composition including a pharmaceutically acceptable excipient, vehicle or carrier. A composition including a polypeptide according to the invention may be used in prophylactic and/or therapeutic treatment as discussed below.

A polypeptide, peptide fragment, allele, mutant or variant according to the present invention may be used as an immunogen or otherwise in obtaining specific antibodies. Antibodies are useful in purification and other manipulation of polypeptides and peptides, diagnostic screening and therapeutic contexts. This is discussed further below.

A polypeptide according to the present invention may be used in screening for molecules which affect or modulate its activity or function. Such molecules may be useful in a therapeutic (possibly including prophylactic) context.

The Pol λ polypeptides can also be linked to a coupling partner, e.g. an effector molecule, a label, a drug, a toxin and/or a carrier or transport molecule. Techniques for coupling the peptides of the invention to both peptidyl and non-peptidyl coupling partners are well known in the art.

Antibodies Capable of Binding Pol λ Polypeptides

A further important use of the Pol λ polypeptides is in raising antibodies that have the property of specifically binding to the Pol λ polypeptides, or fragments or active portions thereof.

It is possible to produce monoclonal antibodies to Pol λ protein and the techniques for doing this are well established in the art. Monoclonal antibodies can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-239400. A hybridoma producing a monoclonal antibody may be subject to genetic mutation or other changes, which may or may not alter the binding specificity of antibodies produced.

The provision of the novel Pol λ polypeptides enables for the first time the production of antibodies able to bind it specifically: Accordingly, a further aspect of the present invention provides anti-Pol λ antibodies. Such an antibody may be specific in the sense of being able to distinguish between the polypeptide it is able to bind and other human polypeptides for which it has no or substantially no binding affinity (e.g. a binding affinity of about 1000× worse). Specific antibodies bind an epitope on the molecule which is either not present or is not accessible on other molecules. Antibodies according to the present invention may be specific for the wild-type polypeptide. Antibodies according to the invention may be specific for a particular mutant, variant, allele or derivative polypeptide as between that molecule and the wild-type Pol λ polypeptide, so as to be useful in diagnostic and prognostic methods as discussed below. Antibodies are also useful in purifying the polypeptide or polypeptides to which they bind, e.g. following production by recombinant expression from encoding nucleic acid.

Preferred antibodies according to the invention are isolated, in the sense of being free from contaminants such as antibodies able to bind other polypeptides and/or free of serum components. Monoclonal antibodies are preferred for some purposes, though polyclonal antibodies are within the scope of the present invention.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al, Nature, 357:80-82, 1992). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Example antibody fragments, capable of binding an antigen or other binding partner are the Fab fragment consisting of the VL, VH, C1 and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')$_2$ fragments, a bivalent fragment including two Fab fragments linked by a disulphide bridge at the hinge region. Single chain Fv fragments are also included.

Humanised antibodies in which CDRs from a non-human source are grafted onto human framework regions, typically with the alteration of some of the framework amino acid residues, to provide antibodies which are less immunogenic than the parent non-human antibodies, are also included within the present invention.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-0239400.

Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser exciting dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The mode of determining binding is not a feature of the present invention and those skilled in the art are able to choose a suitable mode according to their preference and general knowledge.

Antibodies according to the present invention may be used in screening for the presence of a polypeptide, for example in a test sample containing cells or cell lysate as discussed, and may be used in purifying and/or isolating a polypeptide according to the present invention, for instance following production of the polypeptide by expression from encoding nucleic acid therefor. Antibodies may modulate the activity of the polypeptide to which they bind and so, if that polypeptide has a deleterious effect in an individual, may be useful in a therapeutic context (which may include prophylaxis).

An antibody may be provided in a kit, which may include instructions for use of the antibody, e.g. in determining the presence of a particular substance in a test sample. One or more other reagents may be included, such as labelling molecules, buffer solutions, elutants and so on. Reagents may be provided within containers which protect them from the external environment, such as a sealed vial.

Diagnostic Methods

A number of methods are known in the art for analysing biological samples from individuals to determine whether the individual carries a Pol λ allele which is wild type or which includes a polymorphism. The purpose of such analysis may be used for diagnosis or prognosis, in particular for the diagnosis or prognosis of tumours or tumour malignancy, to assist a physician in determining the severity or likely course of the condition and/or to optimise treatment of it.

Broadly, the methods divide into those screening for the presence of Pol λ nucleic acid sequences and those that rely on detecting the presence or absence of the Pol λ polypeptide or isoforms thereof. The methods make use of biological samples from individuals that are suspected of contain the nucleic acid sequences or polypeptide. Examples of biological samples include blood, plasma, serum, tissue samples, tumour samples, saliva and urine.

Exemplary approaches for detecting Pol λ nucleic acid or polypeptides include:

(a) comparing the sequence of nucleic acid in the sample with the Pol λ nucleic acid sequence to determine whether the sample from the patient contains one or more mutations; or, (b) determining the presence in a sample from a patient of the polypeptide encoded by the POLL gene and, if present, determining whether the polypeptide is full length, and/or wild type and/or an isoform of the wild type polypeptide and/or is expressed at the normal level; or, (c) using DNA fingerprinting to compare the restriction pattern produced when a restriction enzyme cuts a sample of nucleic acid from the patient with the restriction pattern obtained from normal POLL gene or from known mutations thereof; or, (d) using a specific binding member capable of binding to a Pol λ nucleic acid sequence (either a normal sequence or a known mutated sequence), the specific binding member comprising nucleic acid hybridisable with the Pol λ nucleic acid sequence, or substances comprising an antibody domain with specificity for a native or mutated Pol λ nucleic acid sequence or the polypeptide encoded by it, the specific binding member being labelled so that binding of the specific binding member to its binding partner is detectable; or, (e) using PCR involving one or more primers based on normal or mutated POLL gene sequence to screen for normal or mutant POLL gene in a sample from a patient.

A "specific binding pair" comprises a specific binding member (sbm) and a binding partner (bp) which have a particular specificity for each other and which in normal conditions bind to each other in preference to other molecules. Examples of specific binding pairs are antigens and antibodies, molecules and receptors and complementary nucleotide sequences. The skilled person will be able to think of many other examples and they do not need to be listed here. Further, the term "specific binding pair" is also applicable where either or both of the specific binding member and the binding partner comprise a part of a larger molecule. In embodiments in which the specific binding pair are nucleic acid sequences, they will be of a length to hybridise to each other under the conditions of the assay, preferably greater than 10 nucleotides long, more preferably greater than 15 or 20 nucleotides long.

In most embodiments of the invention which relate to screening for Pol λ nucleic acid, the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

A variant form of the POLL gene may contain one or more insertions, deletions, substitutions and/or additions of one or more nucleotides compared with the wild-type sequence which may or may not disrupt the gene function. Differences at the nucleic acid level are not necessarily reflected by a difference in the amino acid sequence of the encoded polypeptide, but may be linked to a known dysfunction. However, a mutation or other difference in a gene may result in a frame-shift or stop codon, which could seriously affect the nature of the polypeptide produced (if any), or a point mutation or gross mutational change to the encoded polypeptide, including insertion, deletion, substitution and/or addition of one or more amino acids or regions in the polypeptide. A mutation in a promoter sequence or other regulatory region may prevent or reduce expression from the gene or affect the processing or stability of the mRNA transcript. An example of a single nucleotide polymorphism associated tumorigenesis is the single base pair change transition (C to T) at position 1683 of Pol λ cDNA which results in a change of the amino acid residue 438 (Arg) to tryptophan (Trp) in the coding region of Pol λ.

There are various methods for determining the presence or absence in a test sample of a particular nucleic acid sequence or a mutant, variant or allele thereof. Exemplary tests include nucleotide sequencing, hybridization using nucleic acid immobilized on chips, molecular phenotype tests, protein truncation tests (PTT), single-strand conformation polymorphism (SSCP) tests, mismatch cleavage detection and denaturing gradient gel electrophoresis (DGGE). These techniques and their advantages and disadvantages are reviewed in Nature Biotechnology, 15:422-426, 1997.

Tests may be carried out on preparations containing genomic DNA, cDNA and/or mRNA. Testing cDNA or mRNA has the advantage of the complexity of the nucleic acid being reduced by the absence of intron sequences, but the possible disadvantage of extra time and effort being required in making the preparations. RNA is more difficult to manipulate than DNA because of the wide-spread occurrence of RNAses.

Nucleic acid in a test sample may be sequenced and the sequence compared with the sequence shown in SEQ ID No: 4, to determine whether or not a difference is present. If so, the difference can be compared with known susceptibility alleles to determine whether the test nucleic acid contains one or more of the variations indicated.

Since it will not generally be time- or labour-efficient to sequence all nucleic acid in a test sample or even the whole POLL gene, a specific amplification reaction such as PCR using one or more pairs of primers may be employed to amplify the region of interest in the nucleic acid, for instance the POLL gene or a particular region in which mutations associated with a susceptibility to one of the conditions mentioned above. The amplified nucleic acid may then be sequenced as above, and/or tested in any other way to determine the presence or absence of a particular feature. Nucleic acid for testing may be prepared from nucleic acid removed from cells or in a library using a variety of other techniques such as restriction enzyme digest and electrophoresis.

Nucleic acid may be screened using a variant- or allele-specific probe. Such a probe corresponds in sequence to a region of the POLL gene, or its complement, containing a sequence alteration known to be associated with a susceptibility to the conditions mentioned above. Under suitably stringent conditions, specific hybridisation of such a probe to test nucleic acid is indicative of the presence of the sequence alteration in the test nucleic acid. For efficient screening purposes, more than one probe may be used on the same test sample.

Allele- or variant-specific oligonucleotides may similarly be used in PCR to specifically amplify particular sequences if present in a test sample. Assessment of whether a PCR band contains a gene variant may be carried out in a number of ways familiar to those skilled in the art. The PCR product may for instance be treated in a way that enables one to display the mutation or polymorphism on a denaturing polyacrylamide DNA sequencing gel, with specific bands that are linked to the gene variants being selected.

An alternative or supplement to looking for the presence of variant sequences in a test sample is to look for the presence of the normal sequence, e.g. using a suitably specific oligonucleotide probe or primer.

Approaches which rely on hybridisation between a probe and test nucleic acid and subsequent detection of a mismatch may be employed. Under appropriate conditions (temperature, pH etc.), an oligonucleotide probe will hybridise with a sequence which is not entirely complementary. The degree of base-pairing between the two molecules will be sufficient for them to anneal despite a mis-match. Various approaches are well known in the art for detecting the presence of a mis-match between two annealing nucleic acid molecules.

For instance, RNAse A cleaves at the site of a mis-match. Cleavage can be detected by electrophoresing test nucleic acid to which the relevant probe or probe has annealed and looking for smaller molecules (i.e. molecules with higher electrophoretic mobility) than the full length probe/test hybrid. Other approaches rely on the use of enzymes such as resolvases or endonucleases.

Thus, an oligonucleotide probe that has the sequence of a region of the normal POLL gene (either sense or anti-sense strand) in which mutations are known to occur may be annealed to test nucleic acid and the presence or absence of a mis-match determined. Detection of the presence of a mis-match may indicate the presence in the test nucleic acid of a mutation. On the other hand, an oligonucleotide probe that has the sequence of a region of the POLL gene including a mutation may be annealed to test nucleic acid and the presence or absence of a mis-match determined. The absence of a mis-match may indicate that the nucleic acid in the test sample has the normal sequence. In either case, a battery of probes to different regions of the gene may be employed.

The presence of differences in sequence of nucleic acid molecules may be detected by means of restriction enzyme digestion, such as in a method of DNA fingerprinting where the restriction pattern produced when one or more restriction enzymes are used to cut a sample of nucleic acid is compared with the pattern obtained when a sample containing the normal gene or a variant or allele is digested with the same enzyme or enzymes.

The presence or the absence of an important regulatory element in a promoter or other regulatory sequence located in introns may also be assessed by determining the level of mRNA production by transcription or the level of polypeptide production by translation from the mRNA.

A test sample of nucleic acid may be provided for example by extracting nucleic acid from cells, e.g. in saliva or preferably blood, or for pre-natal testing from the amnion, placenta or foetus itself.

There are various methods for determining the presence or absence in a test sample of a particular polypeptide, such as the polypeptide with the amino acid sequence shown in SEQ ID No: 4 or an amino acid sequence mutant, variant, allele or isoform thereof.

A sample may be tested for the presence of a binding partner for a specific binding member such as an antibody (or mixture of antibodies), specific for one or more particular variants of the Pol λ polypeptide.

A sample may be tested for the presence of a binding partner for a specific binding member such as an antibody (or mixture of antibodies), specific for the polypeptide.

In such cases, the sample may be tested by being contacted with a specific binding member such as an antibody under appropriate conditions for specific binding, before binding is determined, for instance using a reporter system as discussed. Where a panel of antibodies is used, different reporting labels may be employed for each antibody so that binding of each can be determined.

A specific binding member such as an antibody may be used to isolate and/or purify its binding partner polypeptide from a test sample, to allow for sequence and/or biochemical analysis of the polypeptide to determine whether it has the sequence and/or properties of the Pol λ polypeptide, or if it is a mutant or variant form. Amino acid sequence is routine in the art using automated sequencing machines.

Pharmaceuticals and Peptide Therapies

Pol λ polypeptides and antagonists and agonists may be useful in the treatment of a wide range of disorders. In particular, inhibitors of the Pol λ enzyme could be used to treat cancer, in particular in combination with drugs produce DNA damage, e.g. to drive cells into apoptosis, thereby preventing the diseased cells from repairing damage caused by the treatment with the drug. Further, the role of Pol λ in the error-prone DNA repair processes can lead to the generation of the secondary immune response, such as class switch recombination and somatic hypermutation. Thus, Pol λ inhibitors might be used in the treatment of immunosuppression, psoriasis, arthritis and graft rejection.

Pol λ polypeptides, inhibitors, antagonists (e.g. antibodies), peptides and nucleic acid of the invention can be formulated in pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

Alternatively, targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

Instead of administering these agents directly, they could be produced in the target cells by expression from an encoding gene introduced into the cells, eg in a viral vector (a variant of the VDEPT technique—see below). The vector could be targeted to the specific cells to be treated, or it could contain regulatory elements which are switched on more or less selectively by the target cells.

Alternatively, the agent could be administered in a precursor form, for conversion to the active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, e.g. an enzyme, in a vector by expression from encoding DNA in a viral vector (see for example, EP-A-415731 and WO90/07936).

A composition may be administered alone or in combination with other treatments, either simultaneously or sequentially, dependent upon the condition to be treated.

Methods of Screening for Pol λ Inhibitors and Drugs

A polypeptide according to the present invention may be used in screening for molecules which affect or modulate its activity or function. Such molecules may be useful in a therapeutic (possibly including prophylactic) context.

It is well known that pharmaceutical research leading to the identification of a new drug may involve the screening of very large numbers of candidate substances, both before and even after a lead compound has been found. This is one factor which makes pharmaceutical research very expensive and time-consuming. Means for assisting in the screening process can have considerable commercial importance and utility.

A method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Combinatorial library technology provides an efficient way of testing a potentially vast number of different substances for ability to modulate activity of a polypeptide. Such libraries and their use are known in the art. The use of peptide libraries is preferred.

Prior to or as well as being screened for modulation of activity, test substances may be screened for ability to interact with the polypeptide, e.g. in a yeast two-hybrid system (which requires that both the polypeptide and the test substance can be expressed in yeast from encoding nucleic acid). This may be used as a coarse screen prior to testing a substance for actual ability to modulate activity of the polypeptide. Alternatively, the screen could be used to screen test substances for binding to a Pol λ specific binding partner, to find mimetics of the Pol λ polypeptide, e.g. for testing as therapeutics.

Following identification of a substance which modulates or affects polypeptide activity, the substance may be investigated further. Furthermore, it may be manufactured and/or used in preparation, i.e. manufacture or formulation, of a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition to a patient, use of such a substance in manufacture of a composition for administration, and a method of making a pharmaceutical composition comprising admixing such a substance with a pharmaceutically acceptable excipient, vehicle or carrier, and optionally other ingredients.

EXAMPLES

Example 1

Cloning of the cDNA Corresponding to Human Pol λ

Cloning of the human POLL gene was initiated by the identification, in the public database dbEST/GeneBank, of a collection of ESTs that showed a high similarity with the cDNA sequence of the mouse POLL gene, previously obtained in our laboratory. These ESTs have the following identification numbers: AA742404, AA922738, AI091150, AA989195, W69567, AI123218, AI199486, AA576526, W69888, T81701 y H11886. All of them corresponded to the 3'-untranslated region, with the exception of the EST H11886, that seemed to contain part of the coding region of Pol λ. Starting with total cDNA obtained from human placenta, the cDNA corresponding to Pol λ was obtained as a series of overlapping fragments (FIG. 1) by PCR amplification. The first fragment (a136-20, FIG. 1) was obtained by specific PCR using primers derived form the ESTs described above. This fragment overlapped with the sequence of the EST H11886, and with the collection of ESTs corresponding to the 3'-end. This fragment, 1419 by long, spans positions 1107 to 2525 of the complete cDNA described here. The 3"-terminal segment, from 2526 to 2678 was deduced from the consensus of the ESTs.

The second fragment (a60-a, FIG. 1) was obtain by semi-specific PCR, with a sense primer derived from the murine sequence close to the initiation codon, and an antisense primer derived from the human PCR fragment a136-20. This second fragment, 996 by long, contains the coding sequence corresponding to positions 380 and 1375 of human Pol λ cDNA. The cDNA sequence was completed with fragment a91 (FIG. 1), obtained by RACE 5', a 504 by long fragment that contains the untranslated 5'-region, and the initial portion of the coding region. Therefore, the complete cDNA of human Pol λ contains a total of 2678 bp, with a 5'-untranslated region of 371 by (1-371), a coding sequence spanning 1728 by (372-2099), and a 3'-untranslated region of 579 by (2100-2678). The corresponding protein, Pol λ, has 575 amino acid residues. The coding sequences corresponding to the mouse and human homologues of Pol lambda share a 84% identity at the DNA level. At the protein level, the mouse and human Pol λ have an overall 80% identity, that reaches 90% in the most conserved domains, and is reduced to 57% in the region connecting the BRCT domain and the Pol β core.

Example 2

PCR Analysis of Pol λ Variants in cDNA from Different Origin, Normal and Tumoral To estimate the expression of the splicing variants hPOLLdelta6 and hPOLLdelta (6+7) in different tissues we developed assays to detect these variants at the cDNA level. The assay relies on the use of specific primers that allow to amplify cDNA fragments corresponding to each particular variant of Pol λ. As specific primers, able to distinguish among the different variants, splicing-specific sense primers were used, whereas a common antisense primer was used in all cases.

Antisense primer for both variants, named 2B2, corresponding to a common region located at exon 9: 2B2 5'-GGAGCGGTTGAAGTGTGC-3' (SEQ ID NO: 45), Sense primer, specific for the variant hPOLLdelta6, named 2B3, was designed in such a way that its first 11 5'-nucleotides correspond to the end of exon 5, whereas the rest of the primer correspond to the initial sequences of exon 7: 2B3 5'-CCTCGTACCAGGGCTTCC-3' (SEQ ID NO: 46), On the other hand, and following identical criteria, the specific primer corresponding to the variant hPOLLdelta (6+7), named 2B4, was designed in such a way that its first 5'-nucleotides correspond to the end of exon 5, and the rest of nucleotides correspond to the initial sequence of exon 8: 2B4 5'-CACCTCGTACCAGGTCCAGA-3' (SEQ ID NO: 47).

To carry out the assay, separated reaction tubes contained cDNA samples from different origins, and the following combination of primers: 1) 2B3 and 2B2 (FIGS. 2 and 3) 2B4 and 2B2 (FIG. 4), at an individual concentration of 1 µM. The reaction mixture contained Tris-HCl 10 mM pH 9, KCl 50 mM, MgCl2 1.5 mM, each nucleotide (dATP, dCTP, dGTP y dTTP) at 0.2 mM, and Taq DNA pol at 0.025 U/ml. The reactions took place during 40 cycles of PCR, being each cycle: 10 s at 94° C. and 20 s at 60° C. The identity of the fragments was confirmed by cloning and sequencing.

Example 3

Expression and Purification of Mouse Pol λ and Generation of Specific Antibodies The cDNA region coding for Pol λ was PCR-amplified from the plasmid provided by the LLNL, using primers designed for a further cloning into sites EcoRI and NdeI of vector pT7, or into site EcoRI and BamHI of the expression plasmid pRSET-A (Invitrogen). In the latter case, a 6× Histidine tag is added at the N-terminus of the recombinant protein.

For transformation, the E. coli strain TOP10F' was used. After checking all constructs by sequencing, transformation was carried out in the *E. coli* strain BL21 (DE3) pLysS, that harbours the T7 RNA polymerase gene under control of the lacUV5 promoter, inducible by IPTG. Induction of Pol λ expression was carried out at 30, 32 and 37° C., at an optical density of 0.6 (A600). IPTG (Sigma), at a concentration of 0.5 mM, was added. When indicated, Rifampicine (Sigma) was added 20 min after induction, at a concentration of 120 µg/ml. The optimal time of induction was shown to be 2 hours. Alternatively, induction was carried out in the presence of 2.5 mM Betaina (Sigma) and 1M sorbitol (BDH). In all the conditions assayed, the mouse Pol λ was insoluble. On the contrary, expression of the human Pol λ in *E. coli*, following the same strategy, resulted in a soluble and active protein.

The insoluble fraction corresponding to the mouse Pol λ expressed in *E. coli* was used for generating polyclonal antibodies. After electrophoretic separation in the presence of SDS, the band corresponding to Pol λ was excised from the gel and triturated by using a "French Press". Aliquots corresponding to 100 µg of Pol λ were used as an antigen to immunize rabbits by multiple intradermal innoculation. The serum obtained after an standard immunization protocol were able to recognize specifically Pol λ by Western blot analysis.

Example 5

PCR/SSCP Screening of the Entire Coding Region of Human Pol λ

A panel of cDNA libraries from normal versus tumoral human tissues (Clontech) was used as a template to search for possible genetic alterations in the human Pol λ gene. Sets of primers were selected to cover the entire coding sequence of the human Pol λ gene. The amplimers obtained were separately screened by SSCP. Using primers: sense 5'GGCAT-GTGGTTCATACCGAC (SEQ ID NO: 48) and antisense 5'GGAGCGGTTGAAGTGTGC (SEQ ID NO: 45), a portion of the catalytic domain (~320 bp) of Pol λ was amplified, the PCR product from this region including the polymorphic variant.

Template aliquots were 5× diluted and the resulting aliquot was used as a 5× stock for PCR. All PCR reactions were conducted at standard conditions using 10 µmol of each primer, 0.25 mM dNTPs, 1×Taq buffer (10 mM Tris, 50 mM, KCl, gelatin, 0.2 mg/ml BSA, pH 8.5), 0.25 U of Taq polymerase to a total volume of PCR mixture 10 ml. PCR parameteres were as follows, during 35 cycles: 94° C./15 sec for denaturation; 60° C./30 sec, for primer annealing, and 72° C./15 sec, for extension. PCR products were then subjected to SSCP analysis.

Genomic DNA from 12 unrelated individuals was prepared from peripheral blood lymphocytes as described. PCRs were performed with approximately 20-50 ng of genomic DNA at standard conditions: 10 pmol of each primer, 0.25 mM dNTPs, 1×Taq buffer (10 mM Tris, 50 mM, KCl, gelatin, 0.2 mg/ml BSA, pH 8.5), 0.25 U of Taq polymerase to a total volume of PCR mixture 10 ml. Sequence of the primers to amplify the portion of the catalytic domain of human pol λ (entire exon 8) were: sense 5'GGCATGTGGTTCATAC-CGAC (SEQ ID NO: 48); antisense 5'TTCCTGCCGAA-GACTGTCA (SEQ ID NO: 49). PCR parameters were as follows, during 35 cycles: 94° C./15 sec for denaturation; 60° C./30 sec, for primer annealing, and 72° C./15 sec, for extension. PCR products were cloned into TA cloning vector pCRII. (Invitrogen) and sequenced by automated dideoxy termination dye method on ABI 373 (Applied Biosystems) automatic sequencer.

Single strand conformational polymorphism analysis (SSCP) was carried as described (Orita et al, 1989). PCR products were diluted in 1× formamide loading dye and denatured at 95° C. for 3 min. Samples were then applied to 8% polyacrylamide gel containing 15% of glycerol. After the run, gel was silver stained as described: 15 min fixation in 10% ethanol, 10 min incubation with 1% $HNO_3$, 30 min incubation with 0.2% $AgNO_3$ containing 0.1% formaldehyde and developing with 3% $Na_2CO_3$ containing 0.05% formaldehyde until the bands appear; 10 min fixation with 10% acetic acid.

Figure 5:
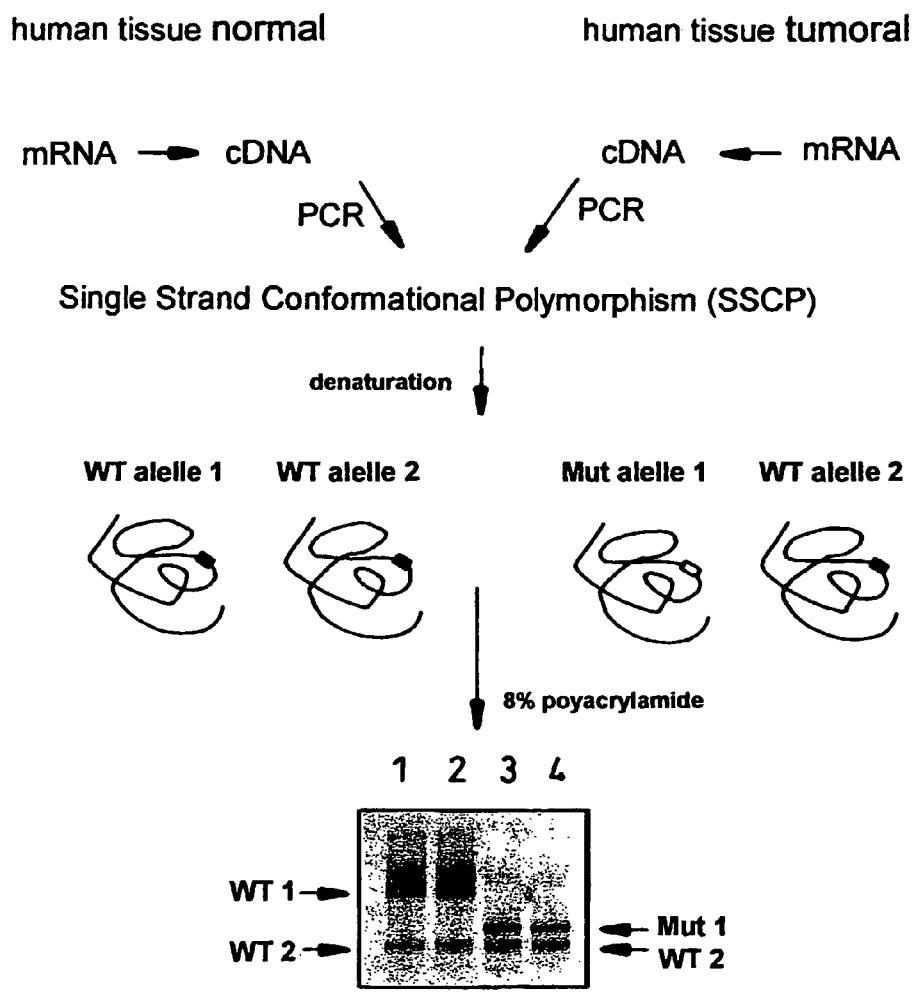
FIG. 5: A. Single-strand conformational polymorphism (SSCP) analysis demonstrating the occurrence of a possible allelic variant in the coding sequence of human Pol λ. This variant was initially found in an ovarian carcinoma cell line from CLONTECH (lanes 3 and 4). Lanes 1 and 2 represent a normal ovarian tissue. B. After cloning and sequencing, a single nucleotide polymorphism (C to T), located at position 1683 of the human Pol λ cDNA, was observed (normal allele=SEQ ID NO: 13 for nucleic acid and SEQ ID NO: 15 for amino acid while mutant allele=SEQ ID NO: 14 for nucleic acid and SEQ ID NO: 16 for amino acid). This polymorphism, confirmed in the Spanish population, produces a change of one amino acid residue (Arg438 into Trp) in a portion of the enzyme located very close to the active site.
Figure 6:
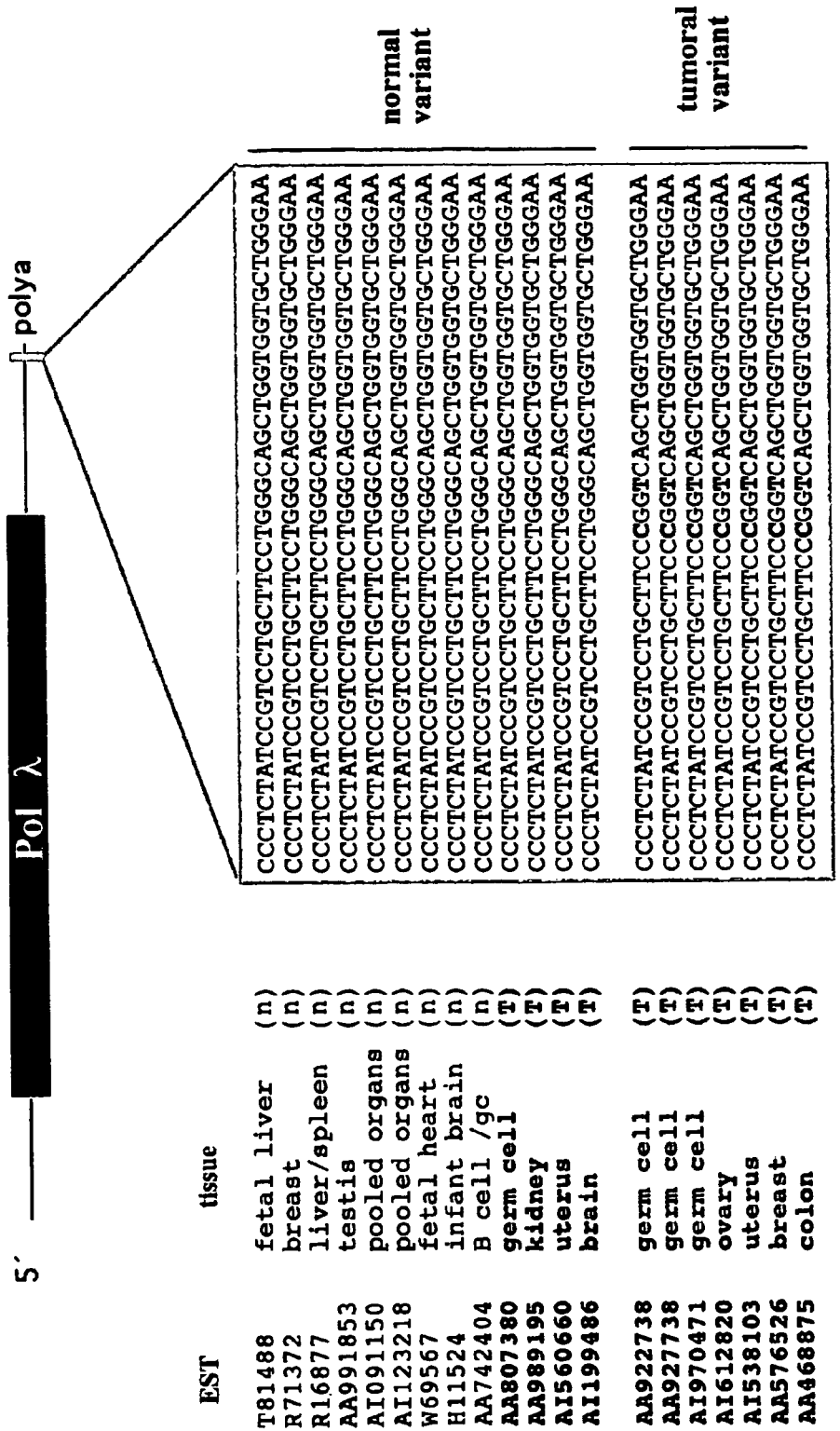
FIG. 6: A putative allelic variant of human Pol λ associated with tumourogenesis showing EST T81488 (SEQ ID NO: 17), EST R71372 (SEQ ID NO: 18), EST R16877 (SEQ ID NO: 19), EST AA991853 (SEQ ID NO: 20), EST AI091150 (SEQ ID NO: 21), EST AI123218 (SEQ ID NO: 22), EST W69567 (SEQ ID NO: 23), EST H11524 (SEQ ID NO: 24), EST AA742404 (SEQ ID NO: 25), EST AA807380 (SEQ ID NO: 26), EST AA989195 (SEQ ID NO: 27), EST AI560660 (SEQ ID NO: 28), EST AI199486 (SEQ ID NO: 29), EST AA922738 (SEQ ID NO: 30), EST AA927738 (SEQ ID NO: 31), EST AI970471 (SEQ ID NO: 32), EST AI612820 (SEQ ID NO: 33), EST AI538103 (SEQ ID NO: 34), EST AA576526 (SEQ ID NO: 35), and EST AA468875 (SEQ ID NO: 36).

Single strand conformational polymorphism (SSCP) and DNA sequencing were used to analyze overlapping PCR products covering the complete cDNA of human Pol λ, searching for the presence of mutations associated to cancer. Initially, a panel of normal versus tumoral human tissues (Clontech) was used. As shown in FIG. 5, SSCP has revealed an altered mobility in the SSCP analysis was observed in the case of ovarian carcinoma cDNA library in a portion of human Pol λ close to the catalytic site. Cloning and sequencing of these fragments identified a single base pair substitution present in a homozygous form in ovarian carcinoma cDNA, while a heterozygous constitution was detected in the SCCP profiles corresponding to normal ovarian tissue cDNA library. A single base pair change transition (C to T) at position 1683 of Pol cDNA results in a change of the amino acid residue 438 (Arg) to tryptophan (Trp) in the coding region of Pol λ. We have analysed the incidence of this particular polymorphism in the population by screening the genomic DNA of 12 unrelated individuals. Results showed a mendelian segregation of this polymorphism, with a mild dominance of the allele coding for the version with Arg. Activity assays of human Pol λ for each particular allelic variant were then studied.

Example 6

In Situ Hybridization

Non-radioactive in situ hybridization was performed on tissue sections at 12-14 µm thickness mounted on poly-L-lysine coated glass slides. Testes from 20 days postnatal and adult were dissected and immediately fixed in a 4% paraformaldehyde in DEPC-treated PBS at 4° C. overnight. Agar-embedded sections were hybridized with 0.1 µg/ml sense or antisense digoxigenin-labelled riboprobes (Boehringer Mannheim). Finally, the slides were stained with Hoechst 33258, observed under fluorescence and bright field microscopy and CCD camera recorded. Then, the coverslips were removed, the slides were dehydrated and mounted with DePeX (Serve).

These experiments showed that Pol λ mRNA was not detectable in proliferating spermatogonia, but was very abundant at the cytoplasm of pachytene spermatocytes, stage at which meiotic recombination occurs.

Example 7

Biochemical Characterisation of Human Pol λ

The detection of splicing variants (not truncated) of human Pol λ that could represent functional versions of the DNA polymerase was intriguing, since some of this forms appear to be specifically expressed in tumoral samples. We therefore investigated whether these forms could represent altered (mutator) variants of the polymerase that could be consequential for tumorogenesis.

We have also succeeded in expressing the human Pol λ in E. coli in a soluble and active form. Preliminary data indicates that Pol λ is highly error-prone, and this supports the fact that Pol λ function could be associated to DNA repair during meiosis must be reconsidered. Pol λ is expressed preferentially in germinal cells, associated to the process that generates the gametes. Taking into account that this enzyme is able to introduce mutations when polymerising on undamaged templates, the function of Pol λ could be to generate some degree of variability in our germinal cells, and that such a mutagenesis background could be critical for genome evolution.

Figure 7:
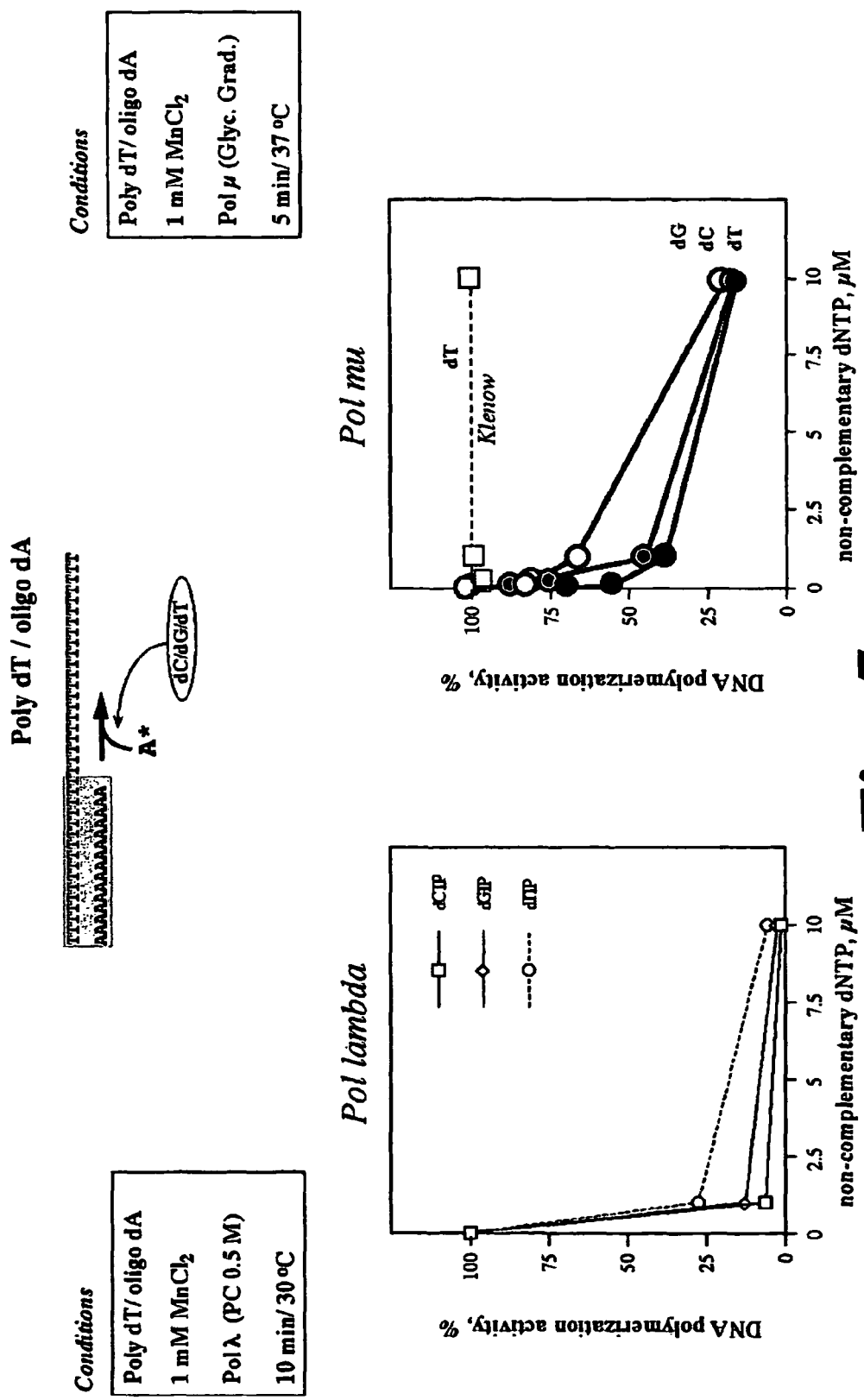
FIG. 7: Shows that Pol λ polymerisation is strongly inhibited by non-complementary dNTPs (polydT/polydA (SEQ ID NOs: 37 and 38 respectively), 1 mMMnCl2, Pol λ (PC 0.5 M), 10 min at 30° C.).

The evidences for such a putative function derives from the in vitro analysis of the DNA polymerization catalyzed by human Pol λ. To demonstrate that Pol λ is behaving as a mutase, we used an unambiguous in vitro assay in which the template strand is homopolymeric (poly dT), and therefore the primer strand (oligo dA) can be extended with dATP as the sole correct (complementary nucleotide). Unlike a control enzyme with significant insertion fidelity (Klenow), incorporation of labeled dATP by human Pol lambda was strongly inhibited by addition of a relatively low concentration (1 μM) of each of the non complementary deoxynucleotides. The level of inhibition was even higher than that previously reported for Pol mu (a mutase), see FIG. 7.

Figure 8:
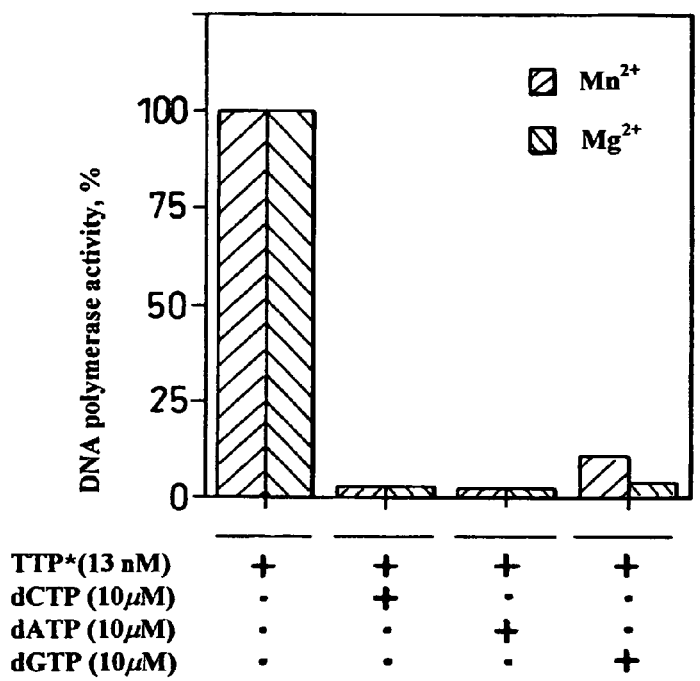
FIG. 8: shows that Pol λ polymerisation is strongly inhibited by non-complementary dNTPs using a polydA/dT template in the presence of either manganese or magnesium ions.

FIG. 8 also shows that the inhibition of Pol λ is independent of the nature of the activating magnesium or manganese ions used in the assay.

Thus, it is likely that the error-proneness of Pol λ makes this enzyme a good candidate to create/change DNA information during processes oriented to generate variability as, i.e. somatic hypermutation and/or perhaps predominantly as a specific process occurring during gametogenesis. The latter idea would be supported by the predominant expression of Pol λ in pachytene spermatocytes and round spermatids.

The references mentioned herein are all expressly incorporated by reference.

The invention claimed is:

1. An isolated DNA Pol λ polypeptide which has DNA polymerase activity, comprising the amino acid sequence of SEQ ID NO: 5, wherein the arginine residue at position 438 is replaced with tryptophan.

* * * * *

SEQUENCE LISTING

<160> NUMBER OF SEQ ID NOS: 49

<210> SEQ ID NO 1
<211> LENGTH: 2336
<212> TYPE: DNA
<213> ORGANISM: Mus musculus
<220> FEATURE:
<221> NAME/KEY: CDS
<222> LOCATION: (84)..(1805)

<400> SEQUENCE: 1

```
tttttttttt ttcccctcta cccttcctc ccccaatccg ttttcattgg ctcccatgaa          60
aggccaggat ccagcgccct tca atg gac cct cag ggc atc gtg aag gcc ttt        113
                        Met Asp Pro Gln Gly Ile Val Lys Ala Phe
                         1               5                  10 ccc aag cgg aag aaa agt cat gca gat cta tct tca aaa gca ctt gca          161
Pro Lys Arg Lys Lys Ser His Ala Asp Leu Ser Ser Lys Ala Leu Ala
                 15                  20                  25 aag att ccc aaa agg gag gtg gga gaa gct aga gga tgg ctg agc tcc          209
Lys Ile Pro Lys Arg Glu Val Gly Glu Ala Arg Gly Trp Leu Ser Ser
             30                  35                  40 ctg aga gcc cac att atg ccc gct ggc att gga cgt gcc cgg gct gaa          257
Leu Arg Ala His Ile Met Pro Ala Gly Ile Gly Arg Ala Arg Ala Glu
         45                  50                  55 ctc ttt gag aag cag att atc cac cat ggc ggc cag gtg tgc tct gcc          305
Leu Phe Glu Lys Gln Ile Ile His His Gly Gly Gln Val Cys Ser Ala
 60                  65                  70 cag gcc cca gga gtc act cac att gtg gtg gat gaa gac atg gac tat          353
Gln Ala Pro Gly Val Thr His Ile Val Val Asp Glu Asp Met Asp Tyr
 75                  80                  85                  90 gag cgg gct ctc cgg ctc ctc agg ttg ccc cag cta ccc cct ggt gcc          401
Glu Arg Ala Leu Arg Leu Leu Arg Leu Pro Gln Leu Pro Pro Gly Ala
                 95                 100                 105 cag ctg gtg aag tcc acc tgg ctg agc ttg tgc ctg cag gag gga agg          449
Gln Leu Val Lys Ser Thr Trp Leu Ser Leu Cys Leu Gln Glu Gly Arg
             110                 115                 120 ctg aca gac acg gaa gga ttc agc ctt ccc atg ccc aag agg tcc ttg          497
Leu Thr Asp Thr Glu Gly Phe Ser Leu Pro Met Pro Lys Arg Ser Leu
         125                 130                 135 gat gaa cca cag ccc agc aag tca ggc caa gat gct tct gct cct ggc          545
```

-continued

```
Asp Glu Pro Gln Pro Ser Lys Ser Gly Gln Asp Ala Ser Ala Pro Gly
    140                 145                 150 acc cag cgg gat tta ccc agg acc acc ctt tct ctt tcc cct cct cac    593
Thr Gln Arg Asp Leu Pro Arg Thr Thr Leu Ser Leu Ser Pro Pro His
155                 160                 165                 170 acc aga gct gta tct cct ccc cca acg gca gaa aag cca tca aga acc    641
Thr Arg Ala Val Ser Pro Pro Pro Thr Ala Glu Lys Pro Ser Arg Thr
                175                 180                 185 caa gcc cag ctc agc tca gag gat gaa acc agc gat gga gaa ggg ccc    689
Gln Ala Gln Leu Ser Ser Glu Asp Glu Thr Ser Asp Gly Glu Gly Pro
                190                 195                 200 cag gtt agc tca gca gat ctg caa gcc ttg atc act ggg cac tac ccc    737
Gln Val Ser Ser Ala Asp Leu Gln Ala Leu Ile Thr Gly His Tyr Pro
            205                 210                 215 act ccc cct gag gaa gat ggt ggg cct gac cca gca cca gaa gct ctg    785
Thr Pro Pro Glu Glu Asp Gly Gly Pro Asp Pro Ala Pro Glu Ala Leu
        220                 225                 230 gat aaa tgg gtc tgt gca cag ccc tcg agc cag aag gca act aac tac    833
Asp Lys Trp Val Cys Ala Gln Pro Ser Ser Gln Lys Ala Thr Asn Tyr
235                 240                 245                 250 aat ctg cac atc aca gag aag ctg gaa gtg ctg gct aaa gcc tac agt    881
Asn Leu His Ile Thr Glu Lys Leu Glu Val Leu Ala Lys Ala Tyr Ser
                255                 260                 265 gtc cag gga gac aag tgg agg gcc ctg ggc tat gca aag gcc atc aat    929
Val Gln Gly Asp Lys Trp Arg Ala Leu Gly Tyr Ala Lys Ala Ile Asn
                270                 275                 280 gct ctc aag agc ttc cac aag cct gtc agc tcc tac cag gag gcc tgt    977
Ala Leu Lys Ser Phe His Lys Pro Val Ser Ser Tyr Gln Glu Ala Cys
            285                 290                 295 agc atc ccg gga att ggc aag cgg atg gcg gag aag gtc atg gag atc   1025
Ser Ile Pro Gly Ile Gly Lys Arg Met Ala Glu Lys Val Met Glu Ile
        300                 305                 310 ctg gag agt ggg cat ctg cgg aag cta gac cac atc agt gac agt gtg   1073
Leu Glu Ser Gly His Leu Arg Lys Leu Asp His Ile Ser Asp Ser Val
315                 320                 325                 330 cct gtc ttg gag ctc ttc tcc aac atc tgg gga gct ggg acg aag act   1121
Pro Val Leu Glu Leu Phe Ser Asn Ile Trp Gly Ala Gly Thr Lys Thr
                335                 340                 345 gcc cag atg tgg tac cat cag ggc ttc cga aac cta gaa gat ctc caa   1169
Ala Gln Met Trp Tyr His Gln Gly Phe Arg Asn Leu Glu Asp Leu Gln
                350                 355                 360 agc ctg ggc tcc ctg acc gct cag cag gcc att ggc ttg aag cac tac   1217
Ser Leu Gly Ser Leu Thr Ala Gln Gln Ala Ile Gly Leu Lys His Tyr
            365                 370                 375 gat gac ttc ctg gac cgc atg ccc agg gag gag gct gcg gaa att gag   1265
Asp Asp Phe Leu Asp Arg Met Pro Arg Glu Glu Ala Ala Glu Ile Glu
        380                 385                 390 cag acg gtc cgg ata tca gcc cag gcc ttc aac cct ggg ctg ctg tgt   1313
Gln Thr Val Arg Ile Ser Ala Gln Ala Phe Asn Pro Gly Leu Leu Cys
395                 400                 405                 410 gtg gct tgt ggc tct tac cga cgg ggg aag atg acg tgc ggg gat gtg   1361
Val Ala Cys Gly Ser Tyr Arg Arg Gly Lys Met Thr Cys Gly Asp Val
                415                 420                 425 gat gta ctc att act cac ccc gat ggc cga tcc cac cgg ggc atc ttc   1409
Asp Val Leu Ile Thr His Pro Asp Gly Arg Ser His Arg Gly Ile Phe
                430                 435                 440 agc tgc ctc ctt gat agc ctt cgg cag caa ggg ttc ctc aca gat gac   1457
Ser Cys Leu Leu Asp Ser Leu Arg Gln Gln Gly Phe Leu Thr Asp Asp
            445                 450                 455
```

```
ttg gtg agc cag gag gag aac ggc caa cag cag aaa tac ctg ggt gtg    1505
Leu Val Ser Gln Glu Glu Asn Gly Gln Gln Gln Lys Tyr Leu Gly Val
    460                 465                 470 tgc cgg ctc cca ggg ccc ggg aag cgc cac cgg cga ctg gac atc atc    1553
Cys Arg Leu Pro Gly Pro Gly Lys Arg His Arg Arg Leu Asp Ile Ile
475                 480                 485                 490 gtg gta ccc tac tgt gag ttt gcc tgt gcc ctg ctc tac ttc acc ggc    1601
Val Val Pro Tyr Cys Glu Phe Ala Cys Ala Leu Leu Tyr Phe Thr Gly
                495                 500                 505 tct gcc cac ttc aac cgg tcc atg aga gct ctg gcc aag acc aag ggc    1649
Ser Ala His Phe Asn Arg Ser Met Arg Ala Leu Ala Lys Thr Lys Gly
        510                 515                 520 atg agc ctg tcg gag cat gcg ctc agt gca gct gta gtc cgg aac agc    1697
Met Ser Leu Ser Glu His Ala Leu Ser Ala Ala Val Val Arg Asn Ser
    525                 530                 535 caa ggt gtc aag gtg ggg cct gga caa gtg ctg ccc acc ccc acg gag    1745
Gln Gly Val Lys Val Gly Pro Gly Gln Val Leu Pro Thr Pro Thr Glu
540                 545                 550 aag gac gtc ttc aag cac tta ggc ctg ccc tac cgg gag cca gct gaa    1793
Lys Asp Val Phe Lys His Leu Gly Leu Pro Tyr Arg Glu Pro Ala Glu
555                 560                 565                 570 cgg gac tgg tga cctaggactt ggagcaaggg gaaccatgtt gaatgaactg       1845
Arg Asp Trp actcatgtag ccatctccca ccctcttagc tgtgcctcgc tttgtcggtt acgcttgccc   1905
tgagtgacca agctaggagc tttgggcctg cggggaagag ccagtctgat tctgagagcc   1965
cgcaagctct ctctcctgga caggatttat gctgctgtcc cctctcctcc cagtgacagg   2025
ttttcacacg gcccctccc tgttcaagca gaacaggtgg ctggtttcaa ggcggtttcc    2085
tgcactgaag gcccgagctt ccctttccac cccaagactg atgtagctgt gtggggtcag   2145
caggggctgc aggagaggga agcagctgtg ggctcagcgt cttccgtgag ccttcacagt   2205
agagaaagcc atgtggattc tctcacccgc tcacttcctg tgcagctgga gctgctgggg   2265
gtggcctgtc cagaccatga gggtggcttc taagggccct ggggcctaat aaagtgcttc   2325
tgacattcaa a                                                      2336

<210> SEQ ID NO 2
<211> LENGTH: 573
<212> TYPE: PRT
<213> ORGANISM: Mus musculus

<400> SEQUENCE: 2

Met Asp Pro Gln Gly Ile Val Lys Ala Phe Pro Lys Arg Lys Lys Ser
1               5                   10                  15

His Ala Asp Leu Ser Ser Lys Ala Leu Ala Lys Ile Pro Lys Arg Glu
            20                  25                  30

Val Gly Glu Ala Arg Gly Trp Leu Ser Ser Leu Arg Ala His Ile Met
        35                  40                  45

Pro Ala Gly Ile Gly Arg Ala Arg Ala Glu Leu Phe Glu Lys Gln Ile
    50                  55                  60

Ile His His Gly Gly Gln Val Cys Ser Ala Gln Ala Pro Gly Val Thr
65                  70                  75                  80

His Ile Val Val Asp Glu Asp Met Asp Tyr Glu Arg Ala Leu Arg Leu
                85                  90                  95

Leu Arg Leu Pro Gln Leu Pro Pro Gly Ala Gln Leu Val Lys Ser Thr
            100                 105                 110

Trp Leu Ser Leu Cys Leu Gln Glu Gly Arg Leu Thr Asp Thr Glu Gly
```

-continued

```
                115                 120                 125
Phe Ser Leu Pro Met Pro Lys Arg Ser Leu Asp Glu Pro Gln Pro Ser
    130                 135                 140
Lys Ser Gly Gln Asp Ala Ser Ala Pro Gly Thr Gln Arg Asp Leu Pro
145                 150                 155                 160
Arg Thr Thr Leu Ser Leu Ser Pro Pro His Thr Arg Ala Val Ser Pro
                165                 170                 175
Pro Pro Thr Ala Glu Lys Pro Ser Arg Thr Gln Ala Gln Leu Ser Ser
            180                 185                 190
Glu Asp Glu Thr Ser Asp Gly Glu Gly Pro Gln Val Ser Ser Ala Asp
            195                 200                 205
Leu Gln Ala Leu Ile Thr Gly His Tyr Pro Thr Pro Pro Glu Glu Asp
    210                 215                 220
Gly Gly Pro Asp Pro Ala Pro Glu Ala Leu Asp Lys Trp Val Cys Ala
225                 230                 235                 240
Gln Pro Ser Ser Gln Lys Ala Thr Asn Tyr Asn Leu His Ile Thr Glu
                245                 250                 255
Lys Leu Glu Val Leu Ala Lys Ala Tyr Ser Val Gln Gly Asp Lys Trp
            260                 265                 270
Arg Ala Leu Gly Tyr Ala Lys Ala Ile Asn Ala Leu Lys Ser Phe His
    275                 280                 285
Lys Pro Val Ser Ser Tyr Gln Glu Ala Cys Ser Ile Pro Gly Ile Gly
    290                 295                 300
Lys Arg Met Ala Glu Lys Val Met Glu Ile Leu Glu Ser Gly His Leu
305                 310                 315                 320
Arg Lys Leu Asp His Ile Ser Asp Ser Val Pro Val Leu Glu Leu Phe
                325                 330                 335
Ser Asn Ile Trp Gly Ala Gly Thr Lys Thr Ala Gln Met Trp Tyr His
            340                 345                 350
Gln Gly Phe Arg Asn Leu Glu Asp Leu Gln Ser Leu Gly Ser Leu Thr
            355                 360                 365
Ala Gln Gln Ala Ile Gly Leu Lys His Tyr Asp Asp Phe Leu Asp Arg
    370                 375                 380
Met Pro Arg Glu Glu Ala Ala Glu Ile Glu Gln Thr Val Arg Ile Ser
385                 390                 395                 400
Ala Gln Ala Phe Asn Pro Gly Leu Leu Cys Val Ala Cys Gly Ser Tyr
                405                 410                 415
Arg Arg Gly Lys Met Thr Cys Gly Asp Val Asp Val Leu Ile Thr His
            420                 425                 430
Pro Asp Gly Arg Ser His Arg Gly Ile Phe Ser Cys Leu Leu Asp Ser
            435                 440                 445
Leu Arg Gln Gln Gly Phe Leu Thr Asp Asp Leu Val Ser Gln Glu Glu
    450                 455                 460
Asn Gly Gln Gln Gln Lys Tyr Leu Gly Val Cys Arg Leu Pro Gly Pro
465                 470                 475                 480
Gly Lys Arg His Arg Arg Leu Asp Ile Ile Val Val Pro Tyr Cys Glu
                485                 490                 495
Phe Ala Cys Ala Leu Leu Tyr Phe Thr Gly Ser Ala His Phe Asn Arg
            500                 505                 510
Ser Met Arg Ala Leu Ala Lys Thr Lys Gly Met Ser Leu Ser Glu His
            515                 520                 525
Ala Leu Ser Ala Ala Val Val Arg Asn Ser Gln Gly Val Lys Val Gly
    530                 535                 540
```

-continued

Pro Gly Gln Val Leu Pro Thr Pro Thr Glu Lys Asp Val Phe Lys His
545                 550                 555                 560

Leu Gly Leu Pro Tyr Arg Glu Pro Ala Glu Arg Asp Trp
                565                 570

<210> SEQ ID NO 3
<211> LENGTH: 8300
<212> TYPE: DNA
<213> ORGANISM: Mus musculus
<220> FEATURE:
<221> NAME/KEY: exon
<222> LOCATION: (1)..(58)
<220> FEATURE:
<221> NAME/KEY: exon
<222> LOCATION: (828)..(964)
<220> FEATURE:
<221> NAME/KEY: satellite
<222> LOCATION: (1079)..(1156)
<223> OTHER INFORMATION: microsatellite (CAAA)n
<220> FEATURE:
<221> NAME/KEY: satellite
<222> LOCATION: (1565)..(1599)
<223> OTHER INFORMATION: microsatellite AT rich
<220> FEATURE:
<221> NAME/KEY: exon
<222> LOCATION: (1625)..(1919)
<220> FEATURE:
<221> NAME/KEY: exon
<222> LOCATION: (2512)..(2829)
<220> FEATURE:
<221> NAME/KEY: satellite
<222> LOCATION: (3088)..(3138)
<223> OTHER INFORMATION: microsatellite (CAAA)n
<220> FEATURE:
<221> NAME/KEY: satellite
<222> LOCATION: (3779)..(3823)
<223> OTHER INFORMATION: microsatellite (GT)n
<220> FEATURE:
<221> NAME/KEY: satellite
<222> LOCATION: (3874)..(3901)
<223> OTHER INFORMATION: microsatellite (TGG)n
<220> FEATURE:
<221> NAME/KEY: satellite
<222> LOCATION: (4017)..(4272)
<223> OTHER INFORMATION: microsatellite (GCCTCT)n
<220> FEATURE:
<221> NAME/KEY: exon
<222> LOCATION: (4472)..(4645)
<220> FEATURE:
<221> NAME/KEY: satellite
<222> LOCATION: (4914)..(4982)
<223> OTHER INFORMATION: microsatellite (GT)n
<220> FEATURE:
<221> NAME/KEY: exon
<222> LOCATION: (5356)..(5484)
<220> FEATURE:
<221> NAME/KEY: exon
<222> LOCATION: (6898)..(7066)
<220> FEATURE:
<221> NAME/KEY: exon
<222> LOCATION: (7405)..(8300)

<400> SEQUENCE: 3 ttt ttt ttt ttt ccc ctc tac ccc ttc ctc ccc caa tcc gtt ttc att    48
Phe Phe Phe Phe Pro Leu Tyr Pro Phe Leu Pro Gln Ser Val Phe Ile
1               5                   10                  15 ggc tcc cat g gtgagtttat ttctctttgc cgggagattc taacctactt           98
Gly Ser His tggaccggtc ctggggccgg gtggggtggg gatgctccca gaacttttag ggatccagca  158
ccaactctct tctggcccca gctgggagtc cctggttcac accagctgct cacagtggat  218
gtggcacgtc tgcttcggtc ttgccccacct ccagctgtga gggctcccta catctgctgc  278

-continued

```
ggctgcactc cacctccctg cagctgcggg gctcagaccc gcgcgatggg gctgctgcga      338
cagggacagg tgcgcagcgt gcccacaact ttccctgaag cctcactccc caggttttct      398
tctgcgaatg cacattgagg ctagagaaag atgatgcgag gtttatgtga catgtccctt      458
agactccaat tcgttgggga gatgaagact ctcctaaaga tgtagtccgg ttcccaaacc      518
cgtcatcatt ttggaaaagt tcttggaag gggacgcaga ggctgactct gcgctatatt       578 cctccccca ccccaccc atgttgtttc ctttcgatcc acacctcccc tacacccaca         638
agaatcccaa cctttccctg gcttccctca gtacgactag ggttgaaagg ctggtatgtg      698
tgtgtggcac tcggattaaa tcacttaagt ttaactgggg tttccgagac ctctgagaaa     758
gggacctgtt acccctaaac cccacctcta tgccaaatta ttaagggctg gctctcaatc      818
```

| ctttaacag aa | agg cca gga tcc agc gcc ctt caa tgg acc ctc agg gca |     | 868 |
|---|---|---|---|
|  | Glu Arg Pro Gly Ser Ser Ala Leu Gln Trp Thr Leu Arg Ala |  |  |
|  | 20 25 30 |  |  |

| tcg tga | agg cct ttc cca agc gga aga aaa gtc atg cag atc tat ctt | 916 |
|---|---|---|
| Ser | Arg Pro Phe Pro Ser Gly Arg Lys Val Met Gln Ile Tyr Leu |  |
|  | 35 40 45 |  |

| caa aag cac ttg caa aga ttc cca aaa ggg agg tgg gag aag cta gag | 964 |
|---|---|
| Gln Lys His Leu Gln Arg Phe Pro Lys Gly Arg Trp Glu Lys Leu Glu |  |
| 50 55 60 |  |

```
gtgagccggt ccaccctcac acactggaac gttcagcctt cttgttttca gctagagtca     1024
gattaacaga agtgacctaa cctgtggcca agatcaggtt ggcctcaaac tcgaaaagca     1084
aaacaaaaca acaaaaaagg aagtttgctg aaaaaaacaa aacaaacaa aagcaaaaac      1144 aaaaacaaaa aaccctgggg gggtatcgct agcaagcaag cctttagcct ttaatcccag     1204
cacttgggaa gcagaggcag gcagatttct gagttcgagg ccagcctggt ctacagagtg    1264
agttccagaa cagccagggc tacacagaga aaccctgtct tgaaactaac caccccccc     1324 caaaaaaagg aagtttgttg tacgtttgcg gtagaattct ttgaaggtat tttgttctct    1384
ggatggcagg aaaaggaagg gaggtggctt cgaacagttc attatagctc tgacctacaa   1444
ctgtaatccc agctcttaga ggtcaaggca ggagaatcag aaactcaagg ttatcctctg   1504
ctacatagtc agtttgaggc cagcctgggc tacatgagac cctatctcaa ataatagtgc   1564
aataaaatta ataataataa taatagctat ggtgatacca cttgaatatc ctctccacag   1624
```

| gat ggc tga gct ccc tga gag ccc aca tta tgc ccg ctg gca ttg gac | 1672 |
|---|---|
| Asp Gly  Ala Pro  Glu Pro Thr Leu Cys Pro Leu Ala Leu Asp |  |
| 65 70 75 |  |

| gtg ccc ggg ctg aac tct ttg aga agc aga tta tcc acc atg gcg gcc | 1720 |
|---|---|
| Val Pro Gly Leu Asn Ser Leu Arg Ser Arg Leu Ser Thr Met Ala Ala |  |
| 80 85 90 |  |

| agg tgt gct ctg ccc agg ccc cag gag tca ctc aca ttg tgg tgg atg | 1768 |
|---|---|
| Arg Cys Ala Leu Pro Arg Pro Gln Glu Ser Leu Thr Leu Trp Trp Met |  |
| 95 100 105 110 |  |

| aag aca tgg act atg agc ggg ctc tcc ggc tcc tca ggt tgc ccc agc | 1816 |
|---|---|
| Lys Thr Trp Thr Met Ser Gly Leu Ser Gly Ser Ser Gly Cys Pro Ser |  |
| 115 120 125 |  |

| tac ccc ctg gtg ccc agc tgg tga agt cca cct ggc tga gct tgt gcc | 1864 |
|---|---|
| Tyr Pro Leu Val Pro Ser Trp  Ser Pro Pro Gly  Ala Cys Ala |  |
| 130 135 140 |  |

| tgc agg agg gaa ggc tga cag aca cgg aag gat tca gcc ttc cca tgc | 1912 |
|---|---|
| Cys Arg Arg Glu Gly  Gln Thr Arg Lys Asp Ser Ala Phe Pro Cys |  |
| 145 150 155 |  |

| cca aga g gttggcagct ttagcctttt ctcaggtgtt tgttgatgat gtttgagttt | 1969 |
|---|---|
| Pro Arg |  |

-continued

```
ccatcttgag ttattgaaaa aaaaaacact cgtacttttt aaattggaca tatttggaaa      2029
ccaaggtttc tgtatagaga agattgggg tgggggtggg ggacagagac aggtaagaat       2089
ttgataccct aactctctgt gacctcccct gccctctagg tccttggatg aaccacagcc     2149
cagcaagtca ggccaagatg cttctgctcc tggcacccag cgggatttac ccaggaccac     2209
cctttctctt tccctcctc acaccagagc tgtatctcct cccccaacgg cagaaaagcc      2269
atcaagaacc caagcccagg tgaggagcct cccagcccag ggtgctgatc acagaaatgg     2329
aaggacctgg aggttagaca gaaaattcta ggtctctctc aattatgcac ctgtccatct     2389
cttcccaaca ttttcagtt ctgcattcaa ctagttatgt ctgccccagg ctggggtctt      2449
ttccttgagt caaagcagga gacgcctccc caccagacag cgctctcttc ttctatttgc     2509
```

| | | |
|---|---|---|
| ag ct cag ctc aga gga tga aac cag cga tgg aga agg gcc cca ggt<br>    Ala Gln Leu Arg Gly     Asn Gln Arg Trp Arg Arg Ala Pro Gly<br>           160                       165                170 | | 2555 |
| tag ctc agc aga tct gca agc ctt gat cac tgg gca cta ccc cac tcc<br>    Leu Ser Arg Ser Ala Ser Leu Asp His Trp Ala Leu Pro His Ser<br>        175                  180                  185 | | 2603 |
| ccc tga gga aga tgg tgg gcc tga ccc agc acc aga agc tct gga taa<br>Pro     Gly Arg Trp Trp Ala     Pro Ser Thr Arg Ser Ser Gly<br>               190                        195 | | 2651 |
| atg ggt ctg tgc aca gcc ctc gag cca gaa ggc aac taa cta caa tct<br>Met Gly Leu Cys Thr Ala Leu Glu Pro Glu Gly Asn     Leu Gln Ser<br>200                 205                 210 | | 2699 |
| gca cat cac aga gaa gct gga agt gct ggc taa agc cta cag tgt cca<br>Ala His His Arg Glu Ala Gly Ser Ala Gly     Ser Leu Gln Cys Pro<br>215                220                 225 | | 2747 |
| ggg aga caa gtg gag ggc cct ggg cta tgc aaa ggc cat caa tgc tct<br>Gly Arg Gln Val Glu Gly Pro Gly Leu Cys Lys Gly His Gln Cys Ser<br>230                235               240                245 | | 2795 |
| caa gag ctt cca caa gcc tgt cag ctc cta cca g gtacgtgggg<br>Gln Glu Leu Pro Gln Ala Cys Gln Leu Leu Pro<br>        250                  255 | | 2839 |

```
gaaggggtt gtttcttctt tactcagtac tggttacagc agcactagtc attaactagt      2899
ggttaactgt agtaccagt gggtgtccga cttagtgctt aagagtttat aatgagccga      2959
gcgtggtggc acacgccttt aatcccagca ctctggaggc agaggcaggc ggatttctga    3019
gttcaaggcc agcttggtct acaaagtgag ttccaggaca gccaggacta tacagagaaa   3079
ccctgtctca aaaaacaaa acaaacaaa acaaaaaaa aaaacaaaaa caaaaaaag       3139 agtttgtaat ggctgggatc tacatacaga gacaaactga tagaaggggg aggggaggaa    3199
aacagaccag cattaggact agaaaatggg tgcttagggg cttattacat acactgtttc   3259
ctctacatct gagtgtttta tatgataagt ttaaagccag gcgtggtggt tcatacgtta   3319
gactctgggg tccattgatt atggactcta ggcaagttag ttactctgtc agttttccaa   3379
tcactggaaa ggaatgaaca actataggcc attcacaggg gttttgtaag gttggaagat  3439
gatctcagta gcacagaatg acatagagta agccctcagg cagtgtggtg cagggagcct  3499
tcagtcaggc agtgtggtgc agtgagtccc cagtcaggca gtgctgtgac cccaacaggc   3559
agtgtcatgc agtgagcccc acccaggtca ggcagtgctg tgactccccc caaccccgc   3619 cccaggcagt gaggtatagt gagccctcag gtagtgtgat gcagtgggct cccagtcagg  3679
tagtgctgtg acccctccc ccaggcagtg tggtgcagtg agcctgcagt caggcagtgt    3739
ggtacaggga gccctaggc aagcagtgca gcgagacccc acacacacac acacacacac   3799
```

```
acatacacac acacacacac acacgctgca ggcaatacag tgggcccgca gggagtgtgc    3859
atgcagagtt gtgatgtggt ggtggcagtg gtggtggtga tgagcactgt cattttctct    3919
acctcttttt gtggttattt tgttttattt tttcttttag agacaagagt ctctctccac    3979
agccctgact gggctggaac tcacagatcc tctctctgcc tctgcctctg cctcctctgc    4039
ctctgccttt ctgcctctgc ctctgcctct gcctctgcct ctgcctctgc tctgcctctt    4099
gcctctgcct ctgcctctgc tctgcctctg cctctctgc ctctgcctct gcctctgcct    4159
ctgcctctgc tctgcctctt gcctctgcct ctgcctctct gcctctgcct ctctgcctct    4219
ctctgcctct gcctctgcct ctgcctctgc tctgcctctt gcctttctgc ctccaggagt    4279
tctgggattt aaggcctgcc aggccatttt ctctacttct tattgctggt tctgggaac    4339 caaaggacaa gctccatatg gttgctgggc tacctttggg gcagatattc tgctgaagga    4399
gccacattcc cctcttctgg ctctcccttc ctagcctctt cctcatcctc ctctgtgcca    4459
cttcctccct ag ga  ggc ctg tag cat ccc ggg aat tgg caa gcg gat ggc    4509
              Gly Gly Leu     His Pro Gly Asn Trp Gln Ala Asp Gly
                         260                     265 gga gaa ggt cat gga gat cct gga gag tgg gca tct gcg gaa gct aga      4557
Gly Glu Gly His Gly Asp Pro Gly Glu Trp Ala Ser Ala Glu Ala Arg
   270                 275                 280 cca cat cag tga cag tgt gcc tgt ctt gga gct ctt ctc caa cat ctg      4605
Pro His Gln     Gln Cys Ala Cys Leu Gly Ala Leu Leu Gln His Leu
285                 290                 295 ggg agc tgg gac gaa gac tgc cca gat gtg gta cca tca g gtcatgccag     4655
Gly Ser Trp Asp Glu Asp Cys Pro Asp Val Val Pro Ser
300                 305                 310 cccgcctgcc tcttaaagta ttgctgttac agagtctctg cccacacccc ttcctgttca    4715
cctgcaggaa tctgggtccc tctgttttcc caccctgggc cctcatggga gtgaaatcca    4775
actacaagga tgccagagtt cacattggtc cccctcctgt ccccagaaca gccatgtagc    4835
ttagtgtcct tgacctgtgg acagaaacaa taaatacatt actctgtccc acacaccagc    4895
agggatttgc tgttgttatg tttgtgtgtg tgtgtgtgtg tgtgtgtgtg                4955
tgtttgtgtg tgtgtgtgtg tgtttgtttt aaaaactata tgtcaccatg tagccctggc    5015
taacctagaa cttactatgt agaccaggct gatctgcctg gcttcagcaa gggactttct    5075
caggagccca ggctttgggc tccatgtctc gaacagtggc tctcaaactt ggccatgcca    5135
agaatgatct tgggagttag tgagcgtgaa gccctgaccc attttagacc gaggaatgag    5195
ggaccagcat gcccagatca cgtcccactg aatagaggct ggacttgatt ggtcctgcct    5255
tctgtcttcc atggcagctg ctgtgacagc cacccatgac ttctggcctg tttattagtc    5315
ctgggtcctc atagcctctt ttctggttgc tttcttccag gg  ctt ccg aaa cct     5369
                                              Gly Leu Pro Lys Pro
                                                         315 aga aga tct cca aag cct ggg ctc cct gac cgc tca gca ggc cat tgg      5417
Arg Arg Ser Pro Lys Pro Gly Leu Pro Asp Arg Ser Ala Gly His Trp
   320                 325                 330 ctt gaa gca cta cga tga ctt cct gga ccg cat gcc cag gga gga ggc      5465
Leu Glu Ala Leu Arg     Leu Pro Gly Pro His Ala Gln Gly Gly Gly
   335                 340                 345 tgc gga aat tga gca gac g gtaggcacag ctcgagccaa cagctcctga           5514
Cys Gly Asn     Ala Asp
       350 agccctagct gggcaacccc acaggcagcg gaagttaaga ggtcgacaga gattgtgtct    5574 accagagctg taggtccagg aaccccaggt ggggtgggca ctgcagtggc agccctctgg    5634
```

```
tctcagggtc actaagcatg aactctgggc actagtcgcc tagcatgggg caagcacagc    5694
ctcaaggcct gagtacaatc aaggcctgag tatgtcgttc agaggtagcg ctcctgagca    5754
tgcctaagac cctgcccatc ctcagcatca cagaaagggg gaaaaaaaaa acaaacaaaa    5814
aacatctagt tggccaagaa atcaggttta gccaagttaa aggttcagct tagagctagg    5874
ggctgagtct gtaagttcat gtgcagggtt gagtcaagag agacgggta taccagatgt    5934 ctgctatttg tatagtggca ttgggagcag gctggtacat gggcaggggt cttggtgagt    5994
gacagatgaa ccagtctgtt agcagaagga tcggagagac ctagtgagga agaataagcc    6054
tccaccagcg cccacagatg gaactatggg accggtgctg gatggataga cccatcacag    6114
agctgcggtg ctaatgcgga cccctgcact cagctacggt gtccgggcac agagaatgcc    6174
ctggtcagcc gccagctcct agcccatcag aagagaccgg cttccccact gcaggctgcc    6234
tgcaagcagg gctccagctg tagggattcc ggtgggattg ctcaaccaga cggcctcttc    6294
ccattctcct gggaggtcca agaagggatt gaagggacca gcagaactat gtcagggcaa    6354
ttggggtgtc ctggctgtga gcacccaggg ccctgaaac tgcagtgtcc tgcagagggg    6414
gcgggctagg tctctcaggt ccttctttaa caggccggcc tcacccctcc aagaacggtg    6474
tgggcagctc ctggcctccc cttcccacag gtgcagtggt atttcgtgct tcattttctc    6534
ccagccgggt tggaggctgt ctgccagcca cctgctcagg cctcgaccct gagcttccac    6594
acagccatca gctacaggct gcttgagctg catgggcgtg cctttgtga ttggcaggcc    6654 tttcacaggc ctggccactg gatgtgagtc gggggccaga acccacggag tgtcactcgg    6714
ctcttgcaca ggagccttct gctgaggcag agccaatgtc ctcaggcctc taacaggctt    6774
gcctctccag tgccccggca cgtcccctca gcttaatatg aatcccgggg gaaggctggg    6834
gcgaaggctg ggtgctgtcc tgggagaggc ctcagactct caccccctccc tgttcttccc    6894 cag gt    ccg gat atc agc cca ggc ctt caa ccc tgg gct gct gtg tgt     6941
    Gly Pro Asp Ile Ser Pro Gly Leu Gln Pro Trp Ala Ala Val Cys
        355             360                 365 ggc ttg tgg ctc tta ccg acg ggg gaa gat gac gtg cgg gga tgt gga     6989
Gly Leu Trp Leu Leu Pro Thr Gly Glu Asp Asp Val Arg Gly Cys Gly
370                 375                 380 tgt act cat tac tca ccc cga tgg ccg atc cca ccg ggg cat ctt cag     7037
Cys Thr His Tyr Ser Pro Arg Trp Pro Ile Pro Pro Gly His Leu Gln
385                 390                 395                 400 ctg cct cct tga tag cct tcg gca gca ag  gtatccattt tgactttggg        7086
Leu Pro Pro     Pro Ser Ala Ala Arg
                    405 tgagcaggct accagtgggc agccacctcc tagcagtcac ttccaagttc tcgatttgag    7146 acagactggg tgggaaaggg ctctgcaaga atcctacctc tcctgggcc aaagacaata     7206 aaacaggggc agatctcacc tgatgacact gcccgctttc cacagatgag gaattgggcc    7266 cagaggggcg aggccactca actcaacaca caaataggca cagggtatgc tgggaataaa    7326 gatcctcagg caacctgaga aggtgagact atcaggcctg ctccctgcc ctaccagaca    7386 tcccttgtgt tggaccag g gtt cct cac aga tga ctt ggt gag cca gga gga    7438
                    Val Pro His Arg     Leu Gly Glu Pro Gly Gly
                                410                 415 gaa cgg cca aca gca gaa ata cct ggg tgt gtg ccg gct ccc agg gcc     7486
Glu Arg Pro Thr Ala Glu Ile Pro Gly Cys Val Pro Ala Pro Arg Ala
    420                 425                 430 cgg gaa gcg cca ccg gcg act gga cat cat cgt ggt acc cta ctg tga    7534
Arg Glu Ala Pro Pro Ala Thr Gly His His Arg Gly Thr Leu Leu
```

```
                     435                 440                 445
gtt tgc ctg tgc cct gct cta ctt cac cgg ctc tgc cca ctt caa ccg    7582
Val Cys Leu Cys Pro Ala Leu Leu His Arg Leu Cys Pro Leu Gln Pro
450                 455                 460                 465 gtc cat gag agc tct ggc caa gac caa ggg cat gag cct gtc gga gca    7630
Val His Glu Ser Ser Gly Gln Asp Gln Gly His Glu Pro Val Gly Ala
                470                 475                 480 tgc gct cag tgc agc tgt agt ccg gaa cag cca agg tgt caa ggt ggg    7678
Cys Ala Gln Cys Ser Cys Ser Pro Glu Gln Pro Arg Cys Gln Gly Gly
            485                 490                 495 gcc tgg aca agt gct gcc cac ccc cac gga gaa gga cgt ctt caa gca    7726
Ala Trp Thr Ser Ala Ala His Pro His Gly Glu Gly Arg Leu Gln Ala
        500                 505                 510 ctt agg cct gcc cta ccg gga gcc agc tga acg gga ctg gtg acc tag    7774
Leu Arg Pro Ala Leu Pro Gly Ala Ser     Thr Gly Leu Val Thr
    515                 520                     525 gac ttg gag caa ggg gaa cca tgt tga atg aac tga ctc atg tag cca    7822
Asp Leu Glu Gln Gly Glu Pro Cys     Met Asn     Leu Met     Pro
530                 535                                     540 tct ccc acc ctc tta gct gtg cct cgc ttt gtc ggt tac gct tgc cct    7870
Ser Pro Thr Leu Leu Ala Val Pro Arg Phe Val Gly Tyr Ala Cys Pro
                545                 550                 555 gag tga cca agc tag gag ctt tgg gcc tgc ggg gaa gag cca gtc tga    7918
Glu     Pro Ser     Glu Leu Trp Ala Cys Gly Glu Glu Pro Val
                560                 565 ttc tga gag ccc gca agc tct ctc tcc tgg aca gga ttt atg ctg ctg    7966
Phe     Glu Pro Ala Ser Ser Leu Ser Trp Thr Gly Phe Met Leu Leu
570                 575                 580 tcc cct ctc ctc cca gtg aca ggt ttt cac acg gcc cct tcc ctg ttc    8014
Ser Pro Leu Leu Pro Val Thr Gly Phe His Thr Ala Pro Ser Leu Phe
585                 590                 595                 600 aag cag aac agg tgg ctg gtt tca agg cgg ttt cct gca ctg aag gcc    8062
Lys Gln Asn Arg Trp Leu Val Ser Arg Arg Phe Pro Ala Leu Lys Ala
                605                 610                 615 cga gct tcc ctt tcc acc cca aga ctg atg tag ctg tgt ggg gtc agc    8110
Arg Ala Ser Leu Ser Thr Pro Arg Leu Met     Leu Cys Gly Val Ser
                620                 625                 630 agg ggc tgc agg aga ggg aag cag ctg tgg gct cag cgt ctt ccg tga    8158
Arg Gly Cys Arg Arg Gly Lys Gln Leu Trp Ala Gln Arg Leu Pro
            635                 640                 645 gcc ttc aca gta gag aaa gcc atg tgg att ctc tca ccc gct cac ttc    8206
Ala Phe Thr Val Glu Lys Ala Met Trp Ile Leu Ser Pro Ala His Phe
        650                 655                 660 ctg tgc agc tgg agc tgc tgg ggg tgg cct gtc cag acc atg agg gtg    8254
Leu Cys Ser Trp Ser Cys Trp Gly Trp Pro Val Gln Thr Met Arg Val
    665                 670                 675 gct tct aag ggc cct ggg gcc taa taa agt gct tct gac att caa a     8300
Ala Ser Lys Gly Pro Gly Ala         Ser Ala Ser Asp Ile Gln
    680                 685                         690

<210> SEQ ID NO 4
<211> LENGTH: 2678
<212> TYPE: DNA
<213> ORGANISM: Homo sapiens
<220> FEATURE:
<221> NAME/KEY: CDS
<222> LOCATION: (372)..(2099)

<400> SEQUENCE: 4
ctgctggtaa gtggtctatt cctgcccacc cccgggtgac tagcttggcc agtagtcgac    60
```

-continued

```
cccacccggg gaccgactct gggggttgga gagactcttg gggccggggt cgggcactcc      120
agctttcttc tagccccgag ctgggattcc ctggcctgcg ccagctgcgt acacggcgag      180
tacaccgcac ctgcccggga cttcacccgc agctgcgaga ctcctccatt cccggagggc      240
tccccacacc tgctgcggcc gtgccccatc tccccgcagc tgcggcgctg agcaccccca      300
tgtcgagagg ctgagaccag gacagcagcc ctgaccaacg ctccaatagg ccgggatcca      360
gccatacttc a atg gat ccc agg ggt atc ttg aag gca ttt ccc aag cgg      410
            Met Asp Pro Arg Gly Ile Leu Lys Ala Phe Pro Lys Arg
              1               5                  10
```

| | | | | | | | | | | | | | | |
|---|---|---|---|---|---|---|---|---|---|---|---|---|---|---|
| cag | aaa | att | cat | gct | gat | gca | tca | tca | aaa | gta | ctt | gca | aag att cct | 458 |
| Gln | Lys | Ile | His | Ala | Asp | Ala | Ser | Ser | Lys | Val | Leu | Ala | Lys Ile Pro | |
| | 15 | | | | 20 | | | | 25 | | | | | |
| agg | agg | gaa | gag | gga | gaa | gaa | gca | gaa | gag | tgg | ctg | agc | tcc ctt cgg | 506 |
| Arg | Arg | Glu | Glu | Gly | Glu | Glu | Ala | Glu | Glu | Trp | Leu | Ser | Ser Leu Arg | |
| 30 | | | | 35 | | | | 40 | | | | 45 | | |
| gcc | cat | gtt | gtg | cgc | act | ggc | att | gga | cga | gcc | cgg | gca | gaa ctc ttt | 554 |
| Ala | His | Val | Val | Arg | Thr | Gly | Ile | Gly | Arg | Ala | Arg | Ala | Glu Leu Phe | |
| | | | | 50 | | | | | 55 | | | | 60 | |
| gag | aag | cag | att | gtt | cag | cat | ggc | ggc | cag | cta | tgc | cct | gcc cag ggc | 602 |
| Glu | Lys | Gln | Ile | Val | Gln | His | Gly | Gly | Gln | Leu | Cys | Pro | Ala Gln Gly | |
| | | | 65 | | | | 70 | | | | | 75 | | |
| cca | ggt | gtc | act | cac | att | gtg | gtg | gat | gaa | ggc | atg | gac | tat gag cga | 650 |
| Pro | Gly | Val | Thr | His | Ile | Val | Val | Asp | Glu | Gly | Met | Asp | Tyr Glu Arg | |
| | | 80 | | | | | 85 | | | | | 90 | | |
| gcc | ctc | cgc | ctt | ctc | aga | cta | ccc | cag | ctg | ccc | ccg | ggt | gct cag ctg | 698 |
| Ala | Leu | Arg | Leu | Leu | Arg | Leu | Pro | Gln | Leu | Pro | Pro | Gly | Ala Gln Leu | |
| | 95 | | | | 100 | | | | | 105 | | | | |
| gtg | aag | tca | gcc | tgg | ctg | agc | ttg | tgc | ctt | cag | gag | agg | agg ctg gtg | 746 |
| Val | Lys | Ser | Ala | Trp | Leu | Ser | Leu | Cys | Leu | Gln | Glu | Arg | Arg Leu Val | |
| 110 | | | | | 115 | | | | | 120 | | | | 125 |
| gat | gta | gct | gga | ttc | agc | atc | ttc | atc | ccc | agt | agg | tac | ttg gac cat | 794 |
| Asp | Val | Ala | Gly | Phe | Ser | Ile | Phe | Ile | Pro | Ser | Arg | Tyr | Leu Asp His | |
| | | | | 130 | | | | | 135 | | | | | 140 |
| cca | cag | ccc | agc | aag | gca | gag | cag | gat | gct | tct | att | cct | cct ggc acc | 842 |
| Pro | Gln | Pro | Ser | Lys | Ala | Glu | Gln | Asp | Ala | Ser | Ile | Pro | Pro Gly Thr | |
| | | | 145 | | | | | 150 | | | | | 155 | |
| cat | gag | gcc | ctg | ctt | cag | aca | gcc | ctt | tct | cct | cct | cct | cct ccc acc | 890 |
| His | Glu | Ala | Leu | Leu | Gln | Thr | Ala | Leu | Ser | Pro | Pro | Pro | Pro Pro Thr | |
| | | 160 | | | | | 165 | | | | | 170 | | |
| agg | cct | gtg | tct | cct | ccc | caa | aag | gca | aaa | gag | gca | cca | aac acc caa | 938 |
| Arg | Pro | Val | Ser | Pro | Pro | Gln | Lys | Ala | Lys | Glu | Ala | Pro | Asn Thr Gln | |
| | 175 | | | | | 180 | | | | | 185 | | | |
| gcc | cag | ccc | atc | tct | gat | gat | gaa | gcc | agt | gat | ggg | gaa | gaa acc cag | 986 |
| Ala | Gln | Pro | Ile | Ser | Asp | Asp | Glu | Ala | Ser | Asp | Gly | Glu | Glu Thr Gln | |
| 190 | | | | 195 | | | | | 200 | | | | | 205 |
| gtt | agt | gca | gct | gat | ctg | gaa | gcc | ctc | atc | agt | ggc | cac | tac ccc acc | 1034 |
| Val | Ser | Ala | Ala | Asp | Leu | Glu | Ala | Leu | Ile | Ser | Gly | His | Tyr Pro Thr | |
| | | | | 210 | | | | | 215 | | | | | 220 |
| tcc | ctt | gag | gga | gat | tgt | gag | cct | agc | cca | gcc | cct | gct | gtc ctg gat | 1082 |
| Ser | Leu | Glu | Gly | Asp | Cys | Glu | Pro | Ser | Pro | Ala | Pro | Ala | Val Leu Asp | |
| | | | 225 | | | | | 230 | | | | | 235 | |
| aag | tgg | gtc | tgt | gca | cag | ccc | tca | agc | cag | aag | gcg | acc | aat cac aac | 1130 |
| Lys | Trp | Val | Cys | Ala | Gln | Pro | Ser | Ser | Gln | Lys | Ala | Thr | Asn His Asn | |
| | | 240 | | | | | 245 | | | | | 250 | | |
| ctc | cat | atc | aca | gag | aag | ctg | gaa | gtt | ctg | gcc | aaa | gcc | tac agt gtt | 1178 |
| Leu | His | Ile | Thr | Glu | Lys | Leu | Glu | Val | Leu | Ala | Lys | Ala | Tyr Ser Val | |
| | 255 | | | | | 260 | | | | | 265 | | | |
| cag | gga | gac | aag | tgg | agg | gcc | ctg | ggc | tat | gcc | aag | gcc | atc aat gcc | 1226 |

```
                                      -continued

Gln Gly Asp Lys Trp Arg Ala Leu Gly Tyr Ala Lys Ala Ile Asn Ala
270                 275                 280                 285 ctc aag agc ttc cat aag cct gtc acc tcg tac cag gag gcc tgc agt         1274
Leu Lys Ser Phe His Lys Pro Val Thr Ser Tyr Gln Glu Ala Cys Ser
                290                 295                 300 atc cct ggg att ggg aag cgg atg gct gag aaa atc ata gag atc ctg         1322
Ile Pro Gly Ile Gly Lys Arg Met Ala Glu Lys Ile Ile Glu Ile Leu
            305                 310                 315 gag agc ggg cat ttg cgg aag ctg gac cat atc agt gag agc gtg cct         1370
Glu Ser Gly His Leu Arg Lys Leu Asp His Ile Ser Glu Ser Val Pro
        320                 325                 330 gtc ttg gag ctc ttc tcc aac atc tgg gga gct ggg acc aag act gcc         1418
Val Leu Glu Leu Phe Ser Asn Ile Trp Gly Ala Gly Thr Lys Thr Ala
    335                 340                 345 cag atg tgg tac caa cag ggc ttc cga agt ctg gaa gac atc cgc agc         1466
Gln Met Trp Tyr Gln Gln Gly Phe Arg Ser Leu Glu Asp Ile Arg Ser
350                 355                 360                 365 cag gcc tcc ctg aca acc cag cag gcc atc ggc ctg aag cat tac agt         1514
Gln Ala Ser Leu Thr Thr Gln Gln Ala Ile Gly Leu Lys His Tyr Ser
                370                 375                 380 gac ttc ctg gaa cgt atg ccc agg gag gag gct aca gag att gag cag         1562
Asp Phe Leu Glu Arg Met Pro Arg Glu Glu Ala Thr Glu Ile Glu Gln
            385                 390                 395 aca gtc cag aaa gca gcc cag gcc ttt aac tct ggg ctg ctg tgt             1610
Thr Val Gln Lys Ala Ala Gln Ala Phe Asn Ser Gly Leu Leu Cys Val
        400                 405                 410 gca tgt ggt tca tac cga cgg gga aag gcg acc tgt ggt gat gtc gac         1658
Ala Cys Gly Ser Tyr Arg Arg Gly Lys Ala Thr Cys Gly Asp Val Asp
    415                 420                 425 gtg ctc atc act cac cca gat ggc cgg tcc cac cgg ggt atc ttc agc         1706
Val Leu Ile Thr His Pro Asp Gly Arg Ser His Arg Gly Ile Phe Ser
430                 435                 440                 445 cgc ctc ctt gac agt ctt cgg cag gaa ggg ttc ctc aca gat gac ttg         1754
Arg Leu Leu Asp Ser Leu Arg Gln Glu Gly Phe Leu Thr Asp Asp Leu
                450                 455                 460 gtg agc caa gag gag aat ggt cag caa cag aag tac ttg ggg gtg tgc         1802
Val Ser Gln Glu Glu Asn Gly Gln Gln Gln Lys Tyr Leu Gly Val Cys
            465                 470                 475 cgg ctc cca ggg cca ggg cgg cgg cac cgg cgc ctg gac atc atc gtg         1850
Arg Leu Pro Gly Pro Gly Arg Arg His Arg Arg Leu Asp Ile Ile Val
        480                 485                 490 gtg ccc tat agc gag ttt gcc tgt gcc ctg ctc tac ttc acc ggc tct         1898
Val Pro Tyr Ser Glu Phe Ala Cys Ala Leu Leu Tyr Phe Thr Gly Ser
    495                 500                 505 gca cac ttc aac cgc tcc atg cga gcc ctg gcc aaa acc aag ggc atg         1946
Ala His Phe Asn Arg Ser Met Arg Ala Leu Ala Lys Thr Lys Gly Met
510                 515                 520                 525 agt ctg tca gaa cat gcc ctc agc act gct gtg gtc cgg aac acc cat         1994
Ser Leu Ser Glu His Ala Leu Ser Thr Ala Val Val Arg Asn Thr His
                530                 535                 540 ggc tgc aag gtg ggg cct ggc cga gtg ctg ccc act ccc act gag aag         2042
Gly Cys Lys Val Gly Pro Gly Arg Val Leu Pro Thr Pro Thr Glu Lys
            545                 550                 555 gat gtc ttc agg ctc tta ggc ctc ccc tac cga gaa cct gct gag cgg         2090
Asp Val Phe Arg Leu Leu Gly Leu Pro Tyr Arg Glu Pro Ala Glu Arg
        560                 565                 570 gac tgg tga cccatggctg ggggtgctga ggagagccga gttggactgg                 2139
Asp Trp
575
```

-continued

```
ctaccnctcc tggccaccca gtactccctc cagcctcagc tggctgaacc tcgccgctcc   2199
aaccaccagc ttcctcagcg agcagggccc agggctctgg gcctgaagca agagccagcc   2259
cggctcccag tgtctgcccg gctcccagtg tctgcccagc cctctcccag acaggagcag   2319
gctgccaccc cttctacctc accactgccc ctcgaagaat tttgcaaatg cccccttgcc   2379
ccattttaag caggagcagg tggctggttt gaagccccag gtatccccct tccctgctat   2439
gggaaaggcc aagctgctgg gtggggacag aagctgcagg ggagagggaa gcagccgtgc   2499
tgtcaacatc atccggcacc ctctggggta ggagaacagc cattccacat gtgttccctc   2559
tatccgtcct gcttcctggg cagctggtgg tgctgggaat ggggtgcccc agccttggtg   2619
aggacagtgt tgggaggccc aggggcccag taaagtgcat ttgacattga aaaaaaaaa   2678
```

<210> SEQ ID NO 5
<211> LENGTH: 575
<212> TYPE: PRT
<213> ORGANISM: Homo sapiens

<400> SEQUENCE: 5

```
Met Asp Pro Arg Gly Ile Leu Lys Ala Phe Pro Lys Arg Gln Lys Ile
  1               5                  10                  15

His Ala Asp Ala Ser Ser Lys Val Leu Ala Lys Ile Pro Arg Arg Glu
             20                  25                  30

Glu Gly Glu Glu Ala Glu Glu Trp Leu Ser Ser Leu Arg Ala His Val
         35                  40                  45

Val Arg Thr Gly Ile Gly Arg Ala Arg Ala Glu Leu Phe Glu Lys Gln
     50                  55                  60

Ile Val Gln His Gly Gly Gln Leu Cys Pro Ala Gln Gly Pro Gly Val
 65                  70                  75                  80

Thr His Ile Val Val Asp Glu Gly Met Asp Tyr Glu Arg Ala Leu Arg
                 85                  90                  95

Leu Leu Arg Leu Pro Gln Leu Pro Pro Gly Ala Gln Leu Val Lys Ser
            100                 105                 110

Ala Trp Leu Ser Leu Cys Leu Gln Glu Arg Arg Leu Val Asp Val Ala
        115                 120                 125

Gly Phe Ser Ile Phe Ile Pro Ser Arg Tyr Leu Asp His Pro Gln Pro
    130                 135                 140

Ser Lys Ala Glu Gln Asp Ala Ser Ile Pro Pro Gly Thr His Glu Ala
145                 150                 155                 160

Leu Leu Gln Thr Ala Leu Ser Pro Pro Pro Pro Thr Arg Pro Val
                165                 170                 175

Ser Pro Pro Gln Lys Ala Lys Glu Ala Pro Asn Thr Gln Ala Gln Pro
            180                 185                 190

Ile Ser Asp Asp Glu Ala Ser Asp Gly Glu Glu Thr Gln Val Ser Ala
        195                 200                 205

Ala Asp Leu Glu Ala Leu Ile Ser Gly His Tyr Pro Thr Ser Leu Glu
    210                 215                 220

Gly Asp Cys Glu Pro Ser Pro Ala Pro Ala Val Leu Asp Lys Trp Val
225                 230                 235                 240

Cys Ala Gln Pro Ser Ser Gln Lys Ala Thr Asn His Asn Leu His Ile
                245                 250                 255

Thr Glu Lys Leu Glu Val Leu Ala Lys Ala Tyr Ser Val Gln Gly Asp
            260                 265                 270

Lys Trp Arg Ala Leu Gly Tyr Ala Lys Ala Ile Asn Ala Leu Lys Ser
        275                 280                 285
```

```
Phe His Lys Pro Val Thr Ser Tyr Gln Glu Ala Cys Ser Ile Pro Gly
    290                 295                 300
Ile Gly Lys Arg Met Ala Glu Lys Ile Ile Glu Ile Leu Glu Ser Gly
305                 310                 315                 320
His Leu Arg Lys Leu Asp His Ile Ser Glu Ser Val Pro Val Leu Glu
                325                 330                 335
Leu Phe Ser Asn Ile Trp Gly Ala Gly Thr Lys Thr Ala Gln Met Trp
            340                 345                 350
Tyr Gln Gln Gly Phe Arg Ser Leu Glu Asp Ile Arg Ser Gln Ala Ser
        355                 360                 365
Leu Thr Thr Gln Gln Ala Ile Gly Leu Lys His Tyr Ser Asp Phe Leu
    370                 375                 380
Glu Arg Met Pro Arg Glu Ala Thr Glu Ile Glu Gln Thr Val Gln
385                 390                 395                 400
Lys Ala Ala Gln Ala Phe Asn Ser Gly Leu Leu Cys Val Ala Cys Gly
                405                 410                 415
Ser Tyr Arg Arg Gly Lys Ala Thr Cys Gly Asp Val Asp Val Leu Ile
            420                 425                 430
Thr His Pro Asp Gly Arg Ser His Arg Gly Ile Phe Ser Arg Leu Leu
        435                 440                 445
Asp Ser Leu Arg Gln Glu Gly Phe Leu Thr Asp Leu Val Ser Gln
    450                 455                 460
Glu Glu Asn Gly Gln Gln Gln Lys Tyr Leu Gly Val Cys Arg Leu Pro
465                 470                 475                 480
Gly Pro Gly Arg Arg His Arg Arg Leu Asp Ile Ile Val Val Pro Tyr
                485                 490                 495
Ser Glu Phe Ala Cys Ala Leu Leu Tyr Phe Thr Gly Ser Ala His Phe
            500                 505                 510
Asn Arg Ser Met Arg Ala Leu Ala Lys Thr Lys Gly Met Ser Leu Ser
        515                 520                 525
Glu His Ala Leu Ser Thr Ala Val Val Arg Asn Thr His Gly Cys Lys
    530                 535                 540
Val Gly Pro Gly Arg Val Leu Pro Thr Pro Thr Glu Lys Asp Val Phe
545                 550                 555                 560
Arg Leu Leu Gly Leu Pro Tyr Arg Glu Pro Ala Glu Arg Asp Trp
                565                 570                 575

<210> SEQ ID NO 6
<211> LENGTH: 720
<212> TYPE: DNA
<213> ORGANISM: Homo sapiens

<400> SEQUENCE: 6 cagggtatc ttgaaggcat ttcccaagcg gcagaaaatt catgctgatg catcatcaaa     60
agtacttgca aagattccta ggagggaaga gggagaagaa gcagaagagt ggctgagctc    120
ccttcgggcc catgttgtgc gcactggcat tggacgagcc cgggcagaac tctttgagaa    180
gcagattgtt cagcatggcg ccagctatg ccctgcccag ggcccaggtg tcactcacat     240
tgtggtggat gaaggcatgg actatgagcg agccctccgc cttctcagac taccccagct    300
gcccccgggt gctcagctgg tgaagtcagc ctggctgagc ttgtgccttc aggagaggag    360
gctggtggat gtagctggat tcagcatctt catcccagt aggtacttgg accatccaca     420
gcccagcaag gcagagcagg atgcttctat tcctcctggc acccatgagg ccctgcttca    480
```

-continued

```
gacagccctt tctcctcctc ctcctcccac caggcctgtg tctcctcccc aaaaggcaaa      540
agaggcacca aacacccaag cccagcccat ctctgatgat gaagccagtg atggggaaga      600
aacccaggag gcctgcagta tccctgggat tgggaagcgg atggctgaga aaatcataga      660
gatcctggag agcgggcatt tgcggaagct ggaccatatc agtgagagcg tgcctgtctt      720
```

<210> SEQ ID NO 7
<211> LENGTH: 239
<212> TYPE: PRT
<213> ORGANISM: Homo sapiens

<400> SEQUENCE: 7

```
Arg Gly Ile Leu Lys Ala Phe Pro Lys Arg Gln Lys Ile His Ala Asp
1               5                   10                  15

Ala Ser Ser Lys Val Leu Ala Lys Ile Pro Arg Arg Glu Glu Gly Glu
            20                  25                  30

Glu Ala Glu Glu Trp Leu Ser Ser Leu Arg Ala His Val Val Arg Thr
        35                  40                  45

Gly Ile Gly Arg Ala Arg Ala Glu Leu Phe Glu Lys Gln Ile Val Gln
    50                  55                  60

His Gly Gly Gln Leu Cys Pro Ala Gln Gly Pro Gly Val Thr His Ile
65                  70                  75                  80

Val Val Asp Glu Gly Met Asp Tyr Glu Arg Ala Leu Arg Leu Leu Arg
                85                  90                  95

Leu Pro Gln Leu Pro Pro Gly Ala Gln Leu Val Lys Ser Ala Trp Leu
            100                 105                 110

Ser Leu Cys Leu Gln Glu Arg Arg Leu Val Asp Val Ala Gly Phe Ser
        115                 120                 125

Ile Phe Ile Pro Ser Arg Tyr Leu Asp His Pro Gln Pro Ser Lys Ala
    130                 135                 140

Glu Gln Asp Ala Ser Ile Pro Pro Gly Thr His Glu Ala Leu Leu Gln
145                 150                 155                 160

Thr Ala Leu Ser Pro Pro Pro Pro Thr Arg Pro Val Ser Pro Pro
                165                 170                 175

Gln Lys Ala Lys Glu Ala Pro Asn Thr Gln Ala Gln Pro Ile Ser Asp
            180                 185                 190

Asp Glu Ala Ser Asp Gly Glu Glu Thr Gln Glu Ala Cys Ser Ile Pro
        195                 200                 205

Gly Ile Gly Lys Arg Met Ala Glu Lys Ile Ile Glu Ile Leu Glu Ser
    210                 215                 220

Gly His Leu Arg Lys Leu Asp His Ile Ser Glu Ser Val Pro Val
225                 230                 235
```

<210> SEQ ID NO 8
<211> LENGTH: 657
<212> TYPE: DNA
<213> ORGANISM: Homo sapiens

<400> SEQUENCE: 8

```
tccataagcc tgtcacctcg taccagggct tccgaagtct ggaagacatc cgcagccagg      60
cctccctgac aacccagcag gccatcggcc tgaagcatta cagtgacttc ctggaacgta     120
tgcccaggga ggaggctaca gagattgagc agacagtcca gaaagcagcc caggccttta     180
actccgggct gctgtgtgtg gcatgtggtt cataccgacg gggaaaggcg acctgtggtg     240
atgtcgacgt gctcatcact cacccagatg gccggtccca ccggggtatc ttcagccgcc     300
```

```
tccttgacag tcttcggcag gaagggttcc tcacagatga cttggtgagc caagaggaga    360
atggtcagca acagaagtac ttgggggtgt gccggctccc agggccaggg cggcggcacc    420
ggcgcctgga catcatcgtg gtgccctata gcgagtttgc ctgtgccctg ctctacttca    480
ccggctctgc acacttcaac cgctccatgc gagccctggc caaaaccaag ggcatgagtc    540
tgtcagaaca tgccctcagc actgctgtgg tccggaacac ccatggctgc aaggtggggc    600
ctggccgagt gctgcccact cccactgaga aggatgtctt caggctctta ggcctcc      657

<210> SEQ ID NO 9
<211> LENGTH: 77
<212> TYPE: PRT
<213> ORGANISM: Homo sapiens

<400> SEQUENCE: 9

His Lys Pro Val Thr Ser Tyr Gln Gly Phe Arg Ser Leu Glu Asp Ile
1               5                   10                  15

Arg Ser Gln Asn Ser Gly Leu Leu Cys Val Ala Cys Gly Ser Tyr Arg
            20                  25                  30

Arg Gly Lys Ala Thr Cys Glu Asn Gly Gln Gln Gln Lys Tyr Leu Gly
        35                  40                  45

Val Cys Arg Leu Pro Gly Pro Gly Arg Lys Met Ser Leu Ser Glu His
    50                  55                  60

Ala Leu Ser Thr Ala Val Val Arg Asn Thr His Gly Cys
65                  70                  75

<210> SEQ ID NO 10
<211> LENGTH: 528
<212> TYPE: DNA
<213> ORGANISM: Homo sapiens

<400> SEQUENCE: 10
tccataagcc tgtcacctcg taccaggtcc agaaagcagc ccaggccttt aactctgggc     60
tgctgtgtgt ggcatgtggt tcataccgac ggggaaaggc gacctgtggt gatgtcgacg    120
tgctcatcac tcacccagat ggccggtccc accggggtat cttcagccgc tccttgaca    180 gtcttcggca ggaagggttc ctcacagatg acttggtgag ccaagaggag aatggtcagc    240
aacagaagta cttgggggtg tgccggctcc agggccaggg cggcggcacc ggcgcctgg    300 acatcatcgt ggtgccctat agcgagtttg cctgtgccct gctctacttc accggctctg    360
cacacttcaa ccgctccatg cgagccctgg ccaaaaccaa gggcatgagt ctgtcagaac    420
atgccctcag cactgctgtg gtccggaaca cccatggctg caaggtgggg cctggccgag    480
tgctgcccac tcccactgag aaggatgtct tcaggctctt aggcctcc                528

<210> SEQ ID NO 11
<211> LENGTH: 175
<212> TYPE: PRT
<213> ORGANISM: Homo sapiens

<400> SEQUENCE: 11

His Lys Pro Val Thr Ser Tyr Gln Val Gln Lys Ala Ala Gln Ala Phe
1               5                   10                  15

Asn Ser Gly Leu Leu Cys Val Ala Cys Gly Ser Tyr Arg Arg Gly Lys
            20                  25                  30

Ala Thr Cys Gly Asp Val Asp Val Leu Ile Thr His Pro Asp Gly Arg
        35                  40                  45

Ser His Arg Gly Ile Phe Ser Arg Leu Leu Asp Ser Leu Arg Gln Glu
```

-continued

```
                    50                  55                  60
Gly Phe Leu Thr Asp Asp Leu Val Ser Gln Glu Glu Asn Gly Gln Gln
 65                  70                  75                  80

Gln Lys Tyr Leu Gly Val Cys Arg Leu Pro Gly Pro Gly Arg Arg His
                 85                  90                  95

Arg Arg Leu Asp Ile Ile Val Val Pro Tyr Ser Glu Phe Ala Cys Ala
                100                 105                 110

Leu Leu Tyr Phe Thr Gly Ser Ala His Phe Asn Arg Ser Met Arg Ala
                115                 120                 125

Leu Ala Lys Thr Lys Gly Met Ser Leu Ser Glu His Ala Leu Ser Thr
130                 135                 140

Ala Val Val Arg Asn Thr His Gly Cys Lys Val Gly Pro Gly Arg Val
145                 150                 155                 160

Leu Pro Thr Pro Thr Glu Lys Asp Val Phe Arg Leu Leu Gly Leu
                165                 170                 175

<210> SEQ ID NO 12

<400> SEQUENCE: 12

000

<210> SEQ ID NO 13
<211> LENGTH: 27
<212> TYPE: DNA
<213> ORGANISM: Homo sapiens

<400> SEQUENCE: 13
actcacccag atggccggtc ccaccgg                                         27

<210> SEQ ID NO 14
<211> LENGTH: 27
<212> TYPE: DNA
<213> ORGANISM: Homo sapiens

<400> SEQUENCE: 14
actcacccag atggctggtc ccaccgg                                         27

<210> SEQ ID NO 15
<211> LENGTH: 9
<212> TYPE: PRT
<213> ORGANISM: Homo sapiens

<400> SEQUENCE: 15

Thr His Pro Asp Gly Arg Ser His Arg
 1               5

<210> SEQ ID NO 16
<211> LENGTH: 9
<212> TYPE: PRT
<213> ORGANISM: Homo sapiens

<400> SEQUENCE: 16

Thr His Pro Asp Gly Trp Ser His Arg
 1               5

<210> SEQ ID NO 17
<211> LENGTH: 44
<212> TYPE: DNA
<213> ORGANISM: Homo sapiens

<400> SEQUENCE: 17
```
ccctctatcc gtcctgcttc ctgggcagct ggtggtgctg ggaa         44

<210> SEQ ID NO 18
<211> LENGTH: 44
<212> TYPE: DNA
<213> ORGANISM: Homo sapiens

<400> SEQUENCE: 18
ccctctatcc gtcctgcttc ctgggcagct ggtggtgctg ggaa         44

<210> SEQ ID NO 19
<211> LENGTH: 44
<212> TYPE: DNA
<213> ORGANISM: Homo sapiens

<400> SEQUENCE: 19
ccctctatcc gtcctgcttc ctgggcagct ggtggtgctg ggaa         44

<210> SEQ ID NO 20
<211> LENGTH: 44
<212> TYPE: DNA
<213> ORGANISM: Homo sapiens

<400> SEQUENCE: 20
ccctctatcc gtcctgcttc ctgggcagct ggtggtgctg ggaa         44

<210> SEQ ID NO 21
<211> LENGTH: 44
<212> TYPE: DNA
<213> ORGANISM: Homo sapiens

<400> SEQUENCE: 21
ccctctatcc gtcctgcttc ctgggcagct ggtggtgctg ggaa         44

<210> SEQ ID NO 22
<211> LENGTH: 44
<212> TYPE: DNA
<213> ORGANISM: Homo sapiens

<400> SEQUENCE: 22
ccctctatcc gtcctgcttc ctgggcagct ggtggtgctg ggaa         44

<210> SEQ ID NO 23
<211> LENGTH: 44
<212> TYPE: DNA
<213> ORGANISM: Homo sapiens

<400> SEQUENCE: 23
ccctctatcc gtcctgcttc ctgggcagct ggtggtgctg ggaa         44

<210> SEQ ID NO 24
<211> LENGTH: 44
<212> TYPE: DNA
<213> ORGANISM: Homo sapiens

<400> SEQUENCE: 24
ccctctatcc gtcctgcttc ctgggcagct ggtggtgctg ggaa         44

<210> SEQ ID NO 25
<211> LENGTH: 44
<212> TYPE: DNA
<213> ORGANISM: Homo sapiens

```
<400> SEQUENCE: 25
ccctctatcc gtcctgcttc ctgggcagct ggtggtgctg ggaa                    44

<210> SEQ ID NO 26
<211> LENGTH: 44
<212> TYPE: DNA
<213> ORGANISM: Homo sapiens

<400> SEQUENCE: 26
ccctctatcc gtcctgcttc ctgggcagct ggtggtgctg ggaa                    44

<210> SEQ ID NO 27
<211> LENGTH: 44
<212> TYPE: DNA
<213> ORGANISM: Homo sapiens

<400> SEQUENCE: 27
ccctctatcc gtcctgcttc ctgggcagct ggtggtgctg ggaa                    44

<210> SEQ ID NO 28
<211> LENGTH: 44
<212> TYPE: DNA
<213> ORGANISM: Homo sapiens

<400> SEQUENCE: 28
ccctctatcc gtcctgcttc ctgggcagct ggtggtgctg ggaa                    44

<210> SEQ ID NO 29
<211> LENGTH: 44
<212> TYPE: DNA
<213> ORGANISM: Homo sapiens

<400> SEQUENCE: 29
ccctctatcc gtcctgcttc ctgggcagct ggtggtgctg ggaa                    44

<210> SEQ ID NO 30
<211> LENGTH: 44
<212> TYPE: DNA
<213> ORGANISM: Homo sapiens

<400> SEQUENCE: 30
ccctctatcc gtcctgcttc ccggtcagct ggtggtgctg ggaa                    44

<210> SEQ ID NO 31
<211> LENGTH: 44
<212> TYPE: DNA
<213> ORGANISM: Homo sapiens

<400> SEQUENCE: 31
ccctctatcc gtcctgcttc ccggtcagct ggtggtgctg ggaa                    44

<210> SEQ ID NO 32
<211> LENGTH: 44
<212> TYPE: DNA
<213> ORGANISM: Homo sapiens

<400> SEQUENCE: 32
ccctctatcc gtcctgcttc ccggtcagct ggtggtgctg ggaa                    44

<210> SEQ ID NO 33
<211> LENGTH: 44
<212> TYPE: DNA
<213> ORGANISM: Homo sapiens
```

-continued

<400> SEQUENCE: 33
ccctctatcc gtcctgcttc ccggtcagct ggtggtgctg ggaa                         44

<210> SEQ ID NO 34
<211> LENGTH: 44
<212> TYPE: DNA
<213> ORGANISM: Homo sapiens

<400> SEQUENCE: 34
ccctctatcc gtcctgcttc ccggtcagct ggtggtgctg ggaa                         44

<210> SEQ ID NO 35
<211> LENGTH: 44
<212> TYPE: DNA
<213> ORGANISM: Homo sapiens

<400> SEQUENCE: 35
ccctctatcc gtcctgcttc ccggtcagct ggtggtgctg ggaa                         44

<210> SEQ ID NO 36
<211> LENGTH: 44
<212> TYPE: DNA
<213> ORGANISM: Homo sapiens

<400> SEQUENCE: 36
ccctctatcc gtcctgcttc ccggtcagct ggtggtgctg ggaa                         44

<210> SEQ ID NO 37
<211> LENGTH: 37
<212> TYPE: DNA
<213> ORGANISM: Artificial sequence
<220> FEATURE:
<223> OTHER INFORMATION: polydT

<400> SEQUENCE: 37
tttttttttt tttttttttt tttttttttt ttttttt                                 37

<210> SEQ ID NO 38
<211> LENGTH: 15
<212> TYPE: DNA
<213> ORGANISM: Artificial sequence
<220> FEATURE:
<223> OTHER INFORMATION: polydA

<400> SEQUENCE: 38
aaaaaaaaaa aaaaa                                                         15

<210> SEQ ID NO 39
<211> LENGTH: 2402
<212> TYPE: DNA
<213> ORGANISM: Homo sapiens
<220> FEATURE:
<221> NAME/KEY: CDS
<222> LOCATION: (372)..(1823)

<400> SEQUENCE: 39
ctgctggtaa gtggtctatt cctgcccacc ccgggtgac tagcttggcc agtagtcgac          60
cccacccggg gaccgactct gggggttgga gagactcttg gggccgggt cgggcactcc         120 agctttcttc tagccccgag ctgggattcc ctggcctgcg ccagctgcgt acacggcgag        180
tacaccgcac ctgccgggga cttcacccgc agctgcgaga ctcctccatt cccggagggc        240
tccccacacc tgctgcggcc gtgccccatc tccccgcagc tgcggcgctg agcacccca         300

```
tgtcgagagg ctgagaccag acagcagcc ctgaccaacg ctccaatagg ccgggatcca        360
gccatacttc a atg gat ccc agg ggt atc ttg aag gca ttt ccc aag cgg        410
            Met Asp Pro Arg Gly Ile Leu Lys Ala Phe Pro Lys Arg
              1               5                  10 cag aaa att cat gct gat gca tca tca aaa gta ctt gca aag att cct        458
Gln Lys Ile His Ala Asp Ala Ser Ser Lys Val Leu Ala Lys Ile Pro
 15              20                  25 agg agg gaa gag gga gaa gaa gca gaa gag tgg ctg agc tcc ctt cgg        506
Arg Arg Glu Glu Gly Glu Glu Ala Glu Glu Trp Leu Ser Ser Leu Arg
 30              35                  40                  45 gcc cat gtt gtg cgc act ggc att gga cga gcc cgg gca gaa ctc ttt        554
Ala His Val Val Arg Thr Gly Ile Gly Arg Ala Arg Ala Glu Leu Phe
                 50                  55                  60 gag aag cag att gtt cag cat ggc ggc cag cta tgc cct gcc cag ggc        602
Glu Lys Gln Ile Val Gln His Gly Gly Gln Leu Cys Pro Ala Gln Gly
                 65                  70                  75 cca ggt gtc act cac att gtg gtg gat gaa ggc atg gac tat gag cga        650
Pro Gly Val Thr His Ile Val Val Asp Glu Gly Met Asp Tyr Glu Arg
         80                  85                  90 gcc ctc cgc ctt ctc aga cta ccc cag ctg ccc ccg ggt gct cag ctg        698
Ala Leu Arg Leu Leu Arg Leu Pro Gln Leu Pro Pro Gly Ala Gln Leu
 95                 100                 105 gtg aag tca gcc tgg ctg agc ttg tgc ctt cag gag agg agg ctg gtg        746
Val Lys Ser Ala Trp Leu Ser Leu Cys Leu Gln Glu Arg Arg Leu Val
110             115                 120                 125 gat gta gct gga ttc agc atc ttc atc ccc agt agg tac ttg gac cat        794
Asp Val Ala Gly Phe Ser Ile Phe Ile Pro Ser Arg Tyr Leu Asp His
                130                 135                 140 cca cag ccc agc aag gca gag cag gat gct tct att cct cct ggc acc        842
Pro Gln Pro Ser Lys Ala Glu Gln Asp Ala Ser Ile Pro Pro Gly Thr
                145                 150                 155 cat gag gcc ctg ctt cag aca gcc ctt tct cct cct cct cct ccc acc        890
His Glu Ala Leu Leu Gln Thr Ala Leu Ser Pro Pro Pro Pro Pro Thr
            160                 165                 170 agg cct gtg tct cct ccc caa aag gca aaa gag gca cca aac acc caa        938
Arg Pro Val Ser Pro Pro Gln Lys Ala Lys Glu Ala Pro Asn Thr Gln
        175                 180                 185 gcc cag ccc atc tct gat gat gaa gcc agt gat ggg gaa gaa acc cag        986
Ala Gln Pro Ile Ser Asp Asp Glu Ala Ser Asp Gly Glu Glu Thr Gln
190                 195                 200                 205 gag gcc tgc agt atc cct ggg att ggg aag cgg atg gct gag aaa atc       1034
Glu Ala Cys Ser Ile Pro Gly Ile Gly Lys Arg Met Ala Glu Lys Ile
                210                 215                 220 ata gag atc ctg gag agc ggg cat ttg cgg aag ctg gac cat atc agt       1082
Ile Glu Ile Leu Glu Ser Gly His Leu Arg Lys Leu Asp His Ile Ser
                225                 230                 235 gag agc gtg cct gtc ttg gag ctc ttc tcc aac atc tgg gga gct ggg       1130
Glu Ser Val Pro Val Leu Glu Leu Phe Ser Asn Ile Trp Gly Ala Gly
            240                 245                 250 acc aag act gcc cag atg tgg tac caa cag ggc ttc cga agt ctg gaa       1178
Thr Lys Thr Ala Gln Met Trp Tyr Gln Gln Gly Phe Arg Ser Leu Glu
        255                 260                 265 gac atc cgc agc cag gcc tcc ctg aca acc cag cag gcc atc ggc ctg       1226
Asp Ile Arg Ser Gln Ala Ser Leu Thr Thr Gln Gln Ala Ile Gly Leu
270                 275                 280                 285 aag cat tac agt gac ttc ctg gaa cgt atg ccc agg gag gag gct aca       1274
Lys His Tyr Ser Asp Phe Leu Glu Arg Met Pro Arg Glu Glu Ala Thr
                290                 295                 300
```

```
gag att gag cag aca gtc cag aaa gca gcc cag gcc ttt aac tct ggg    1322
Glu Ile Glu Gln Thr Val Gln Lys Ala Ala Gln Ala Phe Asn Ser Gly
            305                 310                 315 ctg ctg tgt gtg gca tgt ggt tca tac cga cgg gga aag gcg acc tgt    1370
Leu Leu Cys Val Ala Cys Gly Ser Tyr Arg Arg Gly Lys Ala Thr Cys
        320                 325                 330 ggt gat gtc gac gtg ctc atc act cac cca gat ggc cgg tcc cac cgg    1418
Gly Asp Val Asp Val Leu Ile Thr His Pro Asp Gly Arg Ser His Arg
    335                 340                 345 ggt atc ttc agc cgc ctc ctt gac agt ctt cgg cag gaa ggg ttc ctc    1466
Gly Ile Phe Ser Arg Leu Leu Asp Ser Leu Arg Gln Glu Gly Phe Leu
350                 355                 360                 365 aca gat gac ttg gtg agc caa gag gag aat ggt cag caa cag aag tac    1514
Thr Asp Asp Leu Val Ser Gln Glu Glu Asn Gly Gln Gln Gln Lys Tyr
            370                 375                 380 ttg ggg gtg tgc cgg ctc cca ggg cca ggg cgg cgg cac cgg cgc ctg    1562
Leu Gly Val Cys Arg Leu Pro Gly Pro Gly Arg Arg His Arg Arg Leu
        385                 390                 395 gac atc atc gtg gtg ccc tat agc gag ttt gcc tgt gcc ctg ctc tac    1610
Asp Ile Ile Val Val Pro Tyr Ser Glu Phe Ala Cys Ala Leu Leu Tyr
    400                 405                 410 ttc acc ggc tct gca cac ttc aac cgc tcc atg cga gcc ctg gcc aaa    1658
Phe Thr Gly Ser Ala His Phe Asn Arg Ser Met Arg Ala Leu Ala Lys
415                 420                 425 acc aag ggc atg agt ctg tca gaa cat gcc ctc agc act gct gtg gtc    1706
Thr Lys Gly Met Ser Leu Ser Glu His Ala Leu Ser Thr Ala Val Val
430                 435                 440                 445 cgg aac acc cat ggc tgc aag gtg ggg cct ggc cga gtg ctg ccc act    1754
Arg Asn Thr His Gly Cys Lys Val Gly Pro Gly Arg Val Leu Pro Thr
            450                 455                 460 ccc act gag aag gat gtc ttc agg ctc tta ggc ctc ccc tac cga gaa    1802
Pro Thr Glu Lys Asp Val Phe Arg Leu Leu Gly Leu Pro Tyr Arg Glu
        465                 470                 475 cct gct gag cgg gac tgg tga cccatggctg ggggtgctga ggagagccga       1853
Pro Ala Glu Arg Asp Trp
    480 gttggactgg ctaccccctcc tggccaccca gtactccctc cagcctcagc tggctgaacc  1913 tcgccgctcc aaccaccagc ttcctcagcg agcagggccc agggctctgg gcctgaagca   1973 agagccagcc cggctcccag tgtctgcccg gctcccagtg tctgcccagc cctctcccag   2033 acaggagcag gctgccaccc cttctacctc accactgccc ctcgaagaat tttgcaaatg   2093 gccccttgcc ccattttaag caggagcagg tggctggttt gaagcccag gtatcccct     2153 tccctgctat gggaaaggcc aagctgctgg gtggggacag aagctgcagg ggagagggaa   2213 gcagccgtgc tgtcaacatc atccggcacc ctctggggta ggaaacagc cattccacat    2273 gtgttccctc tatccgtcct gcttcctggg cagctggtgg tgctgggaat ggggtgcccc   2333 agccttggtg aggacagtgt tgggaggccc aggggcccag taaagtgcat ttgacattga   2393 aaaaaaaaa                                                          2402

<210> SEQ ID NO 40
<211> LENGTH: 483
<212> TYPE: PRT
<213> ORGANISM: Homo sapiens

<400> SEQUENCE: 40

Met Asp Pro Arg Gly Ile Leu Lys Ala Phe Pro Lys Arg Gln Lys Ile
1               5                   10                  15
```

```
His Ala Asp Ala Ser Ser Lys Val Leu Ala Lys Ile Pro Arg Arg Glu
                20                  25                  30
Glu Gly Glu Glu Ala Glu Glu Trp Leu Ser Ser Leu Arg Ala His Val
             35                  40                  45
Val Arg Thr Gly Ile Gly Arg Ala Arg Ala Glu Leu Phe Glu Lys Gln
         50                  55                  60
Ile Val Gln His Gly Gly Gln Leu Cys Pro Ala Gln Gly Pro Gly Val
 65                  70                  75                  80
Thr His Ile Val Val Asp Glu Gly Met Asp Tyr Glu Arg Ala Leu Arg
                 85                  90                  95
Leu Leu Arg Leu Pro Gln Leu Pro Pro Gly Ala Gln Leu Val Lys Ser
             100                 105                 110
Ala Trp Leu Ser Leu Cys Leu Gln Glu Arg Arg Leu Val Asp Val Ala
         115                 120                 125
Gly Phe Ser Ile Phe Ile Pro Ser Arg Tyr Leu Asp His Pro Gln Pro
 130                 135                 140
Ser Lys Ala Glu Gln Asp Ala Ser Ile Pro Pro Gly Thr His Glu Ala
145                 150                 155                 160
Leu Leu Gln Thr Ala Leu Ser Pro Pro Pro Thr Arg Pro Val
                 165                 170                 175
Ser Pro Pro Gln Lys Ala Lys Glu Ala Pro Asn Thr Gln Ala Gln Pro
             180                 185                 190
Ile Ser Asp Asp Glu Ala Ser Asp Gly Glu Glu Thr Gln Glu Ala Cys
         195                 200                 205
Ser Ile Pro Gly Ile Gly Lys Arg Met Ala Glu Lys Ile Ile Glu Ile
         210                 215                 220
Leu Glu Ser Gly His Leu Arg Lys Leu Asp His Ile Ser Glu Ser Val
225                 230                 235                 240
Pro Val Leu Glu Leu Phe Ser Asn Ile Trp Gly Ala Gly Thr Lys Thr
                 245                 250                 255
Ala Gln Met Trp Tyr Gln Gln Gly Phe Arg Ser Leu Glu Asp Ile Arg
             260                 265                 270
Ser Gln Ala Ser Leu Thr Thr Gln Gln Ala Ile Gly Leu Lys His Tyr
         275                 280                 285
Ser Asp Phe Leu Glu Arg Met Pro Arg Glu Glu Ala Thr Glu Ile Glu
 290                 295                 300
Gln Thr Val Gln Lys Ala Ala Gln Ala Phe Asn Ser Gly Leu Leu Cys
305                 310                 315                 320
Val Ala Cys Gly Ser Tyr Arg Arg Gly Lys Ala Thr Cys Gly Asp Val
                 325                 330                 335
Asp Val Leu Ile Thr His Pro Asp Gly Arg Ser His Arg Gly Ile Phe
             340                 345                 350
Ser Arg Leu Leu Asp Ser Leu Arg Gln Glu Gly Phe Leu Thr Asp Asp
         355                 360                 365
Leu Val Ser Gln Glu Glu Asn Gly Gln Gln Gln Lys Tyr Leu Gly Val
         370                 375                 380
Cys Arg Leu Pro Gly Pro Gly Arg Arg His Arg Arg Leu Asp Ile Ile
385                 390                 395                 400
Val Val Pro Tyr Ser Glu Phe Ala Cys Ala Leu Leu Tyr Phe Thr Gly
                 405                 410                 415
Ser Ala His Phe Asn Arg Ser Met Arg Ala Leu Ala Lys Thr Lys Gly
             420                 425                 430
Met Ser Leu Ser Glu His Ala Leu Ser Thr Ala Val Val Arg Asn Thr
```

```
                435                 440                 445
His Gly Cys Lys Val Gly Pro Gly Arg Val Leu Pro Thr Pro Thr Glu
    450                 455                 460

Lys Asp Val Phe Arg Leu Leu Gly Leu Pro Tyr Arg Glu Pro Ala Glu
465                 470                 475                 480

Arg Asp Trp

<210> SEQ ID NO 41
<211> LENGTH: 2504
<212> TYPE: DNA
<213> ORGANISM: Homo sapiens
<220> FEATURE:
<221> NAME/KEY: CDS
<222> LOCATION: (372)..(1925)

<400> SEQUENCE: 41
ctgctggtaa gtggtctatt cctgcccacc cccgggtgac tagcttggcc agtagtcgac      60
cccacccggg gaccgactct ggggttgga gagactcttg gggccggggt cgggcactcc     120
agctttcttc tagccccgag ctgggattcc ctggcctgcg ccagctgcgt acacggcgag     180
tacaccgcac ctgcccggga cttcacccgc agctgcgaga ctcctccatt cccggagggc     240
tccccacacc tgctgcggcc gtgccccatc tccccgcagc tgcggcgctg agcaccccca     300
tgtcgagagg ctgagaccag acagcagcc ctgaccaacg ctccaatagg ccgggatcca     360
gccatacttc a atg gat ccc agg ggt atc ttg aag gca ttt ccc aag cgg      410
             Met Asp Pro Arg Gly Ile Leu Lys Ala Phe Pro Lys Arg
              1               5                  10 cag aaa att cat gct gat gca tca tca aaa gta ctt gca aag att cct      458
Gln Lys Ile His Ala Asp Ala Ser Ser Lys Val Leu Ala Lys Ile Pro
 15                  20                  25 agg agg gaa gag gga gaa gaa gca gaa gag tgg ctg agc tcc ctt cgg      506
Arg Arg Glu Glu Gly Glu Glu Ala Glu Glu Trp Leu Ser Ser Leu Arg
 30                  35                  40                  45 gcc cat gtt gtg cgc act ggc att gga cga gcc cgg gca gaa ctc ttt      554
Ala His Val Val Arg Thr Gly Ile Gly Arg Ala Arg Ala Glu Leu Phe
                 50                  55                  60 gag aag cag att gtt cag cat ggc ggc cag cta tgc cct gcc cag ggc      602
Glu Lys Gln Ile Val Gln His Gly Gly Gln Leu Cys Pro Ala Gln Gly
     65                  70                  75 cca ggt gtc act cac att gtg gtg gat gaa ggc atg gac tat gag cga      650
Pro Gly Val Thr His Ile Val Val Asp Glu Gly Met Asp Tyr Glu Arg
         80                  85                  90 gcc ctc cgc ctt ctc aga cta ccc cag ctg ccc ccg ggt gct cag ctg      698
Ala Leu Arg Leu Leu Arg Leu Pro Gln Leu Pro Pro Gly Ala Gln Leu
     95                 100                 105 gtg aag tca gcc tgg ctg agc ttg tgc ctt cag gag agg agg ctg gtg      746
Val Lys Ser Ala Trp Leu Ser Leu Cys Leu Gln Glu Arg Arg Leu Val
110                 115                 120                 125 gat gta gct gga ttc agc atc ttc atc ccc agt agg tac ttg gac cat      794
Asp Val Ala Gly Phe Ser Ile Phe Ile Pro Ser Arg Tyr Leu Asp His
                130                 135                 140 cca cag ccc agc aag gca gag cag gat gct tct att cct cct ggc acc      842
Pro Gln Pro Ser Lys Ala Glu Gln Asp Ala Ser Ile Pro Pro Gly Thr
            145                 150                 155 cat gag gcc ctg ctt cag aca gcc ctt tct cct cct cct ccc acc      890
His Glu Ala Leu Leu Gln Thr Ala Leu Ser Pro Pro Pro Pro Thr
        160                 165                 170 agg cct gtg tct cct ccc caa aag gca aaa gag gca cca aac acc caa      938
Arg Pro Val Ser Pro Pro Gln Lys Ala Lys Glu Ala Pro Asn Thr Gln
```

```
                175                 180                 185
gcc cag ccc atc tct gat gat gaa gcc agt gat ggg gaa gaa acc cag      986
Ala Gln Pro Ile Ser Asp Asp Glu Ala Ser Asp Gly Glu Glu Thr Gln
190                 195                 200                 205 gtt agt gca gct gat ctg gaa gcc ctc atc agt ggc cac tac ccc acc     1034
Val Ser Ala Ala Asp Leu Glu Ala Leu Ile Ser Gly His Tyr Pro Thr
                210                 215                 220 tcc ctt gag gga gat tgt gag cct agc cca gcc cct gct gtc ctg gat     1082
Ser Leu Glu Gly Asp Cys Glu Pro Ser Pro Ala Pro Ala Val Leu Asp
            225                 230                 235 aag tgg gtc tgt gca cag ccc tca agc cag aag gcg acc aat cac aac     1130
Lys Trp Val Cys Ala Gln Pro Ser Ser Gln Lys Ala Thr Asn His Asn
        240                 245                 250 ctc cat atc aca gag aag ctg gaa gtt ctg gcc aaa gcc tac agt gtt     1178
Leu His Ile Thr Glu Lys Leu Glu Val Leu Ala Lys Ala Tyr Ser Val
    255                 260                 265 cag gga gac aag tgg agg gcc ctg ggc tat gcc aag gcc atc aat gcc     1226
Gln Gly Asp Lys Trp Arg Ala Leu Gly Tyr Ala Lys Ala Ile Asn Ala
270                 275                 280                 285 ctc aag agc ttc cat aag cct gtc acc tcg tac cag ggc ttc cga agt     1274
Leu Lys Ser Phe His Lys Pro Val Thr Ser Tyr Gln Gly Phe Arg Ser
                290                 295                 300 ctg gaa gac atc cgc agc cag gcc tcc ctg aca acc cag cag gcc atc     1322
Leu Glu Asp Ile Arg Ser Gln Ala Ser Leu Thr Thr Gln Gln Ala Ile
            305                 310                 315 ggc ctg aag cat tac agt gac ttc ctg gaa cgt atg ccc agg gag gag     1370
Gly Leu Lys His Tyr Ser Asp Phe Leu Glu Arg Met Pro Arg Glu Glu
        320                 325                 330 gct aca gag att gag cag aca gtc cag aaa gca gcc cag gcc ttt aac     1418
Ala Thr Glu Ile Glu Gln Thr Val Gln Lys Ala Ala Gln Ala Phe Asn
    335                 340                 345 tct ggg ctg ctg tgt gtg gca tgt ggt tca tac cga cgg gga aag gcg     1466
Ser Gly Leu Leu Cys Val Ala Cys Gly Ser Tyr Arg Arg Gly Lys Ala
350                 355                 360                 365 acc tgt ggt gat gtc gac gtg ctc atc act cac cca gat ggc cgg tcc     1514
Thr Cys Gly Asp Val Asp Val Leu Ile Thr His Pro Asp Gly Arg Ser
                370                 375                 380 cac cgg ggt atc ttc agc cgc ctc ctt gac agt ctt cgg cag gaa ggg     1562
His Arg Gly Ile Phe Ser Arg Leu Leu Asp Ser Leu Arg Gln Glu Gly
            385                 390                 395 ttc ctc aca gat gac ttg gtg agc caa gag gag aat ggt cag caa cag     1610
Phe Leu Thr Asp Asp Leu Val Ser Gln Glu Glu Asn Gly Gln Gln Gln
        400                 405                 410 aag tac ttg ggg gtg tgc cgg ctc cca ggg cca ggg cgg cgg cac cgg     1658
Lys Tyr Leu Gly Val Cys Arg Leu Pro Gly Pro Gly Arg Arg His Arg
    415                 420                 425 cgc ctg gac atc atc gtg gtg ccc tat agc gag ttt gcc tgt gcc ctg     1706
Arg Leu Asp Ile Ile Val Val Pro Tyr Ser Glu Phe Ala Cys Ala Leu
430                 435                 440                 445 ctc tac ttc acc ggc tct gca cac ttc aac cgc tcc atg cga gcc ctg     1754
Leu Tyr Phe Thr Gly Ser Ala His Phe Asn Arg Ser Met Arg Ala Leu
                450                 455                 460 gcc aaa acc aag ggc atg agt ctg tca gaa cat gcc ctc agc act gct     1802
Ala Lys Thr Lys Gly Met Ser Leu Ser Glu His Ala Leu Ser Thr Ala
            465                 470                 475 gtg gtc cgg aac acc cat ggc tgc aag gtg ggg cct ggc cga gtg ctg     1850
Val Val Arg Asn Thr His Gly Cys Lys Val Gly Pro Gly Arg Val Leu
        480                 485                 490 ccc act ccc act gag aag gat gtc ttc agg ctc tta ggc ctc ccc tac     1898
```

-continued

```
Pro Thr Pro Thr Glu Lys Asp Val Phe Arg Leu Leu Gly Leu Pro Tyr
    495                 500                 505 cga gaa cct gct gag cgg gac tgg tga cccatggctg ggggtgctga          1945
Arg Glu Pro Ala Glu Arg Asp Trp
510                 515 ggagagccga gttggactgg ctacccctcc tggccaccca gtactccctc cagcctcagc  2005
tggctgaacc tcgccgctcc aaccaccagc ttcctcagcg agcagggccc agggctctgg  2065
gcctgaagca agagccagcc cggctcccag tgtctgcccg gctcccagtg tctgcccagc  2125
cctctcccag acaggagcag gctgccaccc cttctacctc accactgccc ctcgaagaat  2185
tttgcaaatg gccccttgcc ccattttaag caggagcagg tggctggttt gaagcccag   2245 gtatcccct tccctgctat gggaaaggcc aagctgctgg gtggggacag aagctgcagg   2305
ggagagggaa gcagccgtgc tgtcaacatc atccggcacc ctctggggta ggagaacagc  2365
cattccacat gtgttccctc tatccgtcct gcttcctggg cagctggtgg tgctgggaat  2425
ggggtgcccc agccttggtg aggacagtgt tgggaggccc aggggcccag taaagtgcat  2485
ttgacattga aaaaaaaaa                                               2504
```

<210> SEQ ID NO 42
<211> LENGTH: 517
<212> TYPE: PRT
<213> ORGANISM: Homo sapiens

<400> SEQUENCE: 42

```
Met Asp Pro Arg Gly Ile Leu Lys Ala Phe Pro Lys Arg Gln Lys Ile
1               5                   10                  15

His Ala Asp Ala Ser Ser Lys Val Leu Ala Lys Ile Pro Arg Arg Glu
            20                  25                  30

Glu Gly Glu Glu Ala Glu Glu Trp Leu Ser Ser Leu Arg Ala His Val
        35                  40                  45

Val Arg Thr Gly Ile Gly Arg Ala Arg Ala Glu Leu Phe Glu Lys Gln
    50                  55                  60

Ile Val Gln His Gly Gly Gln Leu Cys Pro Ala Gln Gly Pro Gly Val
65                  70                  75                  80

Thr His Ile Val Val Asp Glu Gly Met Asp Tyr Glu Arg Ala Leu Arg
                85                  90                  95

Leu Leu Arg Leu Pro Gln Leu Pro Pro Gly Ala Gln Leu Val Lys Ser
            100                 105                 110

Ala Trp Leu Ser Leu Cys Leu Gln Glu Arg Arg Leu Val Asp Val Ala
        115                 120                 125

Gly Phe Ser Ile Phe Ile Pro Ser Arg Tyr Leu Asp His Pro Gln Pro
    130                 135                 140

Ser Lys Ala Glu Gln Asp Ala Ser Ile Pro Pro Gly Thr His Glu Ala
145                 150                 155                 160

Leu Leu Gln Thr Ala Leu Ser Pro Pro Pro Thr Arg Pro Val
                165                 170                 175

Ser Pro Pro Gln Lys Ala Lys Glu Ala Pro Asn Thr Gln Ala Gln Pro
            180                 185                 190

Ile Ser Asp Asp Glu Ala Ser Asp Gly Glu Glu Thr Gln Val Ser Ala
        195                 200                 205

Ala Asp Leu Glu Ala Leu Ile Ser Gly His Tyr Pro Thr Ser Leu Glu
    210                 215                 220

Gly Asp Cys Glu Pro Ser Pro Ala Pro Ala Val Leu Asp Lys Trp Val
225                 230                 235                 240
```

Cys Ala Gln Pro Ser Ser Gln Lys Ala Thr Asn His Asn Leu His Ile
            245                 250                 255

Thr Glu Lys Leu Glu Val Leu Ala Lys Ala Tyr Ser Val Gln Gly Asp
        260                 265                 270

Lys Trp Arg Ala Leu Gly Tyr Ala Lys Ala Ile Asn Ala Leu Lys Ser
    275                 280                 285

Phe His Lys Pro Val Thr Ser Tyr Gln Gly Phe Arg Ser Leu Glu Asp
290                 295                 300

Ile Arg Ser Gln Ala Ser Leu Thr Thr Gln Ala Ile Gly Leu Lys
305                 310                 315                 320

His Tyr Ser Asp Phe Leu Glu Arg Met Pro Arg Glu Ala Thr Glu
                325                 330                 335

Ile Glu Gln Thr Val Gln Lys Ala Ala Gln Ala Phe Asn Ser Gly Leu
            340                 345                 350

Leu Cys Val Ala Cys Gly Ser Tyr Arg Arg Gly Lys Ala Thr Cys Gly
        355                 360                 365

Asp Val Asp Val Leu Ile Thr His Pro Asp Gly Arg Ser His Arg Gly
    370                 375                 380

Ile Phe Ser Arg Leu Leu Asp Ser Leu Arg Gln Glu Gly Phe Leu Thr
385                 390                 395                 400

Asp Asp Leu Val Ser Gln Glu Glu Asn Gly Gln Gln Lys Tyr Leu
                405                 410                 415

Gly Val Cys Arg Leu Pro Gly Pro Gly Arg Arg His Arg Arg Leu Asp
            420                 425                 430

Ile Ile Val Val Pro Tyr Ser Glu Phe Ala Cys Ala Leu Leu Tyr Phe
        435                 440                 445

Thr Gly Ser Ala His Phe Asn Arg Ser Met Arg Ala Leu Ala Lys Thr
    450                 455                 460

Lys Gly Met Ser Leu Ser Glu His Ala Leu Ser Thr Ala Val Val Arg
465                 470                 475                 480

Asn Thr His Gly Cys Lys Val Gly Pro Gly Arg Val Leu Pro Thr Pro
                485                 490                 495

Thr Glu Lys Asp Val Phe Arg Leu Leu Gly Leu Pro Tyr Arg Glu Pro
            500                 505                 510

Ala Glu Arg Asp Trp
        515

<210> SEQ ID NO 43
<211> LENGTH: 2375
<212> TYPE: DNA
<213> ORGANISM: Homo sapiens
<220> FEATURE:
<221> NAME/KEY: CDS
<222> LOCATION: (372)..(1796)

<400> SEQUENCE: 43
ctgctggtaa gtggtctatt cctgcccacc cccgggtgac tagcttggcc agtagtcgac     60
cccacccggg gaccgactct ggggttgga gagactcttg gggccggggt cgggcactcc    120
agctttcttc tagccccgag ctgggattcc ctggcctgcg ccagctgcgt acacggcgag    180
tacaccgcac ctgcccggga cttcaccgc agctgcgaga ctcctccatt cccgagggc     240 tccccacacc tgctgcggcc gtgccccatc tccccgcagc tgcggcgctg agcaccccca    300
tgtcgagagg ctgagaccag acagcagcc ctgaccaacg ctccaatagg ccgggatcca    360
gccatacttc a atg gat ccc agg ggt atc ttg aag gca ttt ccc aag cgg    410

```
              Met Asp Pro Arg Gly Ile Leu Lys Ala Phe Pro Lys Arg
                1           5                  10 cag aaa att cat gct gat gca tca tca aaa gta ctt gca aag att cct        458
Gln Lys Ile His Ala Asp Ala Ser Ser Lys Val Leu Ala Lys Ile Pro
     15              20                  25 agg agg gaa gag gga gaa gaa gca gaa gag tgg ctg agc tcc ctt cgg        506
Arg Arg Glu Glu Gly Glu Glu Ala Glu Glu Trp Leu Ser Ser Leu Arg
 30              35                  40                  45 gcc cat gtt gtg cgc act ggc att gga cga gcc cgg gca gaa ctc ttt        554
Ala His Val Val Arg Thr Gly Ile Gly Arg Ala Arg Ala Glu Leu Phe
                 50                  55                  60 gag aag cag att gtt cag cat ggc ggc cag cta tgc cct gcc cag ggc        602
Glu Lys Gln Ile Val Gln His Gly Gly Gln Leu Cys Pro Ala Gln Gly
             65                  70                  75 cca ggt gtc act cac att gtg gtg gat gaa ggc atg gac tat gag cga        650
Pro Gly Val Thr His Ile Val Val Asp Glu Gly Met Asp Tyr Glu Arg
         80                  85                  90 gcc ctc cgc ctt ctc aga cta ccc cag ctg ccc cgg ggt gct cag ctg        698
Ala Leu Arg Leu Leu Arg Leu Pro Gln Leu Pro Pro Gly Ala Gln Leu
     95                 100                 105 gtg aag tca gcc tgg ctg agc ttg tgc ctt cag gag agg agg ctg gtg        746
Val Lys Ser Ala Trp Leu Ser Leu Cys Leu Gln Glu Arg Arg Leu Val
110                 115                 120                 125 gat gta gct gga ttc agc atc ttc atc ccc agt agg tac ttg gac cat        794
Asp Val Ala Gly Phe Ser Ile Phe Ile Pro Ser Arg Tyr Leu Asp His
                130                 135                 140 cca cag ccc agc aag gca gag cag gat gct tct att cct cct ggc acc        842
Pro Gln Pro Ser Lys Ala Glu Gln Asp Ala Ser Ile Pro Pro Gly Thr
            145                 150                 155 cat gag gcc ctg ctt cag aca gcc ctt tct cct cct cct cct ccc acc        890
His Glu Ala Leu Leu Gln Thr Ala Leu Ser Pro Pro Pro Pro Pro Thr
        160                 165                 170 agg cct gtg tct cct ccc caa aag gca aaa gag gca cca aac acc caa        938
Arg Pro Val Ser Pro Pro Gln Lys Ala Lys Glu Ala Pro Asn Thr Gln
    175                 180                 185 gcc cag ccc atc tct gat gat gaa gcc agt gat ggg gaa gaa acc cag        986
Ala Gln Pro Ile Ser Asp Asp Glu Ala Ser Asp Gly Glu Glu Thr Gln
190                 195                 200                 205 gtt agt gca gct gat ctg gaa gcc ctc atc agt ggc cac tac ccc acc       1034
Val Ser Ala Ala Asp Leu Glu Ala Leu Ile Ser Gly His Tyr Pro Thr
                210                 215                 220 tcc ctt gag gga gat tgt gag cct agc cca gcc cct gct gtc ctg gat       1082
Ser Leu Glu Gly Asp Cys Glu Pro Ser Pro Ala Pro Ala Val Leu Asp
            225                 230                 235 aag tgg gtc tgt gca cag ccc tca agc cag aag gcg acc aat cac aac       1130
Lys Trp Val Cys Ala Gln Pro Ser Ser Gln Lys Ala Thr Asn His Asn
        240                 245                 250 ctc cat atc aca gag aag ctg gaa gtt ctg gcc aaa gcc tac agt gtt       1178
Leu His Ile Thr Glu Lys Leu Glu Val Leu Ala Lys Ala Tyr Ser Val
    255                 260                 265 cag gga gac aag tgg agg gcc ctg ggc tat gcc aag gcc atc aat gcc       1226
Gln Gly Asp Lys Trp Arg Ala Leu Gly Tyr Ala Lys Ala Ile Asn Ala
270                 275                 280                 285 ctc aag agc ttc cat aag cct gtc acc tcg tac cag gtc cag aaa gca       1274
Leu Lys Ser Phe His Lys Pro Val Thr Ser Tyr Gln Val Gln Lys Ala
                290                 295                 300 gcc cag gcc ttt aac tct ggg ctg ctg tgt gtg gca tgt ggt tca tac       1322
Ala Gln Ala Phe Asn Ser Gly Leu Leu Cys Val Ala Cys Gly Ser Tyr
            305                 310                 315
```

```
cga cgg gga aag gcg acc tgt ggt gat gtc gac gtg ctc atc act cac    1370
Arg Arg Gly Lys Ala Thr Cys Gly Asp Val Asp Val Leu Ile Thr His
        320             325                 330 cca gat ggc cgg tcc cac cgg ggt atc ttc agc cgc ctc ctt gac agt    1418
Pro Asp Gly Arg Ser His Arg Gly Ile Phe Ser Arg Leu Leu Asp Ser
    335                 340                 345 ctt cgg cag gaa ggg ttc ctc aca gat gac ttg gtg agc caa gag gag    1466
Leu Arg Gln Glu Gly Phe Leu Thr Asp Asp Leu Val Ser Gln Glu Glu
350                 355                 360                 365 aat ggt cag caa cag aag tac ttg ggg gtg tgc cgg ctc cca ggg cca    1514
Asn Gly Gln Gln Gln Lys Tyr Leu Gly Val Cys Arg Leu Pro Gly Pro
                370                 375                 380 ggg cgg cgg cac cgg cgc ctg gac atc atc gtg gtg ccc tat agc gag    1562
Gly Arg Arg His Arg Arg Leu Asp Ile Ile Val Val Pro Tyr Ser Glu
            385                 390                 395 ttt gcc tgt gcc ctg ctc tac ttc acc ggc tct gca cac ttc aac cgc    1610
Phe Ala Cys Ala Leu Leu Tyr Phe Thr Gly Ser Ala His Phe Asn Arg
        400                 405                 410 tcc atg cga gcc ctg gcc aaa acc aag ggc atg agt ctg tca gaa cat    1658
Ser Met Arg Ala Leu Ala Lys Thr Lys Gly Met Ser Leu Ser Glu His
    415                 420                 425 gcc ctc agc act gct gtg gtc cgg aac acc cat ggc tgc aag gtg ggg    1706
Ala Leu Ser Thr Ala Val Val Arg Asn Thr His Gly Cys Lys Val Gly
430                 435                 440                 445 cct ggc cga gtg ctg ccc act ccc act gag aag gat gtc ttc agg ctc    1754
Pro Gly Arg Val Leu Pro Thr Pro Thr Glu Lys Asp Val Phe Arg Leu
                450                 455                 460 tta ggc ctc ccc tac cga gaa cct gct gag cgg gac tgg tga            1796
Leu Gly Leu Pro Tyr Arg Glu Pro Ala Glu Arg Asp Trp
            465                 470 cccatggctg ggggtgctga ggagagccga gttggactgg ctaccccctcc tggccaccca    1856 gtactccctc cagcctcagc tggctgaacc tcgccgctcc aaccaccagc ttcctcagcg    1916
agcagggccc agggctctgg gcctgaagca agagccagcc cggctcccag tgtctgcccg    1976
gctcccagtg tctgcccagc cctctcccag acaggagcag gctgccaccc cttctacctc    2036
accactgccc ctcgaagaat tttgcaaatg gccccttgcc ccatttttaag caggagcagg    2096 tggctggttt gaagcccag gtatccccct tccctgctat gggaaaggcc aagctgctgg    2156
gtggggacag aagctgcagg ggagagggaa gcagccgtgc tgtcaacatc atccggcacc    2216
ctctggggta ggagaacagc cattccacat gtgttccctc tatccgtcct gcttcctggg    2276
cagctggtgg tgctgggaat ggggtgcccc agccttggtg aggacagtgt tgggaggccc    2336
aggggcccag taaagtgcat ttgacattga aaaaaaaaa                            2375

<210> SEQ ID NO 44
<211> LENGTH: 474
<212> TYPE: PRT
<213> ORGANISM: Homo sapiens

<400> SEQUENCE: 44

Met Asp Pro Arg Gly Ile Leu Lys Ala Phe Pro Lys Arg Gln Lys Ile
1               5                   10                  15

His Ala Asp Ala Ser Ser Lys Val Leu Ala Lys Ile Pro Arg Arg Glu
            20                  25                  30

Glu Gly Glu Glu Ala Glu Glu Trp Leu Ser Ser Leu Arg Ala His Val
        35                  40                  45

Val Arg Thr Gly Ile Gly Arg Ala Arg Ala Glu Leu Phe Glu Lys Gln
    50                  55                  60
```

```
Ile Val Gln His Gly Gly Gln Leu Cys Pro Ala Gln Gly Pro Gly Val
65                  70                  75                  80

Thr His Ile Val Val Asp Glu Gly Met Asp Tyr Glu Arg Ala Leu Arg
                85                  90                  95

Leu Leu Arg Leu Pro Gln Leu Pro Pro Gly Ala Gln Leu Val Lys Ser
            100                 105                 110

Ala Trp Leu Ser Leu Cys Leu Gln Glu Arg Arg Leu Val Asp Val Ala
        115                 120                 125

Gly Phe Ser Ile Phe Ile Pro Ser Arg Tyr Leu Asp His Pro Gln Pro
    130                 135                 140

Ser Lys Ala Glu Gln Asp Ala Ser Ile Pro Pro Gly Thr His Glu Ala
145                 150                 155                 160

Leu Leu Gln Thr Ala Leu Ser Pro Pro Pro Thr Arg Pro Val
            165                 170                 175

Ser Pro Pro Gln Lys Ala Lys Glu Ala Pro Asn Thr Gln Ala Gln Pro
            180                 185                 190

Ile Ser Asp Asp Glu Ala Ser Asp Gly Glu Glu Thr Gln Val Ser Ala
            195                 200                 205

Ala Asp Leu Glu Ala Leu Ile Ser Gly His Tyr Pro Thr Ser Leu Glu
        210                 215                 220

Gly Asp Cys Glu Pro Ser Pro Ala Pro Ala Val Leu Asp Lys Trp Val
225                 230                 235                 240

Cys Ala Gln Pro Ser Ser Gln Lys Ala Thr Asn His Asn Leu His Ile
            245                 250                 255

Thr Glu Lys Leu Glu Val Leu Ala Lys Ala Tyr Ser Val Gln Gly Asp
            260                 265                 270

Lys Trp Arg Ala Leu Gly Tyr Ala Lys Ala Ile Asn Ala Leu Lys Ser
            275                 280                 285

Phe His Lys Pro Val Thr Ser Tyr Gln Val Gln Lys Ala Ala Gln Ala
    290                 295                 300

Phe Asn Ser Gly Leu Leu Cys Val Ala Cys Gly Ser Tyr Arg Arg Gly
305                 310                 315                 320

Lys Ala Thr Cys Gly Asp Val Asp Val Leu Ile Thr His Pro Asp Gly
            325                 330                 335

Arg Ser His Arg Gly Ile Phe Ser Arg Leu Leu Asp Ser Leu Arg Gln
            340                 345                 350

Glu Gly Phe Leu Thr Asp Asp Leu Val Ser Gln Glu Glu Asn Gly Gln
            355                 360                 365

Gln Gln Lys Tyr Leu Gly Val Cys Arg Leu Pro Gly Pro Gly Arg Arg
    370                 375                 380

His Arg Arg Leu Asp Ile Ile Val Val Pro Tyr Ser Glu Phe Ala Cys
385                 390                 395                 400

Ala Leu Leu Tyr Phe Thr Gly Ser Ala His Phe Asn Arg Ser Met Arg
            405                 410                 415

Ala Leu Ala Lys Thr Lys Gly Met Ser Leu Ser Glu His Ala Leu Ser
            420                 425                 430

Thr Ala Val Val Arg Asn Thr His Gly Cys Lys Val Gly Pro Gly Arg
            435                 440                 445

Val Leu Pro Thr Pro Thr Glu Lys Asp Val Phe Arg Leu Leu Gly Leu
            450                 455                 460

Pro Tyr Arg Glu Pro Ala Glu Arg Asp Trp
465                 470
```

```
<210> SEQ ID NO 45
<211> LENGTH: 18
<212> TYPE: DNA
<213> ORGANISM: Artificial sequence
<220> FEATURE:
<223> OTHER INFORMATION: oligonucleotide primer

<400> SEQUENCE: 45
ggagcggttg aagtgtgc                                                 18

<210> SEQ ID NO 46
<211> LENGTH: 18
<212> TYPE: DNA
<213> ORGANISM: Artificial sequence
<220> FEATURE:
<223> OTHER INFORMATION: oligonucleotide primer

<400> SEQUENCE: 46
cctcgtacca gggcttcc                                                 18

<210> SEQ ID NO 47
<211> LENGTH: 20
<212> TYPE: DNA
<213> ORGANISM: Artificial sequence
<220> FEATURE:
<223> OTHER INFORMATION: oligonucleotide primer

<400> SEQUENCE: 47
cacctcgtac caggtccaga                                               20

<210> SEQ ID NO 48
<211> LENGTH: 20
<212> TYPE: DNA
<213> ORGANISM: Artificial sequence
<220> FEATURE:
<223> OTHER INFORMATION: oligonucleotide primer

<400> SEQUENCE: 48
ggcatgtggt tcataccgac                                               20

<210> SEQ ID NO 49
<211> LENGTH: 19
<212> TYPE: DNA
<213> ORGANISM: Artificial sequence
<220> FEATURE:
<223> OTHER INFORMATION: oligonucleotide primer

<400> SEQUENCE: 49
ttcctgccga agactgtca                                                19
```